(12) United States Patent
Daniell

(10) Patent No.: US 7,767,885 B2
(45) Date of Patent: Aug. 3, 2010

(54) PLASTID GENETIC ENGINEERING VIA SOMATIC EMBRYOGENESIS

(75) Inventor: Henry Daniell, Winter Park, FL (US)

(73) Assignee: University of Central Florida Research Foundation, Inc., Orlando, FL (US)

( * ) Notice: Subject to any disclaimer, the term of this patent is extended or adjusted under 35 U.S.C. 154(b) by 0 days.

(21) Appl. No.: 11/190,122

(22) Filed: Jul. 25, 2005

(65) Prior Publication Data

US 2006/0031964 A1 Feb. 9, 2006

Related U.S. Application Data

(63) Continuation-in-part of application No. 10/519,821, filed as application No. PCT/US03/21157 on Jul. 3, 2003, application No. 11/190,122, which is a continuation-in-part of application No. 10/500,351, filed as application No. PCT/US02/41503 on Dec. 26, 2002, now Pat. No. 7,354,760.

(60) Provisional application No. 60/393,651, filed on Jul. 3, 2002, provisional application No. 60/344,704, filed on Dec. 26, 2001, provisional application No. 60/400,816, filed on Aug. 2, 2002, provisional application No. 60/393,428, filed on Jul. 3, 2002, provisional application No. 60/590,848, filed on Jul. 23, 2004, provisional application No. 60/590,751, filed on Jul. 23, 2004.

(51) Int. Cl.
    *C12N 15/82* (2006.01)
(52) U.S. Cl. ..................................... 800/298
(58) Field of Classification Search ............. None
    See application file for complete search history.

(56) References Cited

U.S. PATENT DOCUMENTS

| 5,693,507 | A |   | 12/1997 | Daniell et al. |         |
|-----------|---|---|---------|----------------|---------|
| 5,877,402 | A | * | 3/1999  | Maliga et al.  | 800/298 |
| 5,925,806 | A | * | 7/1999  | McBride et al. | 800/298 |
| 5,932,479 | A |   | 8/1999  | Daniell et al. |         |

OTHER PUBLICATIONS

Apse, M.P. et al., "Engineering salt tolerance in plants", *Current opinion in Biotechnol.*, 2002, pp. 146-150, vol. 213.
Corneille, S., et al. "Efficient elimination of selectable marker genes from the plastid genome by the CRE-lox site-specific recombination system", *Plant J.*, 2001, pp. 171-178, vol. 27.
Daniell, H., et al. "Multigene engineering: Dawn of an exciting new era in biotechnology", *Curr. Opin.Biotechnol.*, 2002, pp. 136-141 vol. 13.
Daniell, H. et al., "Transient foreign gene-expression in chloroplasts of cultured tobacco cells after biolistic delivery of chloroplast vectors", *Proc. Natl. Acad. Sci. U. S. A.*, 1990, pp. 88-92, vol. 87.
Daniell, H., "Medical molecular farming: production of antibodies, biopharmaceuticals and edible vaccines in plants", *Trends in Plant Sci.*, 2001, pp. 219-226, vol. 6, No. 5.

Daniell, H., "Molecular strategies for gene containment in transgenic crops", *Nature Biotechnol.*, 2002, pp. 581-586, vol. 20.
Daniell, H., "Transformation and foreign gene expression in plants mediated by micoprojectile bombardment", *Methods Mol. Biol.*, 1997, pp. 463-489, vol. 62.
Daniell, H., et al., "Containment of herbicide resistance through genetic engineering of the chloroplast genome", *Nat. Biotechnol.*, 1998, pp. 345-348, vol. 16.
Daniell, H., et al., "Milestones in chloroplast genetic engineering: an environmentally friendly era in biotechnology", *Trends Plant Sci.*, 2002, pp. 84-91, vol. 7, No. 2.
Daniell, H., et al., "Expression of Native cholera toxin B subunit gene and assembly as functional oligomers in transgenic tobacco chloroplasts", *J. Mol. Biol.*, 2001, pp. 1001-1009 vol. 311.
Daniell, H., et al., "Marker free transgenic plants: engineering the chloroplast genome without the use of antibiotic selection", *Curr. Genet.*, 2001, pp. 109-116, vol. 39.
Decosa, B., et al., "Overexpression of the *Bt* Cry2Aa2 operon in chloroplasts leads to formation of insecticidal crystals", *Nat. Biotechnol.*, 2001, pp. 71-74 vol. 19.
Degray, G. et al., "Expression of an antimicrobial peptide via the chloroplast genome to control phytopathogenic bacteria and fungi", *Plant Physiol.*, 2001, pp. 852-862, vol. 127.
Figueroa-Soto, C.G. et al., "Immunolocalization of Betaine Aldehyde Dehydrogenase in Porcine Kidney", *Biochemical and Biophysical Research Communications.*, 1999, pp. 732-736 vol. 258, No. 3.
Gamborg, O.L., et al., Nutrient requirements of suspension cultures of soybean root cells. *Exp. Cell Res.* 1968, pp. 151-158, vol. 50, No. 1 (Abstract Only).
Guda, C., et al., "Stable expression of biodegradable protein-based polymer in tobacco chloroplasts", *Plant Cell Rep.*, 2000, pp. 257-262 vol. 19.
Hajdukiewicz, P., et al., "Multiple pathways for Cre/lox-mediated recombination in plastids", *Plant J.*, 2001, pp. 161-170, vol. 27(2).
Hibberd, J. M. et al. "Transient expression of green fluorescent protein in various plastid types following microprojectile bombardment", *The Plant Journal*, 1998, pp. 627-632, vol. 16, No. 5.

(Continued)

*Primary Examiner*—Anne R Kubelik
(74) *Attorney, Agent, or Firm*—Timothy H. Van Dyke; Beusse Wolter Sanks Mora & Maire

(57) ABSTRACT

A method of transforming plant plastids and regenerating fertile transplastomic plants by somatic embryogenesis is disclosed. The method involves transforming a plant plastid in a plant cell capable of being regenerated through somatic embryogenesis with a plastid expression cassette comprising one or more selectable marker genes that express in both green and non-green tissue and in light and dark conditions wherein the selectable marker gene product provides resistance of the plant cell to a selection agent. The transplastomic plant cell is cultured in the presence of the selection agent under conditions to cause the formation of a somatic embryo. The somatic embryo is grown into a fertile transplastomic plant. Preferably, the expression cassette contains two different selectable marker genes that express different proteins that provide plant cell resistance to the same selection agent.

4 Claims, 40 Drawing Sheets

OTHER PUBLICATIONS

Hou, B-K. et al., "Chloroplast Transformation in Oilseed Rape", *Transgenic Res.* 2003, pp. 111-114 vol. 12.

Huang, F.C. et al., "Efficient plastid transformation in tobacco using the *aphA-6* gene and kanamycin selection", *Mol. Gen. Genomics*, 2002, pp. 19-27, vol. 268.

Incharoensakdi, A. et al., "Salt stress enhances choline uptake in the halotolerant cyanobacterium *Aphanothece halophytica*" *Biochimica et Biophysica Acta (BBA)* 2003, pp. 102-109, vol. 1621.

Iamtham, S., et al., "Removal of antibiotic resistance genes from transgenic tobacco plastids", *Nat. Biotechnol.*: 2000, pp. 1172-1176, vol. 18.

Khan, M. S. et al., "Fluorescent antibiotic resistance marker for tracking plastid transformation in higher plants", *Nat. Biotechnol.* 1999, pp. 910-915, vol. 17.

Kota, M. et al. "Overexpression of the *Bacillus thuringiensis* (Bt) Cry2Aa2 protein in chloroplasts confers resistance to plants against susceptible and *Bt*-resistant insects", *Proc.

PLASMID NAME: pDD-Dc-aphA-6/nptII

PLASMID NAME: pDD-Dc-aadA/BADH

PLASMID NAME: pDD-Dc-gfp/BADH

* Means destroyed

PLASMID NAME: pDD-*Gh-aph*A-6/*npt*II

PLASMID NAME: pDD-Gh-aadA/BADH

PLASMID NAME: pDD-*Gh-gfp*/BADH

PLASMID NAME: pDD-*Pv-aph*A-6/*npt*II *(switchgrass)*

* Means destroyed

PLASMID NAME: pDD-Pv-aadA/BADH (switchgrass)

* Means destroyed

PLASMID NAME: pDD-Cd-aphA-6/nptII (bermudagrass)

* Means destroyed

PLASMID NAME: pDD-Os-aphA-6/nptII

PLASMID NAME: pDD-*Ta-aadA/BADH*

* Means destroyed

PLASMID NAME: pDD-Ta-gfp/BADH

PLASMID NAME: pDD-*Hv-aphA-6/nptII*

Double Barrel Plastid Vector harboring *aphA-6* and *aphA-2* genes conferring resistance to aminoglycosides

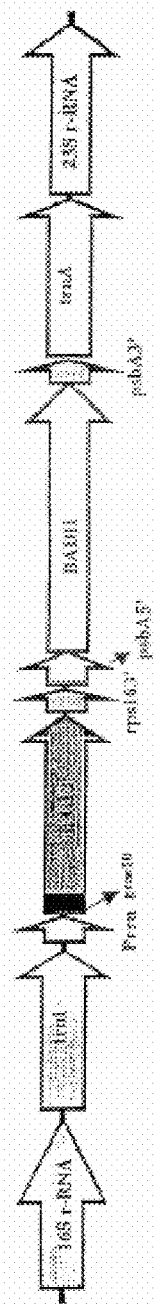
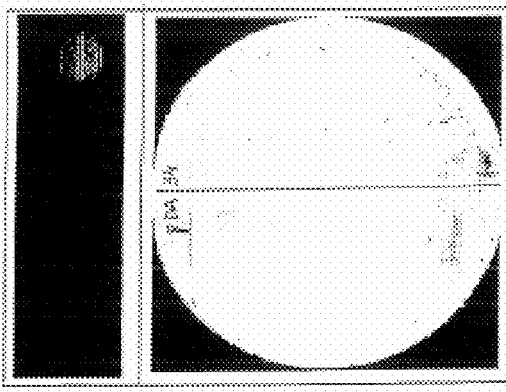
FIG 29

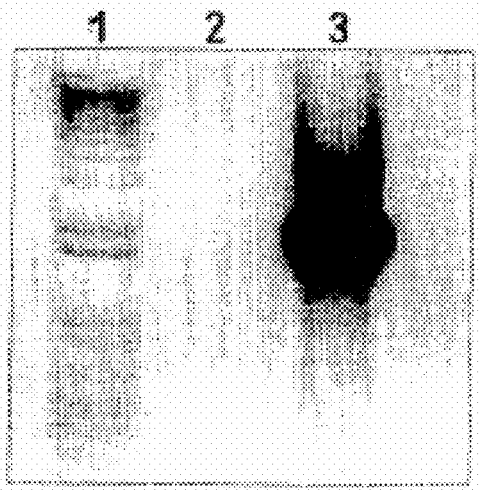 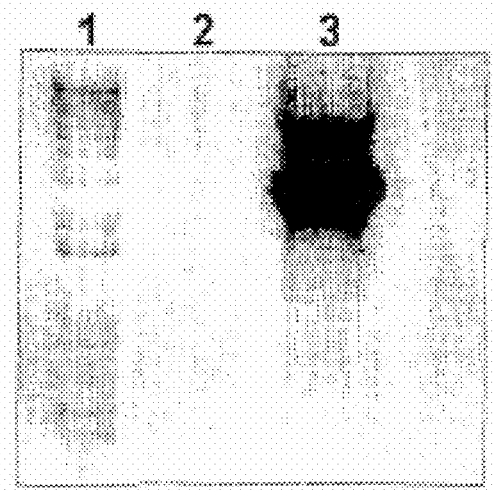
FIG 34A — Primers: 3P-aphA6
FIG 34B — Primers: 16SF-aphA6

Table 1. Cotton calli (8–10 weeks old) bombarded with the vector pDD-Gh-aphA-6/nptII and pKD-Gh-aphA-6, coated on 0.6 µm gold particles using indicated parameters. The transgenic cell lines selected on MST1 medium containing 50 mg/l kanamycin after bombardments were confirmed by PCR for site-specific transgene integration.

| Plastid vector | Rupture disc (psi) | Distance[a] (cm) | No. of plates[b] | Total events[c] | Efficiency (%)[d] |
|---|---|---|---|---|---|
| aphA6/nptII | 650 | 6 | 15 | 0 | 0 |
| aphA6/nptII | 650 | 9 | 31 | 13 | 42 |
| aphA6/nptII | 900 | 9 | 17 | 5 | 29 |
| aphA6/nptII | 900 | 12 | 18 | 3 | 17 |
| aphA6/nptII | 1100 | 9 | 32 | 2 | 6 |
| aphA6/nptII | 1100 | 12 | 46 | 5 | 11 |
| aphA6 | 650 | 9 | 40 | 2 | 5 |

[a] Distance between rupture disc and target tissues.
[b] Number of plates bombarded (1 mm thick · 20 mm in diameter layer of cotton calli from cultivar Coker 310FR).
[c] Total number of independent transgenic events recovered.
[d] Transformation efficiency (total number of events · 100/total number of plates bombarded).

FIG. 37

PLASTID GENETIC ENGINEERING VIA SOMATIC EMBRYOGENESIS

CROSS-REFERENCE TO A RELATED APPLICATIONS

This application is a Continuation-In-Part (CIP) of U.S. Ser. No. 10/519,821 filed on Sep. 28, 2005; which is the National Phase of International Application No. PCT/US2003/021157 filed Jul. 3, 2003; which claims priority to U.S. Ser. No. 60/393,651, filed Jul. 3, 2002. This application is also a CIP of U.S. Ser. No. 10/500,351 filed on Jan. 3, 2005; now U.S. Pat. No. 7,354,760; which is the National Phase of International Application No. PCT/US2002/041503, filed Dec. 26, 2002 which claims priority to U.S. Ser. No. 60/344,704, filed Dec. 26, 2001, U.S. Ser. No. 60/400,816, filed Aug. 2, 2002; U.S. Ser. No. 60/393,651, filed Jul. 3, 2002; and U.S. Ser. No. 60/393,428, filed Jul. 3, 2002. This application also claims priority to U.S. Ser. Nos. 60/590,848 and 60/590,751, filed Jul. 23, 2004. All of the above applications are incorporated herein by reference.

STATEMENT REGARDING FEDERALLY SPONSORED RESEARCH

The subject invention was made with government support under a research project supported by National Institutes of Health Grant No R 01 GM63879. The government has certain rights in this invention.

FIELD OF THE INVENTION

The field of this invention relates to genetically engineering a plant plastid. More specifically, this invention relates to the transformation of non-green plant cells through plastid transformation, and the subsequent regeneration of the non-green plant cells through somatic embryogenesis.

BACKGROUND

Plastids are ideal for genetic engineering because they offer a number of attractive advantages, including high-level transgene expression (Daniell et al., 2002), multi-gene engineering in a single transformation event (DeCosa et al., 2001; Ruiz et al., 2003; Daniell & Dhingra, 2002), transgene containment via maternal inheritance (Daniell 2002), lack of gene silencing (Lee et al., 2003; DeCosa et al., 2001), position effect due to site specific transgene integration (Daniell et al., 2002) and pleiotropic effects (Daniell et al., 2001; Lee et al., 2003). Chloroplast genetic engineering is most suitable for hyper-expression of vaccine antigens and production of valuable therapeutic proteins. Ever since we demonstrated expression of human-elastin derived polymers for various biomedical applications (Guda et al., 2000), we have extended this approach to express vaccine antigens for Cholera and Anthrax (Daniell et al., 2001, Daniell 2003), monoclonal antibodies (Daniell et al., 2001) and human therapeutic proteins, including Human Serum Albumin (Fernandez et al., 2003), Magainin (DeGray et al., 2001), Interferon (Daniell 2003) and Insulin-like Growth Factor (Daniell, 2003). Several other laboratories have expressed Human Somatotropin and Interferon-GUS fusion proteins to improve stability (Reddy et al., 2003) and tetanus vaccine antigens (Tregoning et al., 2003) in transgenic chloroplasts. Without any exception, all of these therapeutic proteins have been expressed in transgenic tobacco chloroplasts, meeting the zero-tolerance of food crops for plant-derived pharmaceuticals advocated by various environmental groups.

However, there is an urgent need for oral delivery of therapeutic proteins and vaccine antigens to dramatically reduce their production, purification, storage and transportation costs and minimize complications associated with intravenous delivery. Carrot (*Daucus carota* L.) is one of the most important vegetables used worldwide for human and animal consumption, due to its excellent source of sugars, vitamins A and C, and fiber in the diet. The carrot plant is biennial, completing its life cycle in two years. In the first year the plant produces the fleshy taproot, which is edible. If left in the ground, plants flower in the second year after passing through a cold season (Yan, W. & Hunt, L. A Reanalysis of Vernalization Data of Wheat and Carrot, *Annals of Botany* 84, 615-619 (1999)). In addition, chloroplast genomes in the cultivated carrot crop are transmitted strictly through maternal inheritance (Vivek et al. 1999). Thus, carrot is environmentally safe and is doubly protected against transgene flow via pollen and seeds to achieve zero-tolerance on transgene flow advocated for food crops. Carrot somatic embryos are single cell derived and multiply through recurrent embryogenesis; this provides a uniform source of cell culture, which is one of the essential requirements for producing therapeutic proteins (homogeneous single source of origin). Carrot cells divide rapidly and a large biomass is produced using bioreactors. Cultured carrot cells are edible and could be used directly to deliver precise doses of vaccine antigens or biopharmaceuticals. When delivered via edible carrots, there is no need to cook and this would preserve the structural integrity of therapeutic proteins during consumption. Viable for long duration on culture medium, encapsulated embryos are used as synthetic seeds for cryopreservation and controlled germination (Tessereau, H., B. Florin, M. C. Meschine, C. Thierry and V. Pétiard, 1994). Thus, transgenic carrot with enhanced medicinal or nutritional value can play a vital role in improving human or animal health.

However, there is a need for more efficient plastid transformation including an efficient process to transform important crop species which allows for the regeneration of transplastomic plants via somatic embryogenesis.

Table 1 shows an exemplary list of the development of transgene expression in chloroplasts.

TABLE 1

Transgene Expression in Chloroplasts

| Agronomic traits | Gene | Promoter | 5'/3' Regulatory elements | Reference |
|---|---|---|---|---|
| Insect resistance | Cry1A(c) | Prrn | rbcL/Trps16 | Mc Bride et al. 1995 |
| Herbicide resistance | CP4 (petunia) | Prrn | ggagg/TpsbA | Daniell et al. 1998 |
| Insect resistance | Cry2Aa2 | Prrn | ggagg (native)/TpsbA | Kota et al. 1999 |

TABLE 1-continued

Transgene Expression in Chloroplasts

| | | | | |
|---|---|---|---|---|
| Herbicide resistance | CP4 (bacterial or synthetic) | Prrn | rbcL or T7 gene 10/Trps16 | Ye at al 2001 |
| Insect resistance | Cry2Aa2 operon | Prrn | Native 5'UTRs/TpsbA | DeCosa et al. 2001 |
| Disease resistance | MSI-99 | Prrn | ggagg/TpsbA | DeGray et al. 2001 |
| Salt and drought tolerance | tps | Prrn | ggagg/TpsbA | Lee et al. 2003 |
| Phytoremediation | merA$^a$/merB$^b$ | Prrn | ggagg$^{a,b}$/TpsbA | Ruiz et al. 2003 |

| Biopharmaceutical proteins | Gene | Promoter | 5'/3' regulatory elements | % tsp expression | Reference |
|---|---|---|---|---|---|
| Protein based polymer | EG121 | Prrn | T7gene10/TpsbA | Not tested | Guda et al. 2000 |
| Human somatotropin | hST | Prrn$^a$, PpsbA$^b$ | T7gene10$^a$ or psbA$^b$/Trps16 | 7.0%$^a$ and 1.0%$^b$ | Staub et al. 2000 |
| Cholera toxin | ctxB | Prrn | ggagg/TpsbA | 4% | Daniell et al. 2002 |
| Tetanus toxin | TetC (bacterial and synthetic) | Prrn | T7 gene 10$^a$, atpB$^b$/TrbcL | 25%$^a$, 10%$^b$ | Tregoning et al. 2003 |
| Human Serum Albumin | hsa | Prrn$^a$, PpsbA$^b$ | ggagg$^a$, psbA$^b$/TpsbA | 0.02%$^a$, 11.1%$^b$ | Fernandez-San Milan et al. 2003 |
| Interferon alpha 5 | INFα5 | Prrn | PpsbA/TpsbA | ND | Torres |
| Interferon alpha 2B | INFα2B | Prrn | PpsbA/TpsbA | 19% | Falconer |
| Interferon gamma | ifn-g | PpsbA | PpsbA/TpsbA | 6% | Leelavathi and Reddy, 2003 |
| Monoclonal antibodies | | Prrn | ggagg/TpsbA | ND | Daniell et al. (photosynthesis) |
| Insulin like growth factor | Igf-1 | Prrn | PpsbA/TpsbA | 33% | Ruiz G |
| Anthrax protective antigen | Pag | Prrn | PpsbA/TpsbA | 4-5% | Watson |
| Plague vaccine | CaF1~LcrV | Prrn | PpsbA/TpsbA | 4.6% | Singleton |

SUMMARY OF THE INVENTION

Briefly, in accordance with the present invention, transformed plant plastids and regenerated fertile transplastomic plants obtained via somatic embryogenesis are made by a method that involves transforming a plant plastid in a plant cell capable of being regenerated through somatic embryogenesis with a plastid expression cassette comprising one or more selectable marker genes that express in both green and non-green tissue and in light and dark conditions wherein the selectable marker gene product provides resistance of the plant cell to a selection agent. The transplastomic plant cell is cultured in the presence of the selection agent under conditions to cause the formation of a somatic embryo. The somatic embryo is grown into a fertile transplastomic plant. Preferably the expression cassette contains two different selectable marker genes that express different proteins that provide plant cell resistance to the same selection agent. Suitable plant tissues that can be regenerated into a whole fertile plant via somatic embryogenesis include hypocotyls, stem segments, cotyledons, immature embryos and embryogenic cell cultures.

The present invention is also directed to plastid plant transformation vectors that include one or more selectable marker genes and control sequences functional in plastids wherein at least one of the control sequences is (i) active in non-green tissue and green tissue and (ii) active under light and dark conditions. DNA sequences homologous to the native plastid genome flank the selectable marker gene and control sequences to facilitate stable integration of the selectable marker genes and control sequences with plastid DNA making up the genome of the cell by homologous recombination, whereby the selectable marker gene and control sequences are stably integrated into the plastid genome and inherited through organelle replication in a daughter cell. Preferably, the plastid plant transformation vector includes two selectable marker genes. The selectable marker gene products of the two selectable marker genes are different from each other but provide resistance of the plant cell to the same selection agent.

Additionally, the present invention relates to transplastomic plant cells which contain one or more selectable marker genes and control sequences functional in plastids wherein at least one of the control sequences is (i) active in non-green tissue and green tissue and (ii) active under light and dark conditions so that at all times after the transformation event a selectable marker gene is expressing a gene product (protein) that makes the transformed plant cell resistant to the selection agent. Preferably, the transplastomic plant cells contain two selectable marker genes and the selectable marker gene products of the two selectable marker genes are different from each other but provide resistance of the plant cell to the same selection agent. Since the selectable marker genes are expressed in non-green tissues, green tissues, under light conditions and under dark conditions the plant cells are protected from the selection agent that is used in the post transformation culturing process. As the transplastomic plant cells are cultured the constant expression of the selectable marker gene provides the gene product that makes the transplastomic plant cells resistant to the selection agent and allows for the formation of somatic embryos. As the somatic embryos are formed they are typically isolated and regenerated into a whole fertile plant.

Suitable plants that can be transformed and regenerated via somatic embryogenesis according to the present invention include cereal crops (wheat, rice, corn, sugarcane), legumes (soybean, alfalfa), oil crops (sunflower, olive, Brassica sp.), cash crops (cotton, coffee, tea, rubber, flax, cork oak, pines), vegetables (eggplant, carrot, cucumber, cassava, chili pepper, asparagus, etc.), fruits (apple, cherry, banana, plantain, melons, grape, guava), nuts (cashew, walnuts, peanuts), and trees (date palm, etc.). Preferred crops include corn, cotton, rice, alfalfa, wheat, carrot and Brassica sp.

Of particular interest in practicing the present invention, a plastid transformation vector that contains two selectable marker genes wherein the selectable marker gene products of the two selectable marker genes are different from each other but provide resistance of the plant cell to the same selection agent. The control sequences in the vector are functional in plastids wherein at least one of the control sequences is (i) active in non-green tissue and green tissue and (ii) active under light and dark conditions. The control sequences then provide for constant expression of a selectable marker gene product which provides the plant cell continuous resistance to the corresponding selection agent. This continuous expression of the selectable marker gene allows for the use of non-green tissues that are the typical tissues that can be regenerated into plants via somatic embryogenesis. The plastid vector also contains flanking DNA sequences that are homologous to regions of the native plastid genome. The flanking DNA regions facilitate stable integration of the selectable marker genes and control sequences with plastid DNA making up the plastid genome of the cell by homologous recombination, whereby the selectable marker gene and control sequences are stably integrated into the plastid genome and inherited through organelle replication in a daughter cell. Preferably, selectable marker genes that provide resistant to aminoglycoside antibiotics are employed especially the aphA6 gene and the nptII gene (aphA2). Preferred control sequences include the t7 bacteriophage gene 10 ribosome binding site (also referred to as the gene 10 5' UTR), the psbA promoter and the Prrn promoter. Termination sequences are also employed such as the 3' psbA termination sequence.

BRIEF DESCRIPTION OF THE FIGURES

FIG. 1(A-B) shows the physical map of the carrot chloroplast transformation vectors.

FIG. 2(A-D) shows the expression of GFP in carrot cultures transformed with chloroplast vector pDD-Dc-gfp/BADH; visible under confocal fluorescent microscope at fluorescence emission in green at 488 nm blue Argon (laser).

FIG. 3(A-B) shows the transgenic carrot cell culture turned green due to the expression BADH (Plate A) while wild type culture remained yellow (Plate B). Transgenic carrot cell culture can be distinguished as green-transgenic cell culture vs yellow non-transgenic carrot cell culture, when heteroplasmic transgenic cell line was placed on medium without any selection agent (Plate C and D).

FIG. 4(A-C) shows the transgene (aadA and badh) integration into the carrot plastid genome was confirmed by PCR and Southern blot analysis.

FIG. 5(A-B) shows BADH enzyme activity (nmol/min/mg/protein) and BADH expression was analyzed in protein extracts from untransformed and transformed carrot with plastid vector pDD-Dc-aadA/BADH.

FIG. 6(A-C) shows the effect of different salt concentrations on growth of untransformed and transformed carrot cell suspension cultures with chloroplast vector pDD-Dc-aadA/BADH.

FIG. 6(A), part B shows transformed cell cultures produced in liquid medium containing 100 mM NaCl.

Figure 30:
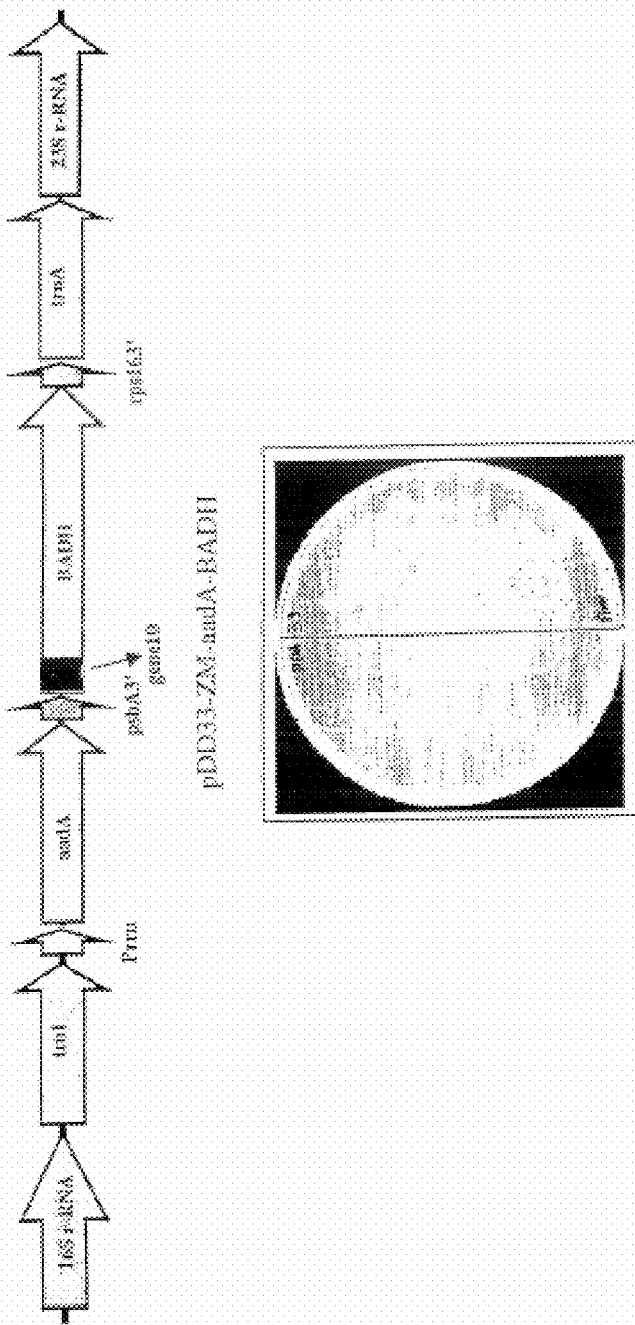

The upper portions of FIGS. 29 and 30 illustrate the construction of maize chloroplast transformation vector, where flanking regions were amplified using PCR. The PCR products were cloned and the expression cassette was inserted in the transcriptionally active spacer region between trnI/trnA genes. The expression cassette of FIG. 30A has the Prrn promoter driving the expression of GFP and BADH, which are regulated by (5') gene10/rps16 3' and psbA 5'/3' UTRs respectively. The expression cassette of 31A has the Prrn promoter driving the expression of aadA and BADH. The latter gene is regulated by (5') gene10/rps16 3' UTRs.

Figures 31A, 31B, 31C:

The lower portions of FIGS. 29 and 30 shows the functions of the genes in the maize chloroplast transformation vectors which were tested in *E. coli*. For observing GFP expression, cells were plated on LB agar (Amp) plates and incubated at 37° C. overnight. Cells harboring pDD34-ZM-GFP-BADH were seen to fluoresce when exposed to UV light, as is seen in FIG. 30B. To test the aadA gene expression, cells harboring pDD33-ZM-aadA-BADH plasmid were plated on LB agar plates containing spectinomycin (100 mg/ml) and incubated at 37° C. overnight. Transformed cells grow on spectinomycin, as can be seen in FIG. 31B.

Figure 32A:
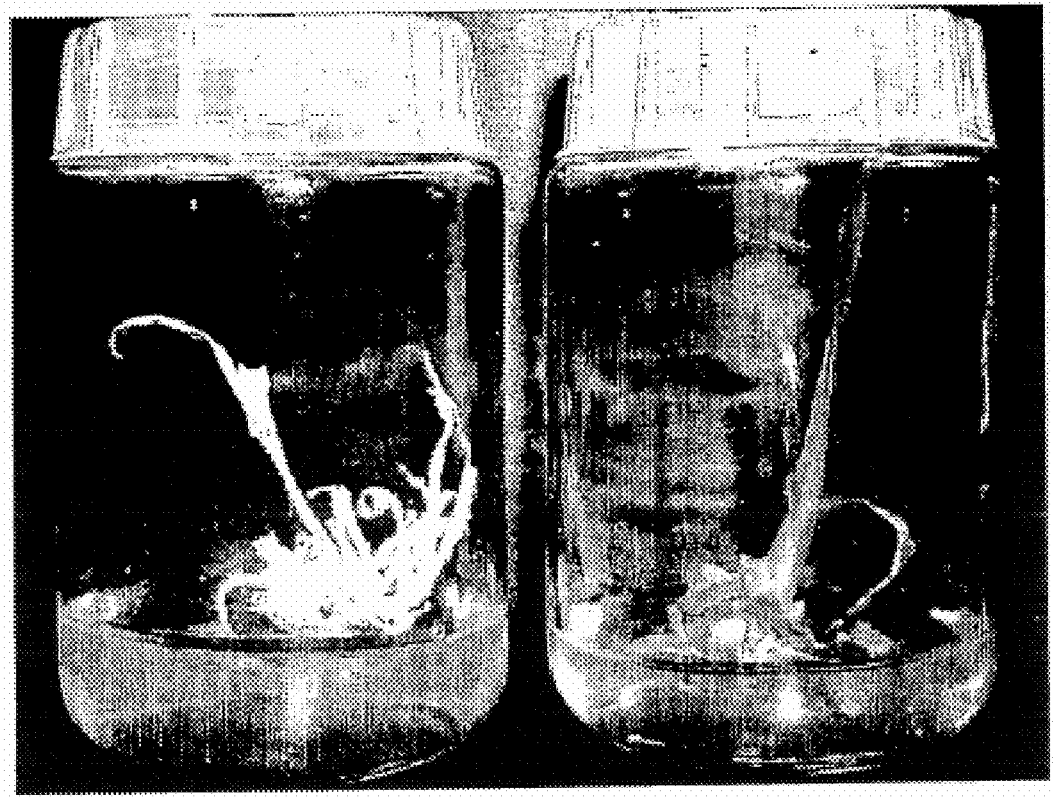
Figure 32B:
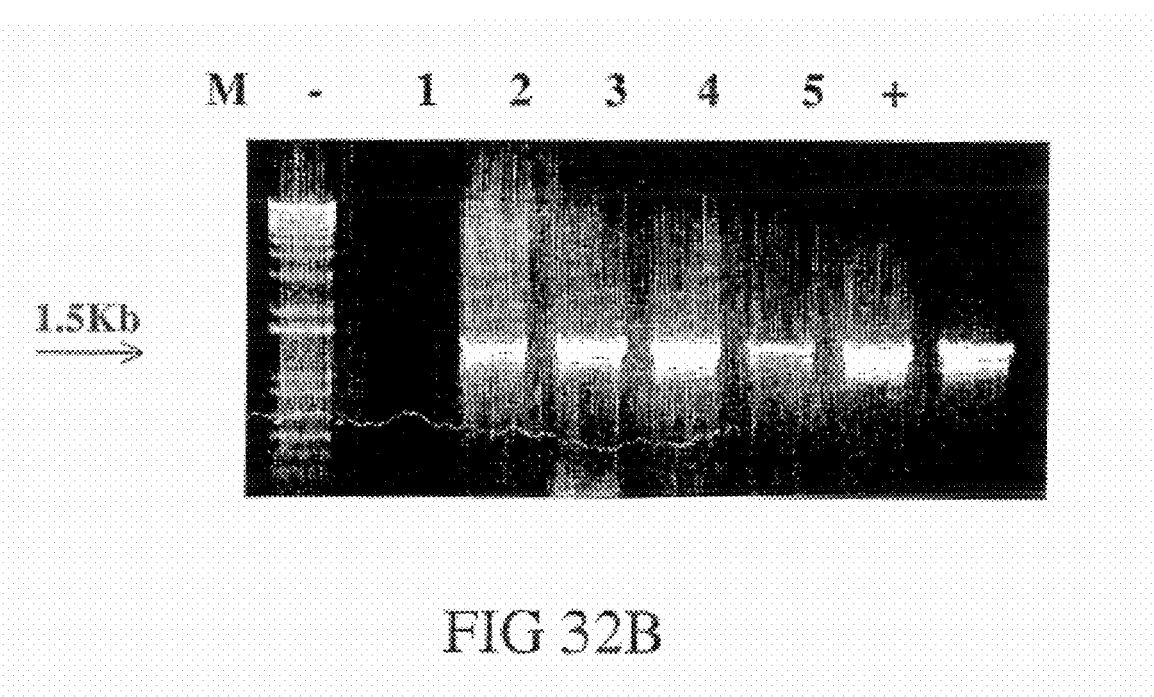

FIG. 31 shows GFP expression in embryogenic maize cultures studied under the confocal microscope. FIG. 32(A) is a non-transgenic control, while FIG. 32(B) are transformed maize embryogenic calli. The selection in FIGS. 30-31 was initiated two days after bombardment by transferring the bombarded calli to callus induction medium containing BA or streptomycin. After eight weeks, a number of the healthy growing calli from different bombardment experiments were examined for GFP expression under the fluorescent stereomicroscope and the confocal microscope. Somatic embryos were regenerated on maize regeneration medium containing BA or streptomycin.

FIG. 32(A-B) shows maize plants on regeneration medium containing streptomycin or betaine aldehyde.

FIG. 32(A) illustrates maize chloroplast transgenic plants which were capable of growth on the selection agent indicating that construction of transgenic maize, while untransformed maize plants did not grow on the selection medium.

FIG. 32(B) shows PCR confirmation of chloroplast transgenic plants using appropriate primers. Lanes 1-3, plants transformed with pDD34-ZM-gfp-BADH and Lanes 4-5, plants transformed with pDD33-ZM-aadA-BADH. Lanes – and + represent the negative and positive controls respectively. Genomic DNA was isolated from the leaf tissues and PCR was performed on transformed and non-transformed tissues using appropriate primers.

FIG. 33(A-C) shows the Transformed cotton cultures (*Gossypium hirsutum* cv. Coker310FR) with chloroplast vector pDD-C-aphA6/aphA2; selected on medium MST1 (0.1 mg/l 2,4-D and 0.5 mg/l kinetin) supplemented with 50 mg/l kanamycin.

Figures 33A, 33B, 33C:
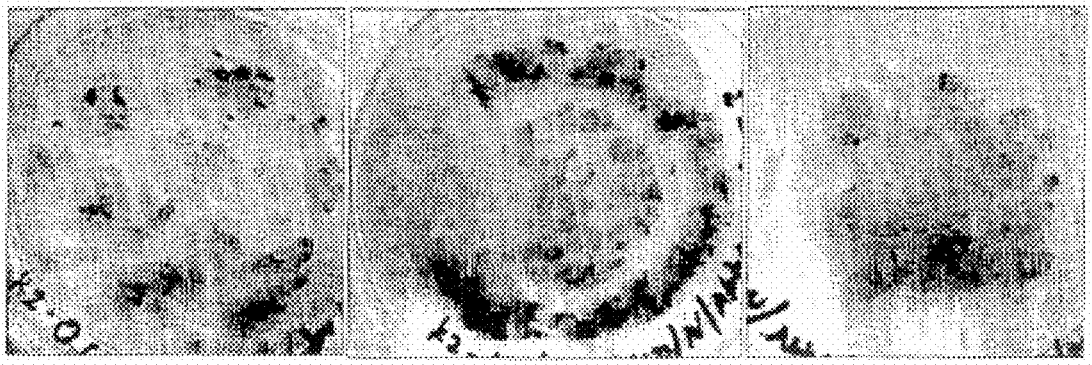

FIG. 33(A) shows the untransformed control cotton calli, FIG. 33(B) shows the transformed primary cotton calli, and FIG. 33(C) shows the transformed cotton calli subcultured from transgenic primary cotton calli (Plate B).

FIG. 34(A-B) show the transgene (aphA6 and aphA2) integration into the cotton plastid genome was confirmed by PCR.

FIG. 34(A) shows the use of internal primers 3P (land on flanking sequence) and aphA6-rev (land on aphA6 gene) ~1.7 kb size PCR product was amplified at 64° C. annealing temperature, confirmed transgene integration into cotton calli.

FIG. 34(B) shows the use of a set of primer 16SF (landing on the native chloroplast genome) and aphA6-rev (landing on the aphA6 gene) yield ~2.5 kb size PCR product at 64° C. annealing temperature, confirmed plastid specific integration of the transgenes. Lane 1 represents the 1 kb Plus molecular marker (ladder). Lane 2 stand for DNA from non-transgenic cotton calli and lane 3 represents DNA from transgenic cotton calli selected on 50 mg/l kanamycin.

Figure 35:
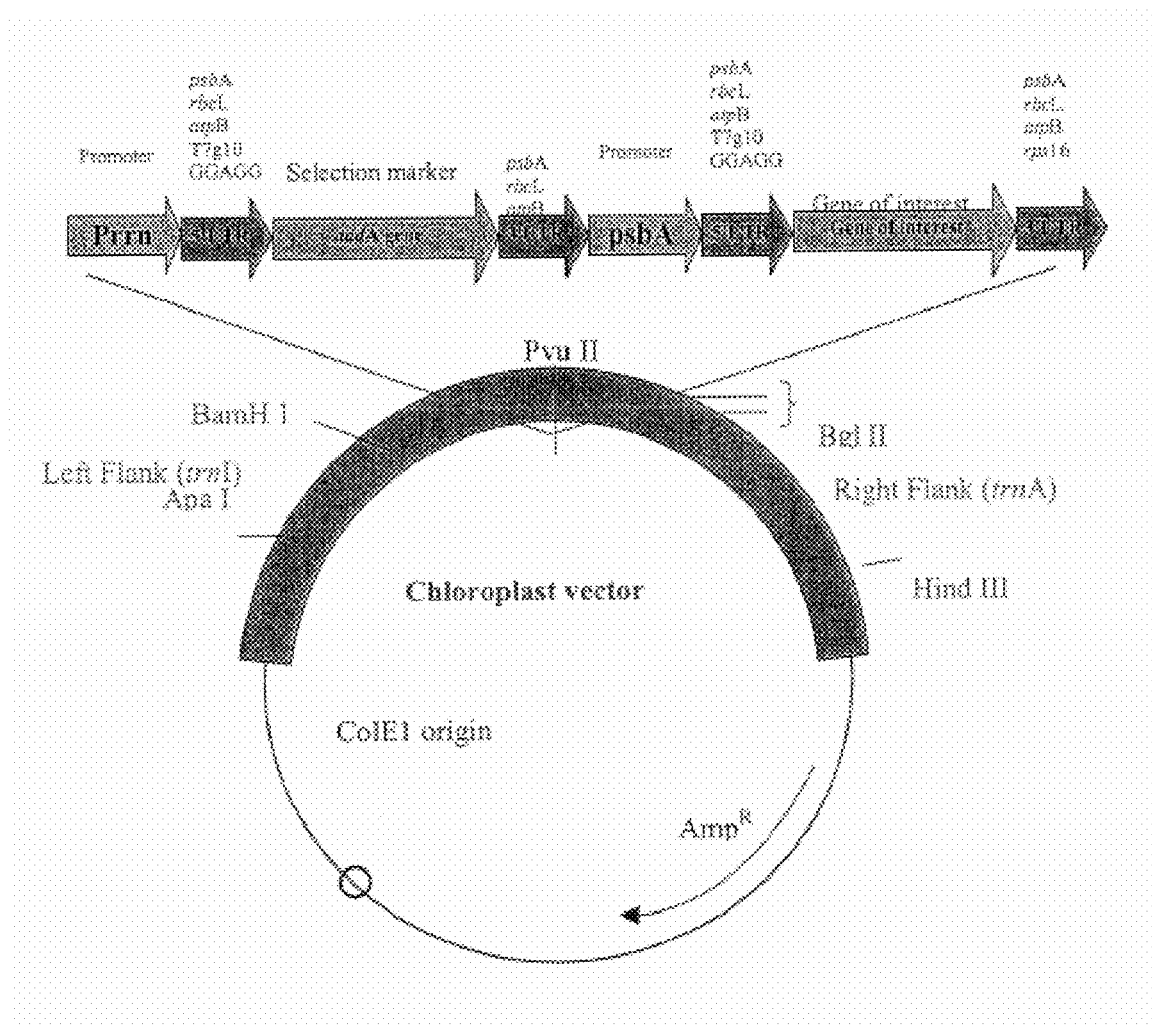

FIG. 35 shows a schematic view of a general plastid transformation vector.

Figures 36A, 36B:
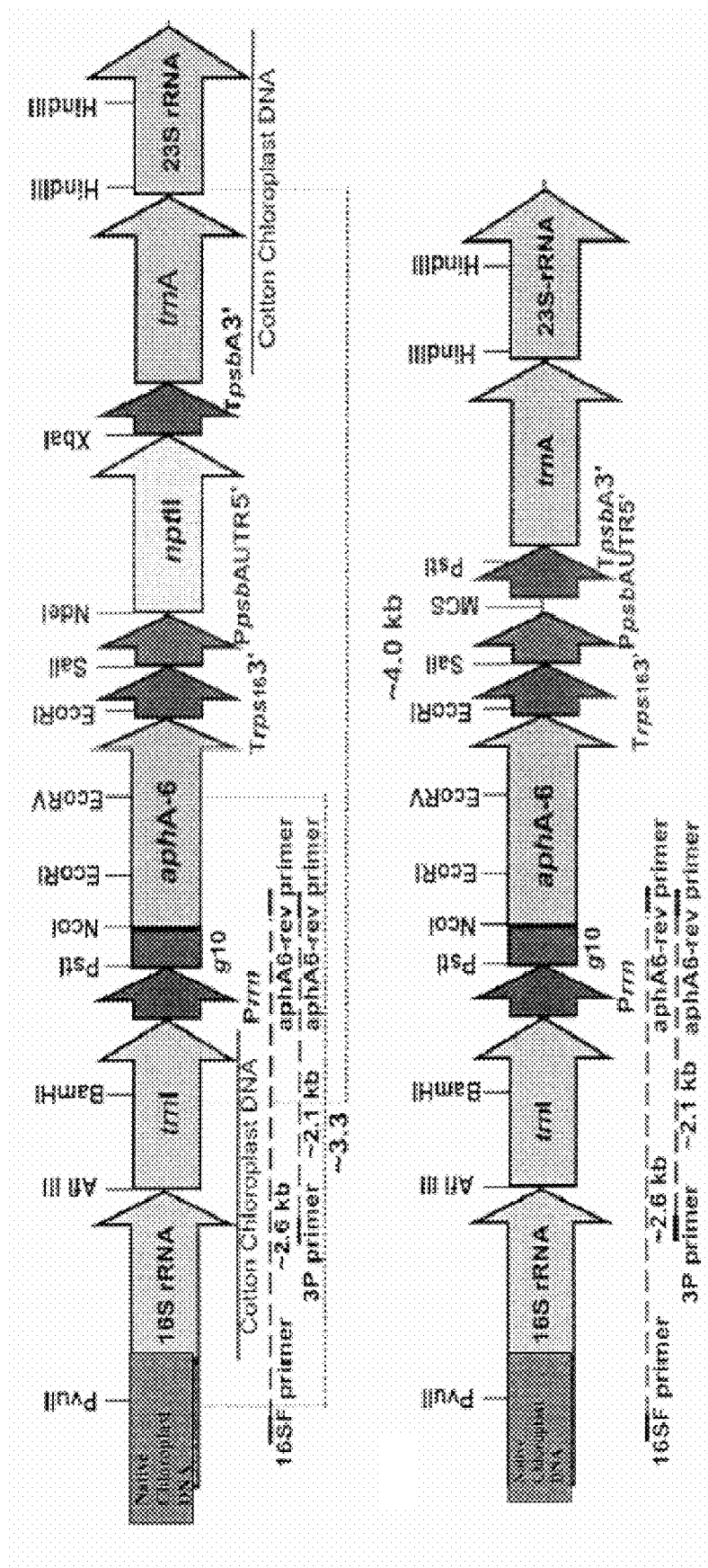

FIGS. 36A and 36B show physical maps of the cotton chloroplast transformation vectors. FIGS. 36A shows cotton chloroplast transformation vector pDD-Gh-aphA6/nptII with double selection marker genes aphA-6 and nptII. Primer annealing sites and probe used for Southern analysis are shown. FIGS. 36B shows cotton chloroplast transformation vector pKD -Gh-aphA6 with a single selection marker aphA-6 gene.

FIG. 37 is a Table showing cotton calli (8-10 weeks old) bombarded with the vector pDD-Gh-aphA-6/nptII and pKD-Gh-aphA-6, coated on 0.6 lm gold particles using indicated parameters. The transgenic cell lines selected on MST1 medium containing 50 mg/l kanamycin after bombardments were confirmed by PCR for site-specific transgene integration.

Figure 38:
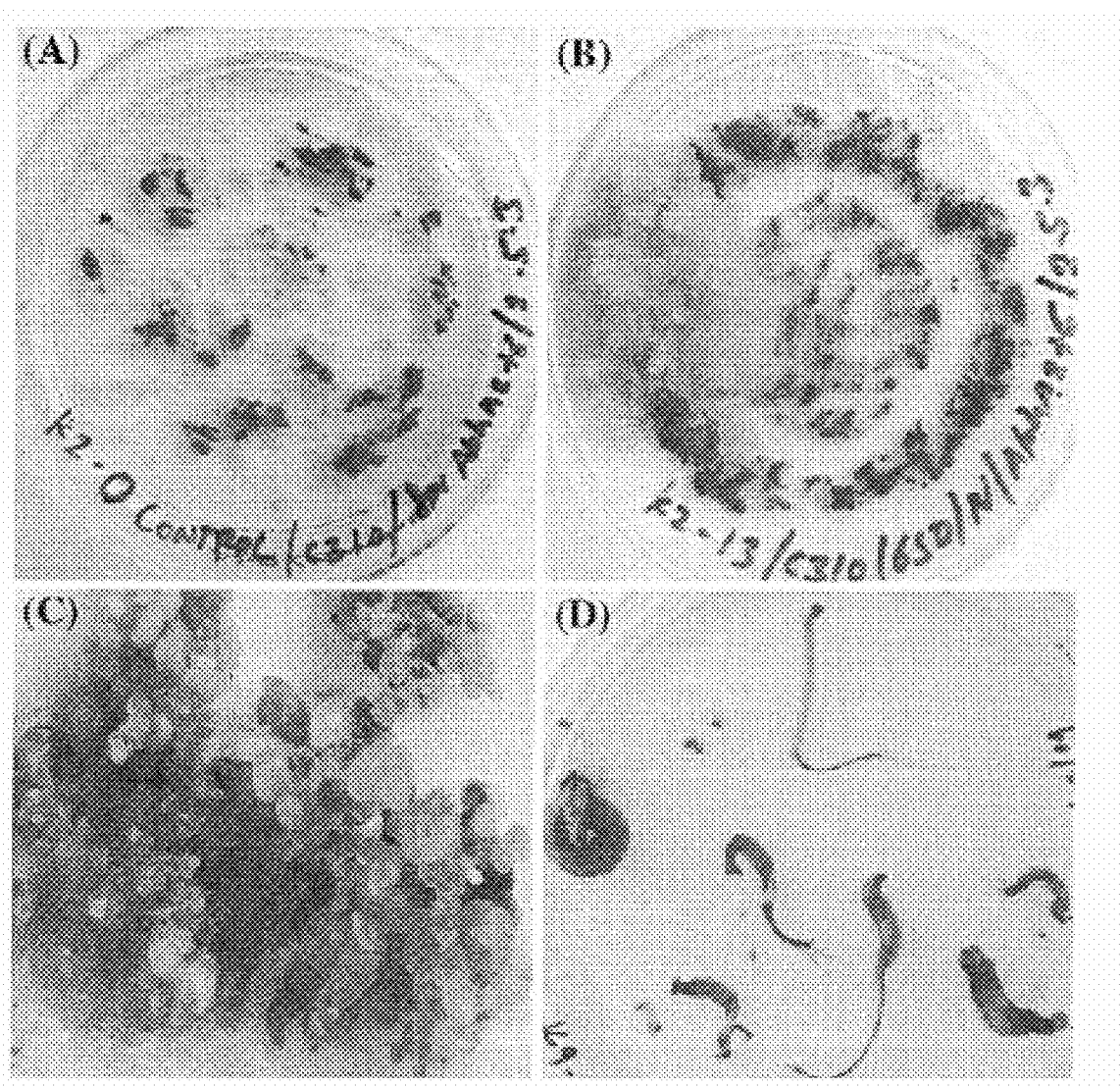

FIGS. 38A-38D shows cotton calli transformed with chloroplast transformation vector PDD-Gh-aphA6/nptII. FIG. 38A shows untransformed control cotton calli and FIG. 38B shows transformed primary cotton calli selected on MST1 medium supplemented with 50 mg/l kanamycin. FIG. 38D shows transgenic elongated somatic embryos that were used to induce homoplasmy by initiating fresh callus from their hypocotyls segments.

Figure 39:
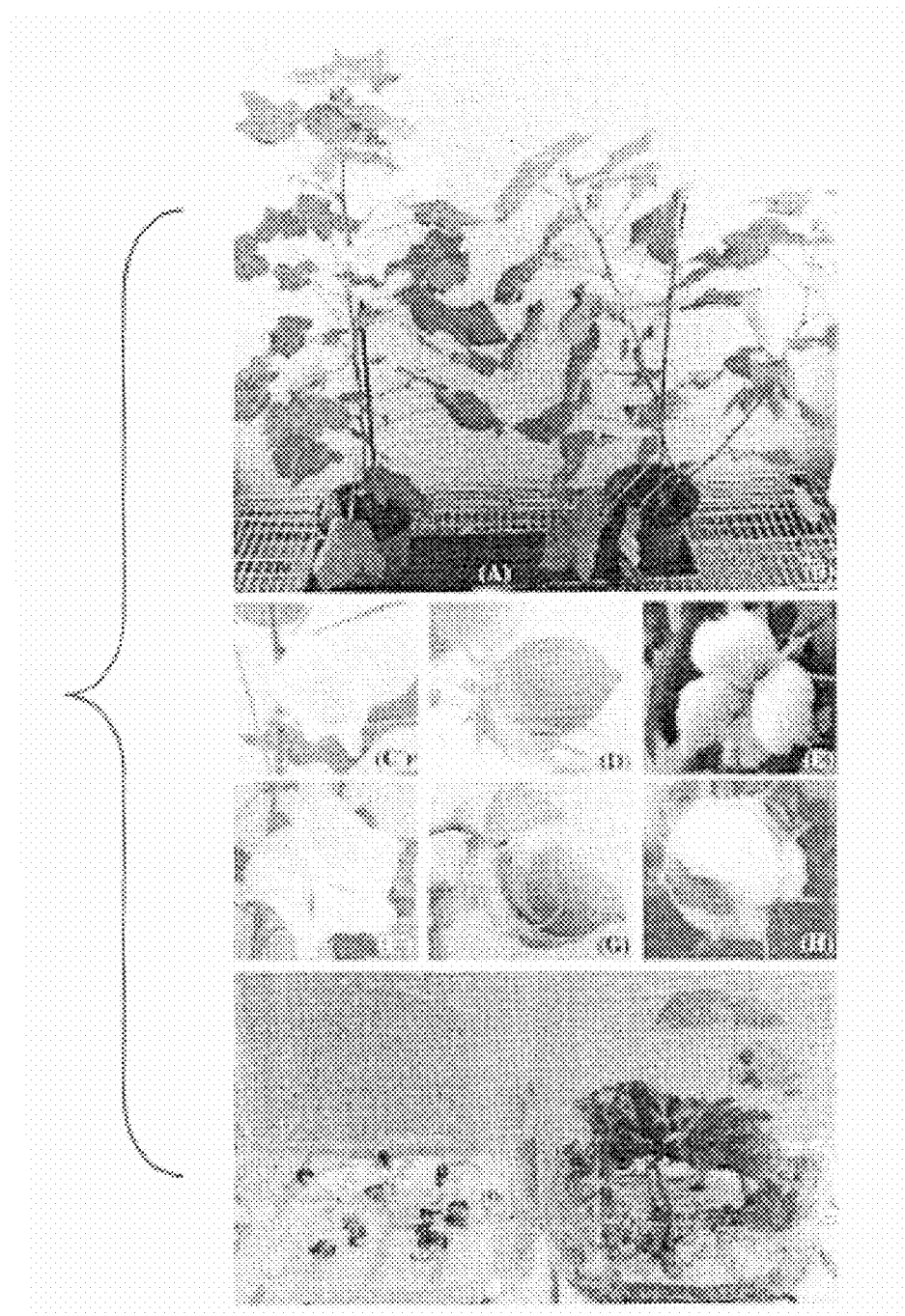

FIG. 39 shows transgenic (A) and non-transgenic (b) control cotton plants at the stage of flowering and seed setting, different floral parts of transgenic cotton (C-E) and nontransgenic control cotton (F-G).

DETAILED DESCRIPTION OF THE INVENTION

In one aspect of the invention homoplasmic plants regenerated from the plant cell culture via somatic embryogenesis is provided. Another aspect of this invention is plastid transformation vectors capable for use in non-green explants which can lead to somatic embryogenesis of the plant cells. Yet another aspect of this invention provides for transgene expression in non-green edible plant parts. Aspects of this invention further describe transformation of monocots, legumes, vegetables, fruit crops, and transgene expression within the non-green plant parts of these plants and cell cultures derived therefrom. Another aspect of this invention provides for the expression of heterologous proteins using a plastid transformation vector suitable for transforming the non-green plant parts. In other aspects are methods of transforming plastid genomes to express heterologous proteins in transformed plants and progeny thereof. Yet another aspect of this invention is the introduction of foreign DNA into the small proplastids of plants, and the identification of selectable markers and control sequences which function in non-green plastids. Still other aspects of this invention provide for regenerated chloroplast transgenic plants via somatic embryogenesis to achieve homoplasmy.

The preferred aspects of this application are applicable to all plastids of higher plants. These plastids include the chromoplasts, which are present in the fruits, vegetables, and flowers; amyloplasts, which are present in tubers such as potato; proplastids in the roots of higher plants and young non-green tissues of a developing plant; leucoplasts and etioplasts (which express in the dark), both of which are present in the non-green parts of plants. The aspects of this application are also applicable to various developmental stages of chloroplast, wherein the chloroplast are not fully green.

Definitions

To better understand the current disclosure, the following definitions, which shall hold their meaning throughout this application unless otherwise noted, are provided to put the application in proper context.

"Heterologous" generally means derived from a separate genetic source. Of course this invention contemplates the use of heterologous and homologous DNA, as well as operons suitable for expression in plant plastids.

An "expression cassette" is generally understood in the art as a cloning vector that contains the necessary regulatory sequences to allow transcription and translation of a cloned gene or genes.

"Properly folded" should be understood to mean a protein that is folded into its normal conformational configuration, which is consistent with how the protein folds as a naturally occurring protein expressed in its native host cell.

When referring to plants throughout the application, it should be understood that the present invention contemplates the transformation of the plastids of all organisms and plants which contain plastids. For purposes of clarity the phrase "higher plants" generally includes *Solanaceous* and non-*Solanaceous* plants, and the exemplary list of crops, fruits, flowers, vegetables, beans, medicinal plants, and all other plants which one skilled in the art would recognize as being a higher plant.

By "substantially homologous," as used throughout the ensuing specification and claims, is meant a degree of homology to a native protein sequence in excess of 50%, most preferably in excess of 80%, and even more preferably in excess of 90%, 95% or 99%. "Substantial sequence identity" or "substantial homology," as used herein, are used to indicate that a nucleotide sequence or an amino acid sequence exhibits substantial structural or functional equivalence with another nucleotide or amino acid sequence. Any structural or functional differences between sequences having substantial sequence identity or substantial homology will be de minimis; that is, they will not affect the ability of the sequence to function as indicated in the desired application. Differences may be due to inherent variations in codon usage among different species, for example. Structural differences are considered de minimis if there is a significant amount of sequence overlap or similarity between two or more different sequences or if the different sequences exhibit similar physical characteristics even if the sequences differ in length or structure. Such characteristics include the ability to maintain expression and properly fold into the protein's conformational native state, hybridize under defined conditions, demonstrate a well defined immunological cross-reactivity, or exhibit similar biopharmaceutical activity, etc. Each of these characteristics can readily be determined by the skilled practitioner in the art using known methods.

"Non-green plastids" generally refers to any plastid that is not green. Examples of such plastids include the chromoplasts, which are present in the fruits, vegetables, and flowers; amyloplasts, which are present in tubers such as potato; proplastids in the roots of higher plants and the tissues of a germinating plant such as hypocotyls tissue, cotyledon stem segments, etc; leucoplasts and etioplasts (which express in the dark); and different development stages of chloroplast, wherein the chloroplast is not green. Further, the non-green parts of plants and plant cells are well characterized and understood in the art.

"Spacer region" is understood in the art to be the region between two genes. The chloroplast genome of plants contains spacer regions which have highly conserved nucleotide sequences. The highly conserved nature of the nucleotide sequences of these spacer regions in the chloroplast genome makes the spacer regions ideal for construction of vectors to transform the chloroplasts of a wide variety of plant species, without the necessity of constructing individual vectors for different plants or individual crop species. It is well understood in the art that the sequences flanking functional genes are well-known to be called "spacer regions." The special features of spacer regions are clearly described in the Applicant's application Ser. No. 09/079,640 with a filing date of May 15, 1998 and entitled UNIVERSAL CHLOROPLAST INTEGRATION OF EXPRESSION VECTORS, TRANSFORMED PLANTS AND PRODUCTS THEREOF. The aforementioned application Ser. No. 09/079,640 is hereby incorporated by reference. It was well-known that there are at least sixty transcriptionally-active spacer regions within the higher plant chloroplast genomes (Sugita, M., Sugiura, M., Regulation of Gene Expression in (chloroplasts of Higher Plants, *Plant Mol. Biol.*, 32:315-326, 1996). Specifically, Sugita et al. reported sixty transcriptionally-active spacer regions referred to as transcription units, as can be seen in Table II of the article. Because the transcriptionally active spacer regions are known, a universal vector, as described in the Applicant's U.S. patent application Ser. No. 09/079,640, can be used in the identified spacer regions contained within a variety of the higher plant chloroplast genomes. By utilizing the teachings in Sugita et al., intergenic spacer regions are easily located in the plastid genome. Consequently, this allows one skilled in the art to use the methods taught in the Applicant's U.S. patent application Ser. No. 09/079,640 to insert a universal vector containing the psbA, the 5' untranslated region (UTR) of psbA and the gene coding for the protein of interest into the spacer regions identified by Sugita et al., and found across higher plants. The aforementioned applications and article are incorporated by reference.

"Selectable marker" provides a means of selecting the desired plant cells. Vectors for plastid transformation typically contain a construct which provides for expression of a selectable marker gene. Marker genes are plant-expressible DNA sequences which express a polypeptide which resists a natural inhibition by, attenuates, or inactivates a selective substance, i.e., antibiotic, herbicide, or an aldehyde dehydrogenase such as Betaine aldehyde dehydrogenase (described in the Applicant's application Ser. No. 09/807,722 filed on Apr. 18, 2001, and herein fully incorporated by reference). Alternatively, a selectable marker (reporter) gene may provide some other visibly reactive response, i.e., may cause a distinctive appearance or growth pattern relative to plants or plant cells not expressing the selectable marker gene in the presence of some substance, either as applied directly to the plant or plant cells or as present in the plant or plant cell growth media. These visual selectable marker genes are called "reporter genes." Reporter genes include GUS and GFP.

In either case, the plants or plant cells containing such selectable marker genes will have a distinctive phenotype for purposes of identification, i.e., they will be distinguishable from non-transformed cells. The characteristic phenotype allows the identification of cells, cell groups, tissues, organs, plant parts, or whole plants containing the marker gene. Detection of the marker phenotype makes possible the selection of cells having a second gene to which the marker gene has been linked.

The use of such a marker for identification of plant cells containing a plastid construct has been described in the literature. In the examples provided below, a bacterial aadA gene is expressed as the marker. Expression of the aadA gene confers resistance to spectinomycin and streptomycin, and thus allows for the identification of plant cells expressing this marker. The aadA gene product allows for continued growth and greening of cells whose chloroplasts comprise the selectable marker gene product. Other promoters may also be used to drive expression of the selectable marker gene, including various plastid promoters and bacterial promoters which have been shown to function in plant plastids. Additionally, the aminoglycoside selectable marker genes—the aphA6 gene and the aphA2 (nptII) gene—provide plant cells resistance to aminoglycoside antibiotics and in particular kanamycin. The aphA6 and aphA2 genes produce different proteins that provide the selection to the same selection agent.

"Inverted Repeat Regions" are regions of homology which are present in the inverted repeat regions of the plastid genome (known as IRA and IRB). Two copies of the transgene are expected per transformed plastid. Where the regions of homology are present outside the inverted repeat regions of the plastid genome, one copy of the transgene is expected per transformed plastid.

"Structural equivalent" should generally be understood to mean a protein maintaining the conformational structure of the native protein expressed in its natural cell.

"Transplastomic plant or transplastomic plant cell" means any plant or plant cell that has exogenous DNA inserted into the plastid genome by a transformation process.

In practicing the present invention, transformed plant plastids and regenerated fertile transplastomic plants obtained via somatic embryogenesis are made by transforming a plant plastid in a plant cell capable of being regenerated through somatic embryogenesis with a plastid expression cassette comprising one or more selectable marker genes that express the selectable marker gene product in both green and non-green tissue and in light and dark conditions wherein the selectable marker gene product provides resistance of the plant cell to a selection agent. The transplastomic plant cell is cultured in the presence of the selection agent under conditions to cause the formation of a somatic embryo. The somatic embryo is grown into a fertile transplastomic plant. Preferably the expression cassette contains two different selectable marker genes that express different proteins that provide plant cell resistance to the same selection agent. Suitable plant tissues that can be regenerated into a whole fertile plant via somatic embryogenesis include hypocotyls, stem segments, cotyledons, immature embryos, embryogenic cell cultures and the like.

The present plastid plant transformation vectors include one or more selectable marker genes, control sequences functional in plastids wherein at least one of the control sequences is (i) active in non-green tissue and green tissue and (ii) active under light and dark conditions. These active control sequences cause expression of the selectable marker gene to provide continuous resistance to the selection agent. This allows cells containing transformed plastids to grow and increase the number of plastids in the cell leading to a homoplasmic state. DNA sequences homologous to the native plastid genome flank the selectable marker gene and control sequences to facilitate stable integration of the selectable marker genes and control sequences with plastid DNA making up the genome of the cell by homologous recombination, whereby the selectable marker gene and control sequences are stably integrated into the plastid genome and inherited through organelle replication in a daughter cell. Preferably, the plastid plant transformation vector includes two selectable marker genes. The selectable marker gene products of the two selectable marker genes are different from each other but provide resistance of the plant cell to the same selection agent.

Vectors

The current application contemplates the use of vectors capable of plastid transformation. Such vectors include plastid expression vectors such as pUC, pBR322, pBLUESCRIPT, pGEM, and all others identified by Daniel in U.S. Pat. No. 5,693,507 and U.S. Pat. No. 5,932,479. Included are also vectors whose flanking sequences are located outside of the embroidered repeat of the chloroplast genome. These patents are hereby incorporated herein by reference.

The universal vector is described in WO 99/10513, which was published on Mar. 4, 1999, and application Ser. No. 09/079,640, which was filed on May 15, 1998, wherein both of said references are incorporated herein in their entirety.

Basic pLD vector, developed in this laboratory for chloroplast transformation, was used (Daniell et al., 1998; Daniell et al., 2001b; De Cosa et al., 2001; Guda et al., 2000; Kota et al., 1999). High levels of foreign protein expression in chloroplasts (3-21% of tsp) have been shown for different proteins using the SD 5' sequence (Daniell et al., 2001b; DeGray et al., 2001; Kota et al., 1999).

It should be noted that the vectors described herein are illustrative examples and vectors can be constructed with different promoters such as was described in U.S. patent application Ser. No. 09/079,640, different selectable markers such as those described in U.S. patent application Ser. No. 09/807,722, and different flanking sequences suitable for integration into a variety of plant plastid genomes. Each of the above-referenced applications is incorporated herein by reference.

In one embodiment of the present invention a Prrn promoter in combination with the T7 bacteriophage gene 10 ribosome binding site is used to express a selectable marker such as for example the aadA gene which confers resistance to antibiotics spectinomycin and streptomycin. In this embodiment a single selectable marker gene is employed with control sequences that cause expression of the aadA gene to continuously produce the aadA gene product and impart resistance of the transplastomic cells to spectinomycin and streptomycin. This allows for the growth and selection of the transplastomic cells in cell culture where eventually somatic embryos will be formed. The somatic embryos are then grown into transplastomic plants.

In another embodiment a selectable marker gene is controlled by the psbA promoter and the psbA 3' termination sequence. This embodiment provides strong gene expression under light conditions but weaker expression in non-green tissues and in the dark.

In a preferred embodiment of the present invention, the plastid transformation vector that contains two selectable marker genes. The selectable marker gene products of the two selectable marker genes are different from each other but provide resistance of the plant cell to the same selection agent. The control sequences in the vector are functional in plastids wherein at least one of the control sequences is (i) active in non-green tissue and green tissue and (ii) active under light and dark conditions. The control sequences then provide for constant expression of a selectable marker gene product which provides the plant cell continuous resistance to the corresponding selection agent. This continuous expression of the selectable marker gene allows for the use of non-green tissues that are the typical tissues that can be regenerated into plants via somatic embryogenesis. The plastid vector also contains flanking DNA sequences that are homologous to regions of the native plastid genome. The flanking DNA regions facilitate stable integration of the selectable marker genes and control sequences into the plastid genome of the cell by homologous recombination, whereby the selectable marker gene and control sequences are stably integrated into the plastid genome and inherited through organelle replication in a daughter cell. Preferably, the selectable marker genes provide resistance to aminoglycoside antibiotics. Especially preferred selectable marker genes include the aphA6 gene and the nptII gene (aphA2). Preferred control sequences include the t7 bacteriophage gene 10 ribosome binding site (also referred to as the gene 10 5' UTR), the psbA promoter and the Prrn promoter. The gene 10 RBS can be used alone or in combination with a promoter such as the Prrn promoter.

The transformation, cell culture, regeneration and molecular biology techniques used in practicing the present invention are all well-known to one of ordinary skill in the art.

One aspect of this invention describes methods for transforming plastids using a highly efficient process for carrot plastid transformation through somatic embryogenesis. Still other aspects of this invention provide for vectors which are capable plastid transformation through somatic embryogenesis. Still another aspect provides for transformed plastids, plants, and plant parts, which have been transformed through somatic embryogenesis through the methods and vectors described herein. This application, along with the knowledge of the art, provides the necessary guidance and instructions to engineer the plastid genome of several major crops in which regeneration is mediated through somatic embryogenesis. Cereal crops (wheat, rice, corn, sugarcane), legumes (soybean, alfalfa), oil crops (sunflower, olive, Brasica sp.), cash crops (cotton, coffee, tea, rubber, flax, cork oak, pines), vegetables (eggplant, cucumber, cassaya, chili pepper, asparagus etc.), fruits (apple, cherry, banana, plantain, melons, grape, guava), nuts (cashews, walnuts, peanuts), and trees (date palm etc.) are regenerated through somatic embryogenesis employing routine procedures well know to one of ordinary skill in the art.

In accordance with the present invention, stable transgene integration was confirmed in seven transgenic cell lines of carrot within 8-10 weeks from five bombardments and homoplasmy was achieved in cell cultures by repetitive 8-10 weekly subcultures in liquid medium. Carrot transgenic plants (ready to go in pots) were generated within a month from homoplasmic cell lines.

Another significant observation of the present invention is high levels of transgene expression in proplastids of cultured carrot cells. Sidorov et al. reported 50-fold less GFP accumulation in amyloplasts of potato tubers compared to leaves. In sharp contrast we report 53% BADH activity observed in carrot tap root cells compared to leaves. The heterologous gene 10 5' UTR that regulates translation of badh gene was indeed promoterless however, a promoter such as the Prrn promoter could also be used in conjunction with the gene 10 5' UTR. Chloroplast psbA 3' UTR is known to stabilize transcripts and is poor in transcription termination, with 30% termination efficiency. However, if higher levels of expression are desired in proplastids (such as corn seeds or in roots for nematode resistance), it may be desirable to insert a promoter upstream of gene 10 5' UTR to enhance transcription.

In order to achieve homoplasmy in a carrot system, several rounds of selection (8-10) were required along with high selection pressure. In liquid culture, all surfaces of carrot cells are directly exposed to the growth medium. This implies a high selection pressure, which might possibly block the growth of untransformed plastids. Carrot cells in liquid medium multiply fast compared to solid medium containing 2,4-D. Once 2,4-D is removed from the carrot cells, they rapidly convert into mature somatic embryos and profusely give rise to plantlets. Yet another requirement to achieve homoplasmy is the availability of templates for integration into thousands of plastid genomes per cell. We have previously shown that the use of chloroplast flanking sequence that contain the complete chloroplast origin of replication offers large number of templates within chloroplasts (Daniell et al., 1990) and helps to achieve homoplasmy even in the first round of selection (Guda et al., 2000). Inclusion of the chloroplast origin of replication within the carrot chloroplast vectors (assuming that the ori is present in the same location as in other plant species) should have helped achieve homoplasmy within a few rounds of cell division.

Carrot cells have a great potential for rapid proliferation through somatic embryos, which produce secondary somatic embryos (recurrent embryogenesis) until exposed to maturation medium for conversion into plants, and this culture can be maintained for several years in in vitro culture. In *Daucus carota* L. cv. US-Harumakigosun, embryogenic carrot calli maintained on suitable growth medium for a five year period produced a large number of plants ($4 \times 10^7$ plantlets/L-medium/day) continuously for 245 days without any decrease in the productivity (Nagamori et al. 1999) through liquid cell culture using a rotating bioreactor. Another advantage with somatic embryos is that they can be used as synthetic seeds. Synthetic or artificial seeds have been defined as somatic embryos encapsulated in sodium aliginate beads or matrix for use in the commercial propagation of plants. For example, carrot somatic embryos encapsulated in alginate-gellan gum (dehydrated to 15% RH and rehydrated in moistured air to 90% RH) germinated up to 73% in soil (Timbert et al. 1996) and the frequency of immobilized cell regeneration was improved about 1.5 times higher than that obtained through non-immobilized cells (Nagamori et al. 1999). With synthetic seed technology, desirable elite genotypes in carrot and other plant species can be cryopreserved for a long time (Tessereau et al. 1994) and on demand these propagules can be used for synchronized planting of plants in the greenhouse or field. A single source for production is highly desired to minimize heterogeneity of therapeutic proteins.

Glycine betaine (GB) is a commonly occurring compound in all living organisms and studies suggests that many higher plants, bacteria, marine and mammalian species accumulate GB under water deficiency or salt stress. In plants, bacteria and in mammalian kidney tissues, GB acts as an osmoprotectant. In porcine kidney, BADH is localized in the cortex and in the inner medulla, which is specifically localized on cells surrounding the tubules that are exposed to urea and high salt compounds (Figueroa-Soto et al. 1999). Glycine betaine is one of the major compatible organic osmolytes identified in renal inner medulla of rats, which helps renal cells to survive and function normally, despite being exposed to hypertonicity and lethal levels of urea.

These facts suggest that the presence of the BADH enzyme or accumulation of GB would be beneficial in foods consumed by humans or animals. In plants, salinity stress is a continuing and increasingly deleterious to the growth and yield of crop plants, owing to irrigation practices and increasing demands on fresh water supply; therefore, engineering of salt-tolerant crop plants has been a long-held and intensively sought objective (Apse, M. P., and Blumwald, E., 2002). One effective mechanism to reduce damage from these stresses is the accumulation of high intracellular levels of osmoprotectant compounds like glycine betaine in plants through genetic engineering (Rontein et al. 2002).

Of note, a potential vector for use is the double barrel plastid vector as described in U.S. Patent Application No. PCT/US02/41503, filed Dec. 26, 2002. The entirety of that application is incorporated herein by reference, but for purposes of simplicity we have included particular passages which describe the chloroplast double barrel vector. See Example 5 below. The description provided below will help in the understanding of the plasmids shown in FIG. 9-28 of this Application.

The following examples illustrate the practice of the present invention but should not be construed as limiting its scope.

ILLUSTRATIVE EXAMPLE 1

Somatic Embryogenesis Via Carrot Transformation

Homoplasmic transgenic carrot plants exhibiting high levels of salt tolerance (up to 500 mM NaCl) were rapidly regenerated from carrot cell cultures, via somatic embryogenesis. The carrot chloroplast genome is strictly maternally inherited and plants do not produce seeds in the first year, offering complete containment of transgene flow. Carrot cells multiply rapidly and a large biomass is produced using bioreactors; somatic embryos are derived from single cells. Viable for long duration on culture medium, encapsulated embryos are used as synthetic seeds for cryopreservation and controlled germination. These features provide an ideal production system for plant made pharmaceutical proteins and their oral delivery. BADH expressing cells offer a visual selection by their green color, distinguishing them from untransformed yellow cells.

This Example discloses stable and highly efficient plastid transformation of carrot using non-green tissues as explants, regenerated via somatic embryogenesis. In addition, expression of the BADH enzyme facilitated the visual selection of transgenic green cells from non-transgenic yellow cells. As a major crop consumed world-wide, the present invention serves as a model for genetic engineering of plastid genomes in higher plant species that require the use of non-green tissues as explants and somatic embryogenesis for regeneration.

Results and Discussion.

Construction of Carrot Plastid Transformation Vectors.

Carrot chloroplast vectors target the expression cassette to the 16S/trnI-trnA/23S region of the chloroplast genome for integration via homologous recombination. The site of integration is similar to the universal chloroplast transformation vector (pLD) reported earlier from our laboratory (Daniell et al., 1998; Guda et al., 2000) but the size of the flanking sequence on either side of the expression cassette was doubled to enhance efficiency of homologous recombination. As a result the flanking sequences were increased to approximately 4 kb. The chloroplast transformation vector pDD-Dc-gfp/BADH (FIG. 1A) is a carrot specific vector that harbors the gfp gene regulated by the gene 10 5' UTR/rps16 3' UTR (to facilitate expression in green as well as non-green tissues and screen transformants by GFP fluorescence) and the badh gene expressed under the psbA 5' and 3' UTRs (to facilitate expression in green tissues, regulated by light). All the 5' and 3' regulatory elements were PCR amplified from tobacco genomic DNA except for the gene 10 5' UTR which was derived from phage T7 gene 10. Transcription of both transgenes in this cassette is driven by the full length Prrn 16S rRNA promoter which contains regulatory elements for both the nuclear encoded and plastid encoded RNA polymerases, thereby facilitating transcription in green as well as non-green tissues. The chloroplast transformation vector pDD-Dc-aadA/BADH (FIG. 1B) harbors the aadA and badh genes whose expression is driven by the full length 16S rRNA promoter under the regulation of RBS (Ribosome Binding Site)/3'psbA UTR and the gene 10 5' UTR/rps16 3' UTR regulatory elements, respectively.

It should be further noted that the universal vector described in U.S. patent application Ser. No. 09/079,640 can be used to transform the plastid genome as described within this application.

Transformation of Carrot Plastids and Plant Regeneration.

Figures 2A, 2B, 2C, 2D:
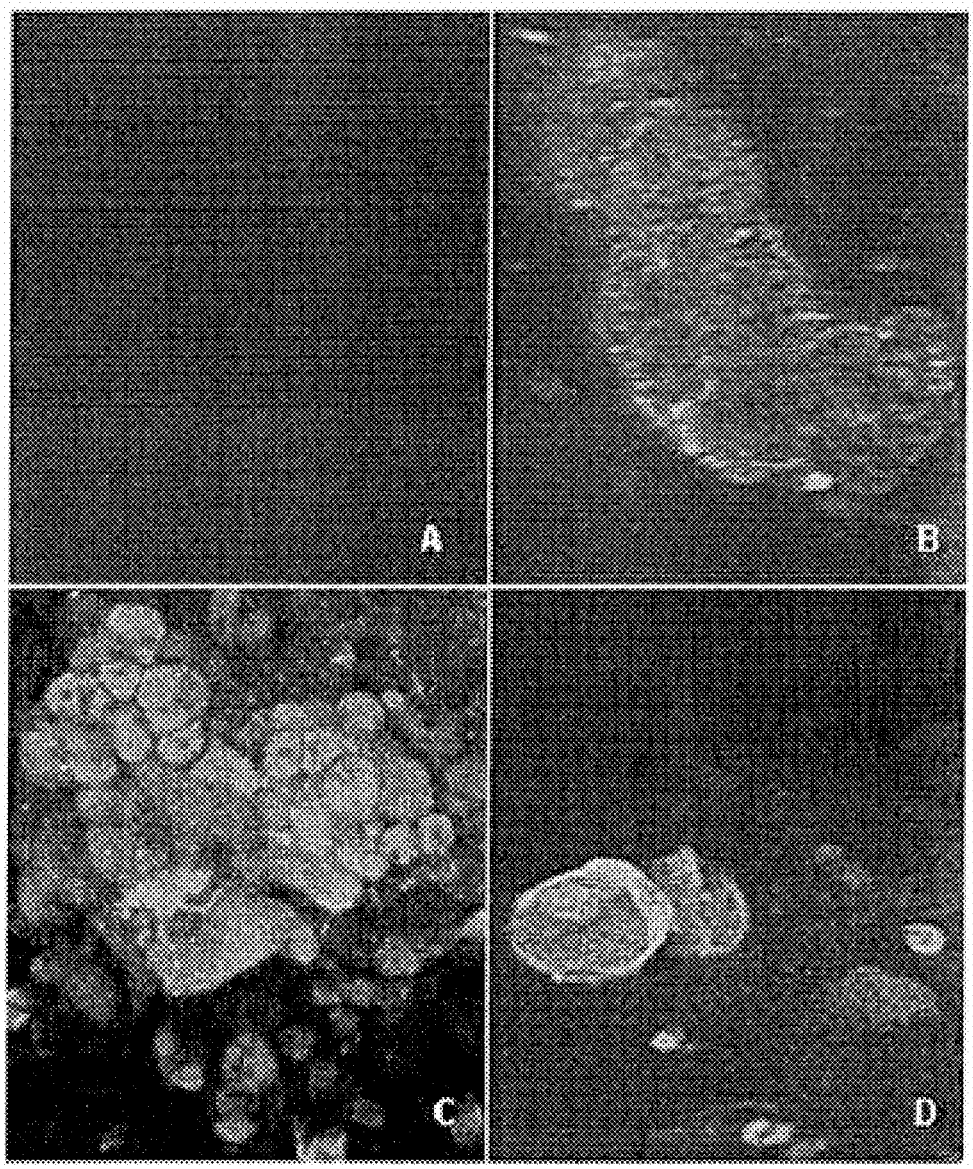
FIG. 2(A) shows the untransformed control carrot culture.
FIG. 2(B) shows the transformed embryogenic calli.
FIG. 2(C) shows the transformed embryogenic carrot calli differentiated into globular somatic embryos.
FIG. 2(D) shows a somatic embryo differentiated into cotyledonary stage.

Yellow fine cell suspension culture induced from stem segments of carrot (*Daucus carota* L. cv. Half long) was bombarded with carrot chloroplast vectors pDD-Dc-gfp/BADH and pDD-Dc-aadA/BADH as described (Daniell, 1997; Kumar and Daniell, 2003). Carrot cultures transformed with pDD-Dc-gfp/BADH vector, produced GFP expressing calli and somatic embryos that were observed under confocal microscope (FIG. 2 A-C) when selected on 20 mM betaine aldehyde (BA). Even though it was quite evident that somatic embryos expressing GFP could be regenerated rapidly on BA selection, there were two major limitations for using this vector. BA is quite expensive ($2000-$3000/gm) and this limited the number of experiments that could be performed and the badh gene was regulated by the psbA promoter and UTR elements, that was under developmental and light regulation. Unfortunately, cultured carrot cells were non-green and in early stages of development, thus minimizing badh expression. Therefore, more efforts were made to transform carrot cells using another chloroplast vector. Using the chloroplast vector pDD-Dc-aadA/BADH, seven independent transgenic cell lines were recovered within 2-3 months from five bombardments on solid medium (MSB+3 mg/L 2,4-D, 1 mg/L kinetin) containing different concentrations of spectinomycin (150-450 mg/L). Further, transgenic calli were transferred to medium containing 350-mg/L spectinomycin for a month and multiplied using 500-mg/L spectinomycin. All transgenic cell cultures were incubated under 100 1× light intensity at 26±2° C. temperature. The MSB medium, supplemented with 3-mg/L 2,4-D and 1 mg/L kinetin along with the selection agent, was used as the growth medium to induce and multiply the transgenic cell cultures. In order to multiply transgenic cultures, they were subcultured on solid medium every 2-3 week and were also grown in liquid medium (MSB+0.1 mg/L 2,4-D) at 130 rpm under diffuse light (50 1×). The medium without 2,4-D (MSB+0.2 mg/L kinetin) was used as the plant-regeneration-medium to convert embryogenic calli into plantlets via somatic embryogenesis. Transgenic plants maintained on basal MSB medium (containing 500 mg/L spectinomycin) were transferred to soil in pots to induce the mature taproot system and used for further characterization.

Visible Selection of Transgenic Carrot Cells.

Figure 3A:
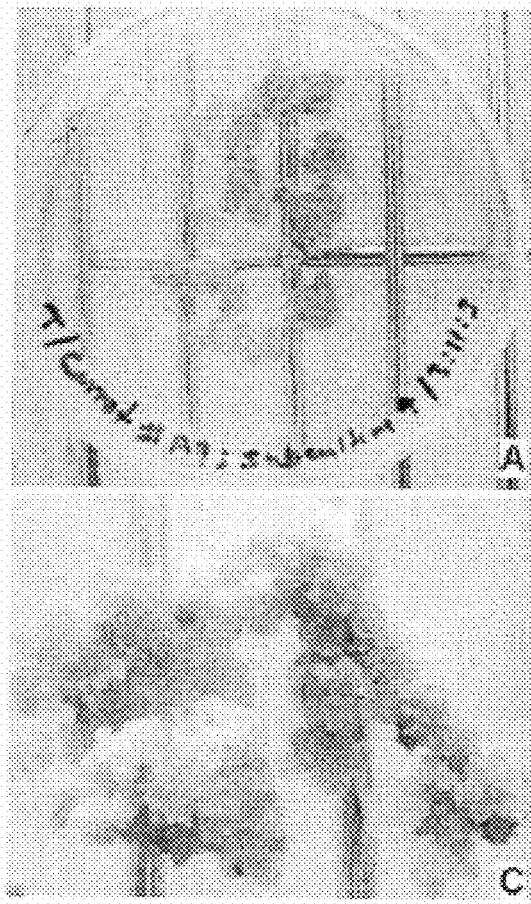
FIG. 3(A-D) shows the visual selection of green transgenic cells versus yellow non-transgenic carrot cells culture.
Figure 3B:
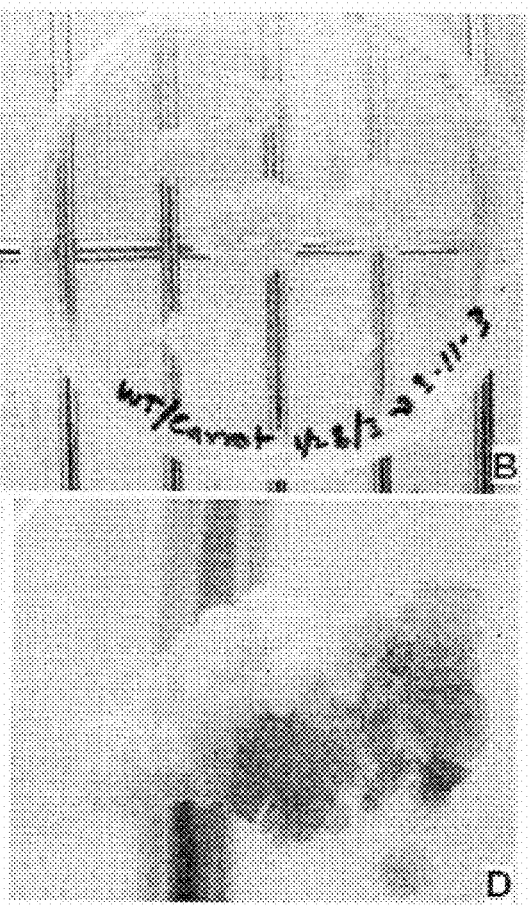
Figure 3C:
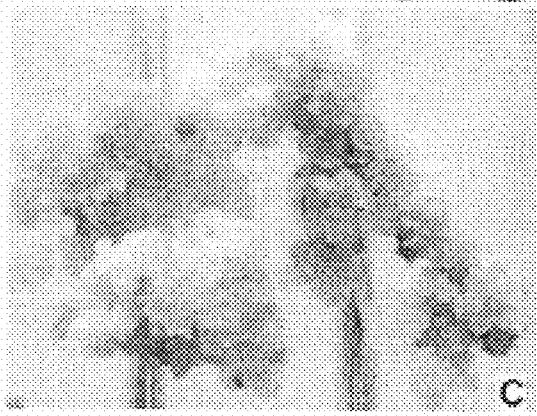
Figure 3D:

During in vitro cell culture studies of transgenic and non-transgenic carrot, it was interesting to note that carrot cells could be distinguished on the basis of color. Transgenic carrot cells, which carry the badh transgene, were always green in color whereas non-transgenic cells were yellow in color (see FIG. 3A-B). To test that transgenic bright green cells were truly transgenic, heteroplasmic (partially transformed plastids) carrot cell cultures were placed on a growth medium without selection and were allowed to segregate; green and yellow cells visually segregated within 3-4 weeks (FIG. 3C-D). Transgenic-green cells were confirmed positive for transgene integration while yellow cells were found to be untransformed. Further, suppression of untransformed cell division was possible, when cells were exposed to different concentrations of NaCl. This visible selection system would be vital to distinguish transformed from untransformed cells while eliminating the selectable antibiotic marker genes using direct repeats (Iamtham and Day, 2002) from transformed chloroplast genomes.

Confirmation of Transgenes Integration into Carrot Plastids.

Figures 4A, 4B:
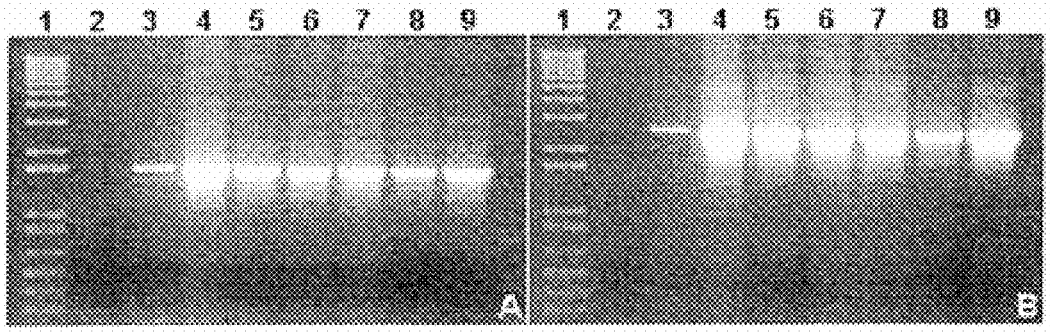
FIG. 4(A) shows the use of internal primers 3P (land on flanking sequence) and 3M (land on aadA gene) ~1.65 kb size PCR product was amplified at 64° C. annealing temperature, confirmed transgene integration into plant cell lines.
FIG. 4(B) shows the use of a set of primer 16SF (landing on the native chloroplast genome) and 1M (landing on the aadA gene) yield ~2.5 kb size PCR product at 64° C. annealing temperature, confirmed plastid specific integration of the transgenes. Lane 2 stand for DNA from non-transgenic carrot cells and lanes 2-9 represents DNA from seven transgenic carrot cell lines. Primers landing sites for primer pairs (3P/3M and 16SF/1M) is shown in FIG. 1B.

The carrot chloroplast vector pDD-Dc-aadA/BADH integrates the aadA and badh genes into the 16S-23S-spacer region of the plastid genome by homologous recombination. Transgene integration into carrot cell lines was confirmed by PCR (FIG. 4A) using internal primer set 3P (that lands on trnI region of plastids) and 3M (that lands on the aadA gene) producing 1.6 kb PCR product. This eliminates mutants that may be obtained on spectinomycin selection, caused by mutation of the chloroplast 16S rRNA gene. In order to distinguish between nuclear and chloroplast transgenic cell lines (FIG. 4B), 16S-F primer was landed on the native chloroplast genome, 200 bp upstream of integration site and 1M primer was landed on the aadA gene; this generated 2.5 kb size PCR product. Since this PCR product cannot be obtained in nuclear transgenic plants, the possibility of nuclear integration was eliminated. Thus, PCR analyses allow rapid screening of large number of putative transgenic lines and eliminate mutants or nuclear transgenic lines.

Determination of Homoplasmy in Transgenic Carrot Plastids.

Figure 1A:
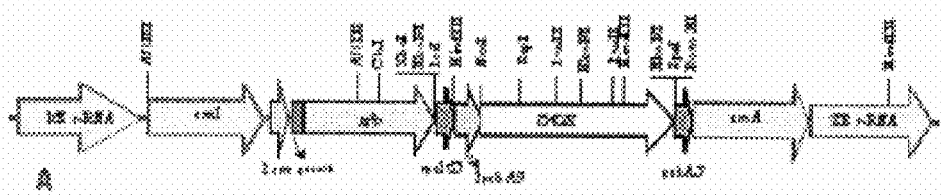
FIG. 1(A) shows carrot chloroplast transformation vector pDD-Dc-p/BADH carries the gfp and BADH genes expressed under the regulation of T7 gene 10 5' untranslated region (UTR)/rps16 3' UTR and PpsbA 5' and 3' UTR respectively. The Prrn promoter of 16S r-RNA gene, having both PEP and NEP recognition sites, drives expression of the cassette.
Figure 1B:
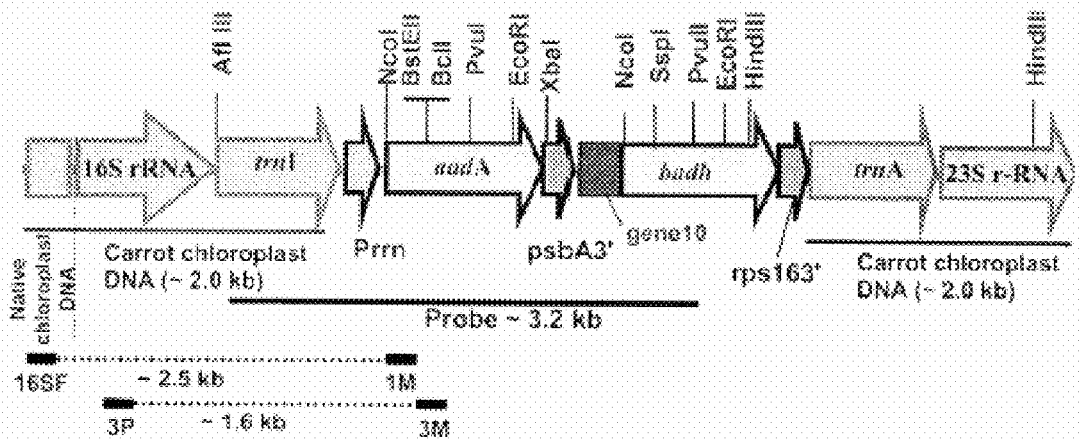
FIG. 1(B) shows the carrot chloroplast transformation vector pDD-Dc-aadA/BADH carries the aadA and BADH gene. Expression of aadA gene is under the regulation of Shine-Dalgarno sequence and psbA 3' UTR while that of BADH is regulated by gene 10 5' and rps16 3' UTR. AflIII/PvuII digested ~4.9 kb DNA fragment used as a probe for Southern analysis of the transgenic plants and landing sites for primers 3P/3M and 16SF/1M used to confirm the presence of the transgene integration into carrot plastids are shown.
Figure 4C:
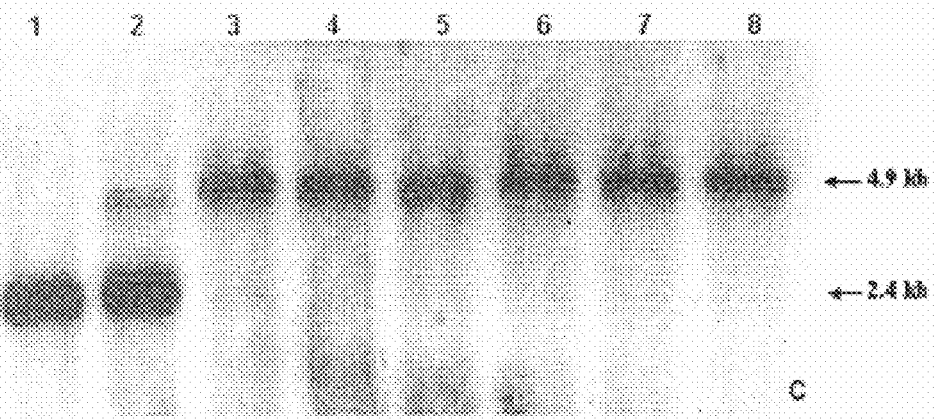
FIG. 4(C) shows the southern blot analysis of plastid genome of untransformed and transformed carrot with vector pDD-Dc-aadA/BADH. Carrot genomic DNA (5 μg per lane) digested with AflIII and PvuII and transferred to nitrocellulose membrane, was hybridized with the 4.9 kb radioactive labeled $P^{32}$ DNA probe (containing 2.4 kb flanking sequence and 2.5 kb transgene sequence, see FIG. 1B). Lane 1, control DNA from untransformed transgenic plant showed 2.4 kb size band while heteroplasmic transgenic plant from cell line one, lane 2 showed both bands. Homoplasmy in transgenics plants from different cell lines (lanes 3-8) was achieved by repetitive subcultures of transgenic cells in liquid medium.

PCR-confirmed transgenic carrot cell lines were repeatedly subcultured each week in liquid medium for several rounds of selection in the presence of spectinomycin selection agent. Southern blot analysis was performed using total genomic DNA isolated from untransformed and transformed carrot plants, developed from different transgenic cell lines, and was digested with AflIII and PvuII (FIG. 4C). The presence of the AflIII restriction site in the 16S-rRNA region (left flank) in both transformed and untransformed carrot plastids and a unique PvuII site in between trnI and trnA flanking regions of untransformed plastids as well as in the mid region of badh transgene, allowed excision of predicted size fragments in both the untransformed and transgenic lines. In order to confirm heteroplasmy or homoplasmy, genomic DNA of carrot plants digested with AflIII and PvuII was hybridized with the 4.9 kb radioactive DNA probe. This probe fragment was isolated from the chloroplast vector pDD-Dc-aadA/BADH, by digesting with AflIII and PvuII. This fragment includes the 2.4 kb trnI flanking sequence and 2.5 kb transgene sequences of the chloroplast vector (FIG. 1B). Transgenic plants developed after two subcultures in liquid medium on the selection agent (350 mg/L spectinomycin) showed heteroplasmy (FIG. 4C, lane 2), whereas plants that were developed from cell lines after 8-10 subcultures in liquid medium supplemented with high concentration of selecting agent (500 mg/L spectinomycin) showed homoplasmy (FIG. 4C, lanes 3-8).

BADH Enzyme Activity in Carrot Cells, Root and Shoot.

Figure 5A:
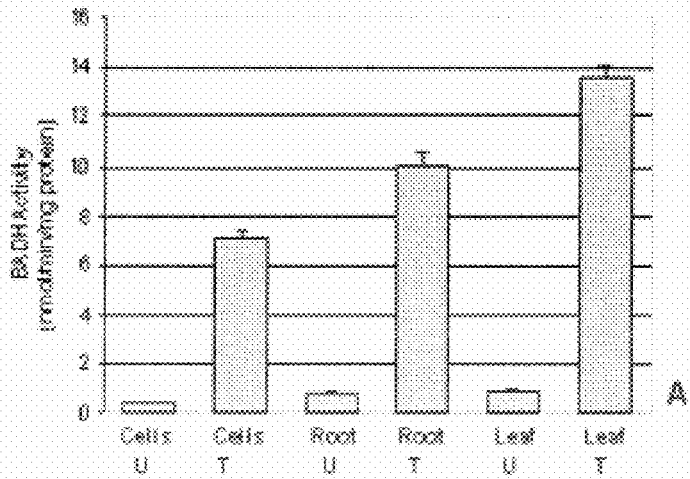
FIG. 5(A) shows the reduction of $NAD^+$ dependent BADH enzyme was analyzed for the formation of NADH at 340 nm in presence of betaine aldehyde. Very low BADH activity was detected in untransformed cells suspension (U), carrot root (U) and leaf (U). On the other hand, high BADH activity was recorded about 54% in transformed carrot cells suspension (T), about 72% in root (T) in comparison to leaf (T) tissues.

BADH enzyme activity was assayed in crude extracts from untransformed and transformed carrot cell cultures, tap roots (carrot) and leaves as described (Daniell et al. 2001). The expression of badh transgene was observed in cells and different parts of carrot plants using 50 µg crude extract of protein from each sample, desalted using G-25 column. BADH enzyme in the presence of betaine aldehyde converts $NAD^+$ to NADH and the reaction rate was measured by an increase in absorbance at 340 nm due to the reduction of $NAD^+$. Crude extracts from transgenic plastids (cells, tap roots and leaves) demonstrated elevated levels of BADH activity compared to untransformed tissues of carrot (FIG. 5A). Higher BADH activity was observed in leaves, tap roots of carrot plants and transgenic cells in suspension culture, confirming that full length 16S promoter Prrn and gene10UTR are highly suitable for expressing transgenes in various tissues. It is known that plastid genome copy numbers vary significantly in different tissues, with only 5% observed in roots compared to leaves (Sasaki et al. 1990). However, the high BADH enzyme activity observed in carrot tap root (75% of leaves) may be due to the large number of chromoplasts present; this was evident by their orange or purple color, instead of colorless roots normally observed in plants that contain only 5% of the plastid copies.

BADH Protein Expression in Carrot Cells, Root and Shoot.

Figure 5B:
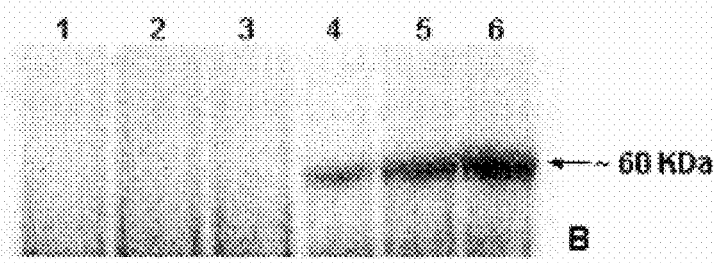
FIG. 5(B) shows that the BADH expression was analyzed by western blot. Whole cell extracts from transformed and untransformed carrot cell culture, root and leaf tissues were prepared and 50 μg total soluble protein from each sample was run on 10% SDS-PAGE and protein transferred to Immuno-blot™ PVDF membrane and hybridized with polyclonal anti-BADH serum, raised in rabbits against native BADH. Antigenic peptides were detected using horseradish peroxidase-linked secondary antibody. Lane 1, 2, 3 contain whole carrot extract from untransformed cell culture, root and leaf and lane 4, 5, 6 contain whole carrot extract from transformed cell culture, root and leaf. Transgenic cells expresses about 50% less (lane 4), root about 25% less (lane 5) BADH protein than leaf (lane 6).

To further confirm the results of BADH activity in cells, tap roots and leaves, Western blot analysis was done using crude extracts prepared from transformed and untransformed carrot tissues. A fraction from each sample (50 µg protein) was subjected to 10% SDS-PAGE. Protein transferred to nitrocellulose membrane was hybridized with polyclonal anti-BADH serum, raised in rabbits against native BADH (kindly provided by Dr. Elisa Soto; Figueroa-Soto et al. 1999), and antigenic peptides were detected using horseradish peroxidase-linked secondary antibody. No badh expression was detected in untransformed carrot tissues (cells, tap roots and leaves; FIG. 5B lanes 1-3). However, in transgenic samples (FIG. 5B), higher expression was observed in leaves (lane 6) and tap roots (lane 5) compared to carrot cell suspension cultures (lane 4). BADH protein accumulation in carrot root and leaf tissues were parallel to the results obtained with BADH enzyme activity in transgenic roots and shoots.

Salt Tolerance and BADH Activity in Cell Suspension Cultures of Carrot

Figure 6A:
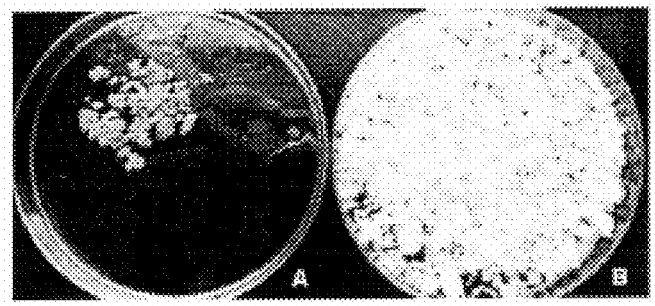
FIG. 6(A), part A shows the dry mass in untransformed carrot cell culture.
Figure 6B:
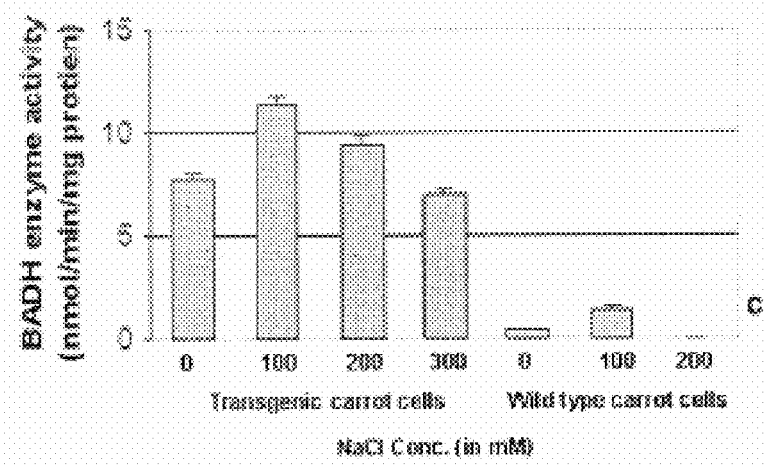
FIG. 6(B) shows the stimulation of BADH activity in presence of salt. Untransformed and transformed carrot cells in suspension cultures were placed on shaker at 130 rpm speed for two weeks in liquid medium containing 0, 100, 200 and 300 mM NaCl. Elevated level of BADH activity in transgenic cell cultures was noticed when liquid growth medium containing 100 and 200 mM NaCl.

In order to test whether salt stress affects the BADH activity, experiments were performed under different salt concentrations (0-500 mM NaCl) on carrot cell suspension cultures. Studies performed for two weeks on carrot cells showed that transformed cells were able to sustain and proliferate in higher concentrations of NaCl in the liquid medium than untransformed cells (FIG. 6A-B). Using a 500 mL conical flask containing 100 ml medium, carrot cultures produced about 11.82 g cells in both transformed and untransformed (1475%) while, in presence of 100 mM NaCl, 8.75 g transgenic cells (1096%) and 1.29 g untransformed cells (161%) were obtained after two weeks (when initial culture used contained 0.8 g per flask, see FIG. 6A-B). Furthermore, BADH enzyme activity was stimulated in transgenic carrot cell cultures when they were exposed to 100 to 300 mM NaCl. Maximum noticeable BADH activity was seen in 100 and 200 mM NaCl (FIG. 6C) and such increase was insignificant in untransformed cells. This shows that the full length Prrn promoter and gene 10 5' UTR facilitate efficient transcription and translation in all tissues, irrespective of the developmental stage, despite low copy number of plastid genomes in non-green cells or roots.

Effect of Salt on Carrot Plants.

Figure 7:
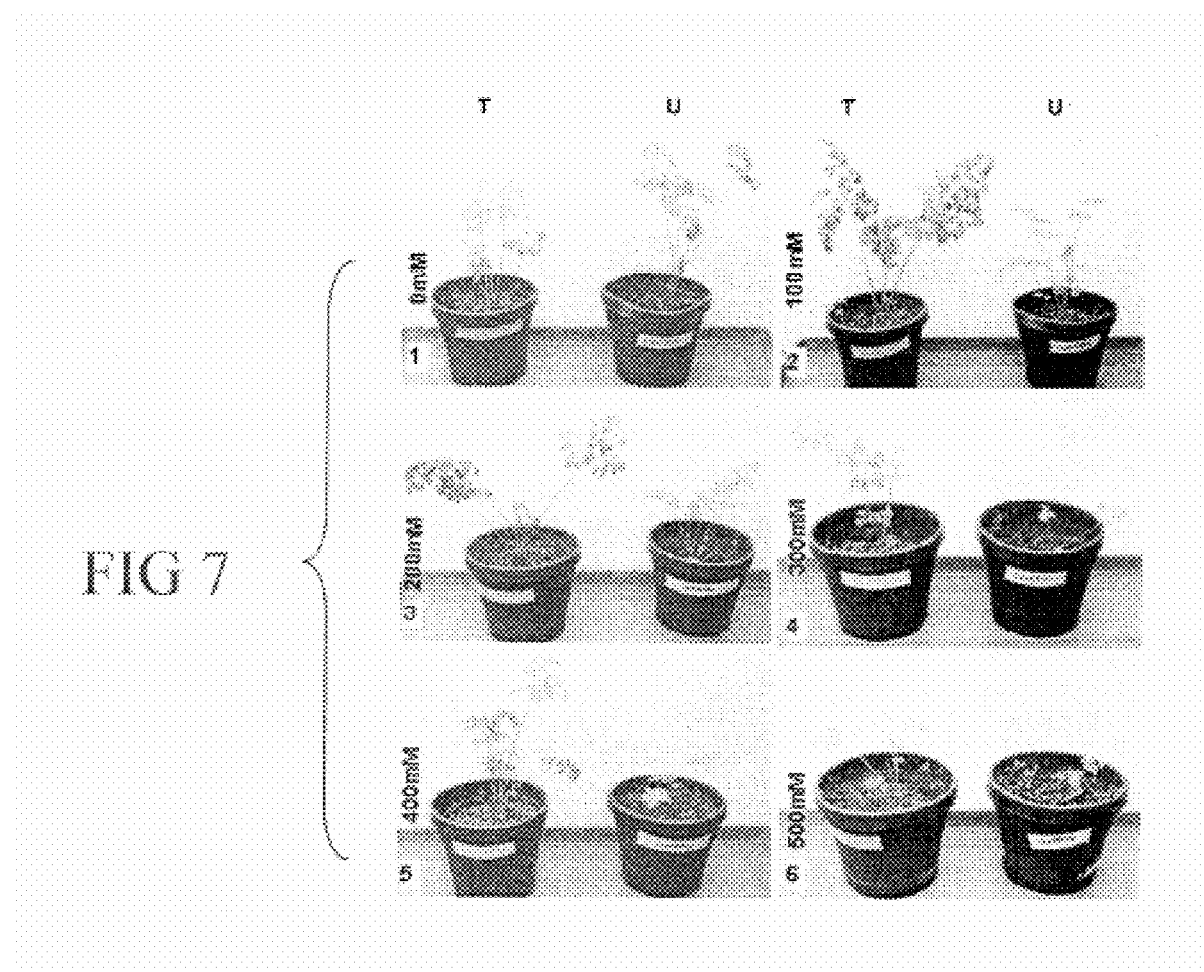
FIG. 7 shows effect of salt (100-500 mM NaCl) on untransformed (U) and transformed (T) carrot plants. Transgenic plants were tested for one month on different concentrations of NaCl. Plants were irrigated with water containing different concentrations NaCl at alternative days up to four weeks.
Figure 8:
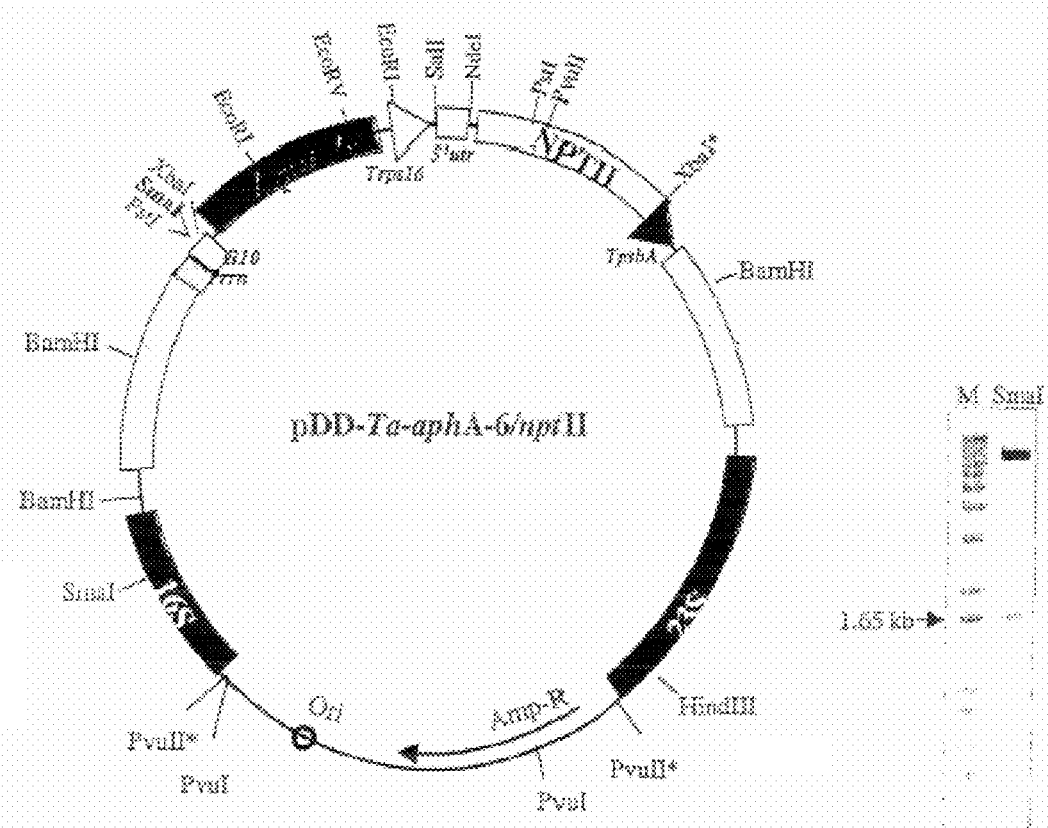
FIG. 8 shows the plasmid pDD-Ta-aphA-6/nptII. More particularly the plasmid illustrates pDA-76 (aphA-6/nptII expression cassette), having a backbone vector pBluescript II KS, a selectable marker/host cell Ampicillin/Kan/XL-1 Blue MRF' Tc, and a flanking region from *Triticum aestivum* (Ta).
Figure 9:
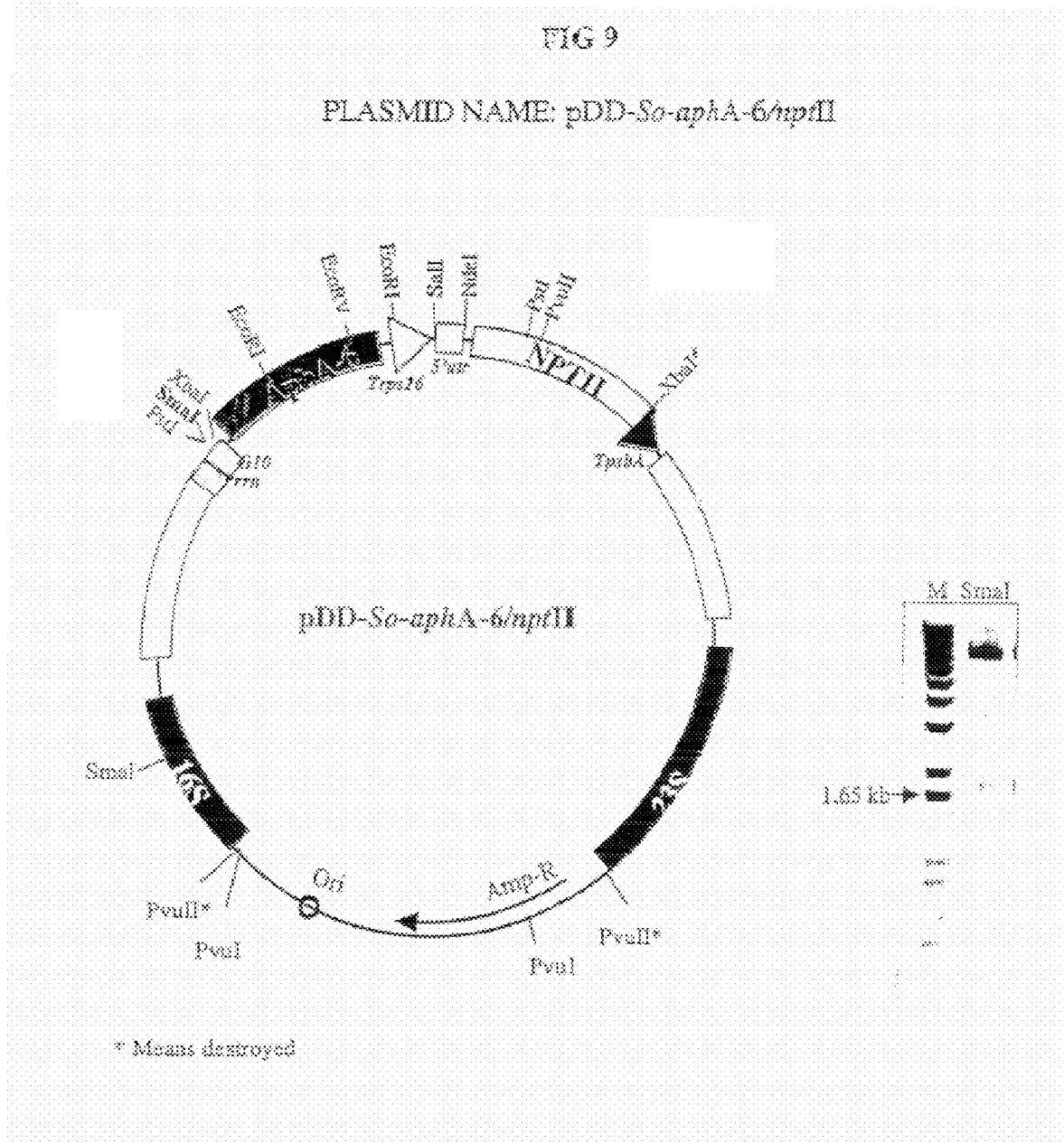
FIG. 9 shows the plasmid pDD-So-aphA-6/nptII. More particularly the plasmid illustrates pDA-76 (aphA-6/nptII expression cassette), having a backbone vector pBluescript II KS, a selectable marker/host cell Ampicillin/Kan/XL-1 Blue MRF' Tc, and a flanking region from *Saccharum officinarum* (So).
Figure 10:
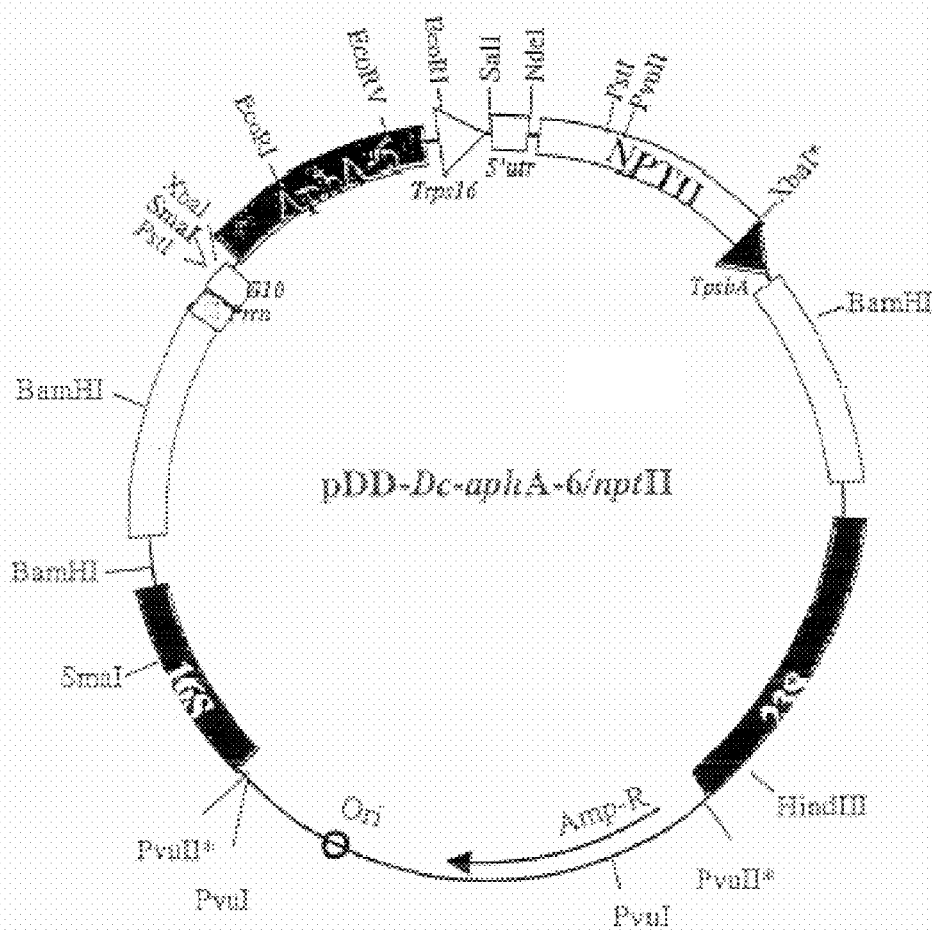
FIG. 10 shows the plasmid pDD-Dc-aphA-6/nptII. More particularly the plasmid illustrates pDA-76 (aphA-6/nptII expression cassette), having a backbone vector pBluescript II KS, a selectable marker/host cell Ampicillin/Kan/XL-1 Blue MRF' Tc, and a flanking region from *Daucus carota* (Dc).
Figure 11:
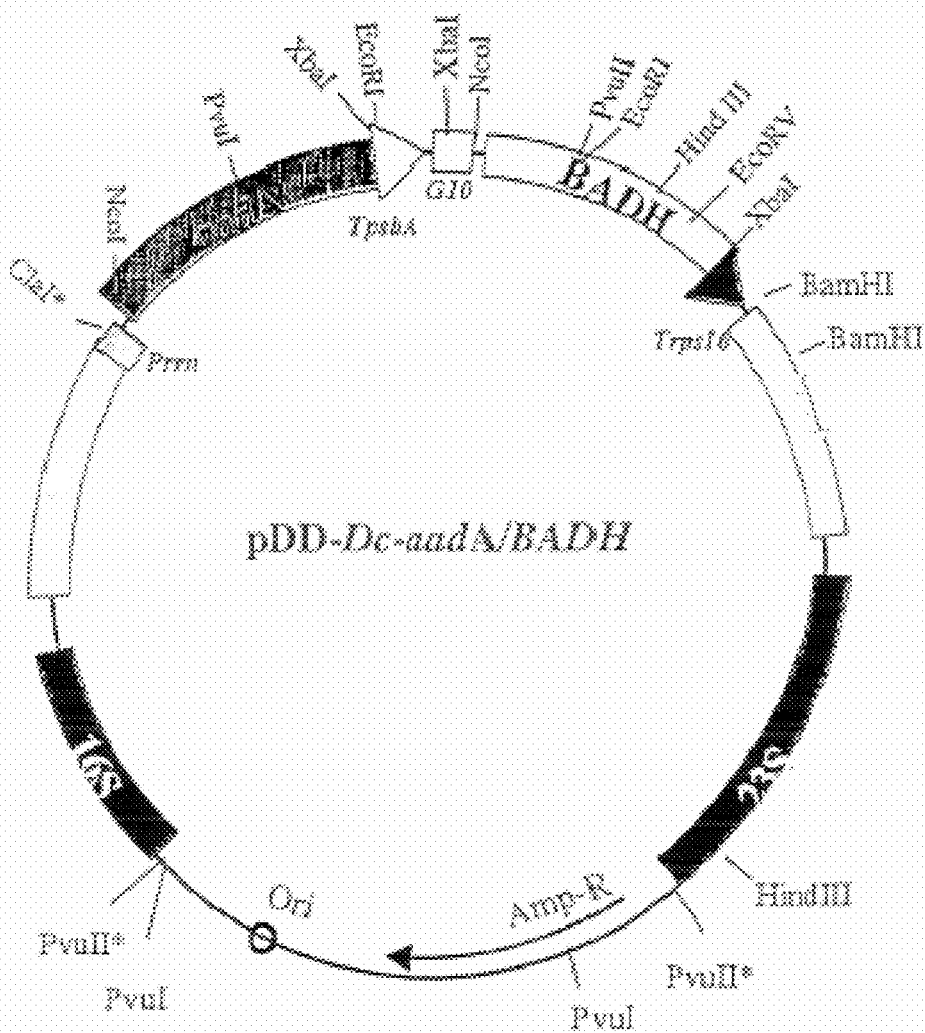
FIG. 11 shows the plasmid pDD-Dc-aadA/BADH. More particularly the plasmid illustrates pDA-29 (aadA/BADH expression cassette) having a backbone vector pBluescript II KS, a selectable marker/host cell Ampicillin/spectinomycinXL-1 Blue MRF' Tc, and a flanking region from *Daucus carota* (Dc).
Figure 12:
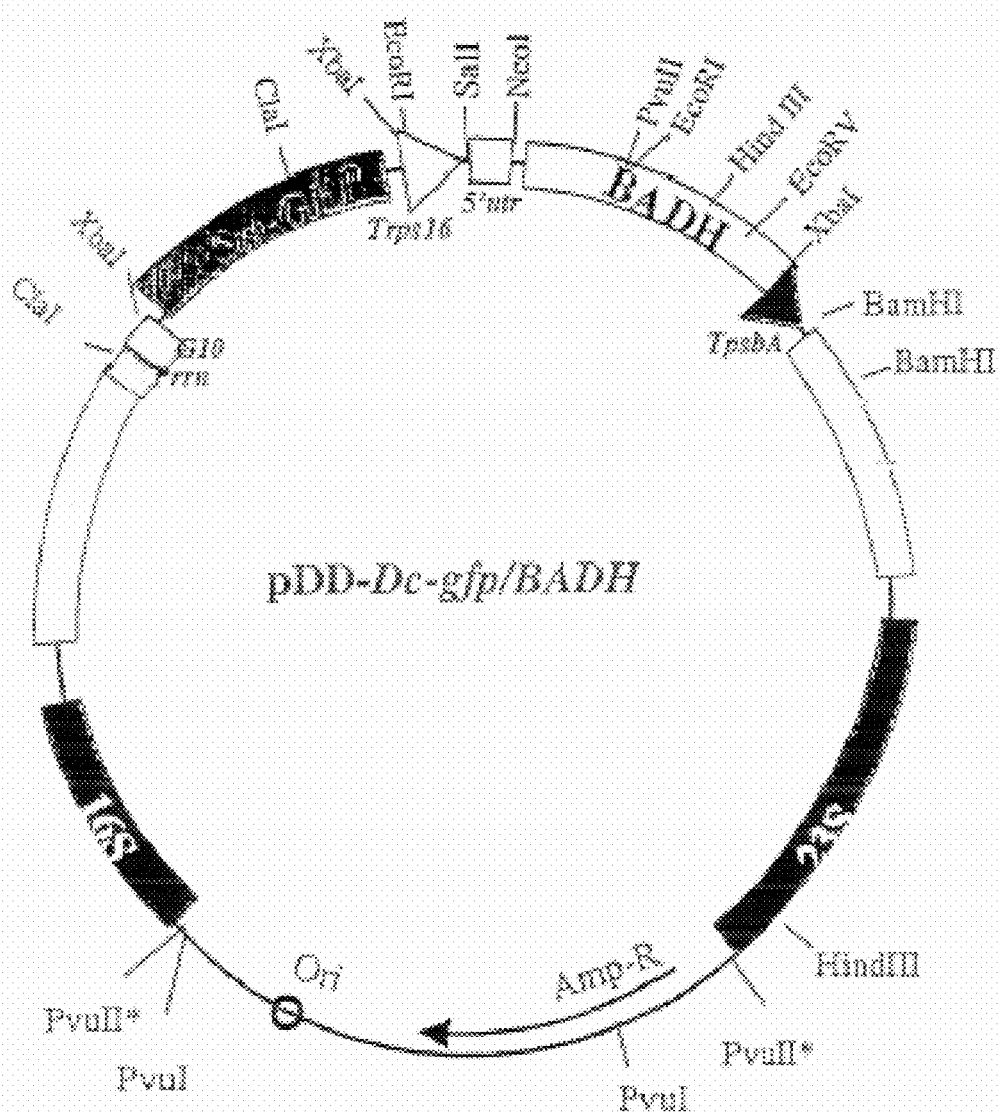
FIG. 12 shows the plasmid pDD-Dc-gfp/BADH. More particularly the plasmid illustrates pDA-30 (gfp/BADH expression cassette), having a backbone vector pBluescript II KS, a selectable marker/host cell Ampicillin/Kan/XL-1 Blue MRF' Tc, and a flanking region from *Daucus carota* (Dc).
Figure 13:
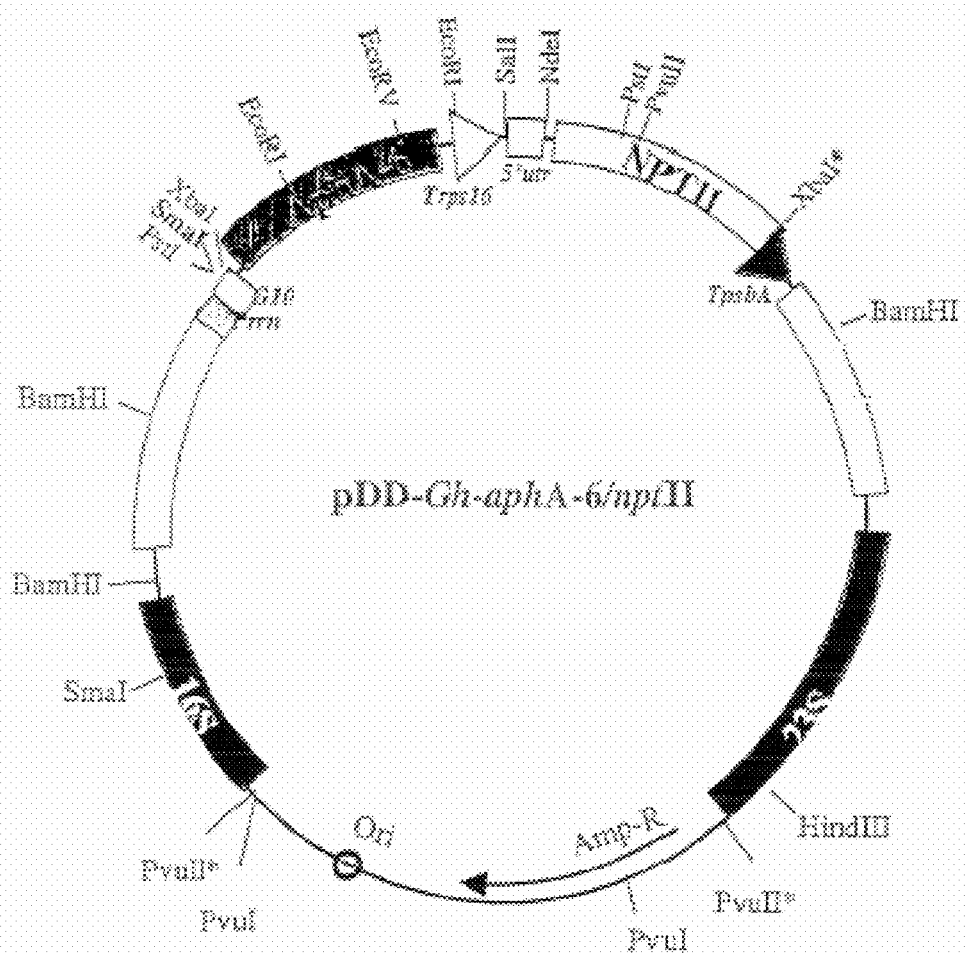
FIG. 13 shows the plasmid pDD-Gh-aphA-6/nptII. More particularly the plasmid illustrates pDA-76 (aphA-6/nptII expression cassette), having a backbone vector pBluescript II KS, a selectable marker/host cell Ampicillin/Kan/XL-1 Blue MRF' Tc, and a flanking region from *Gossypium hirsutum* (Gh).
Figure 14:
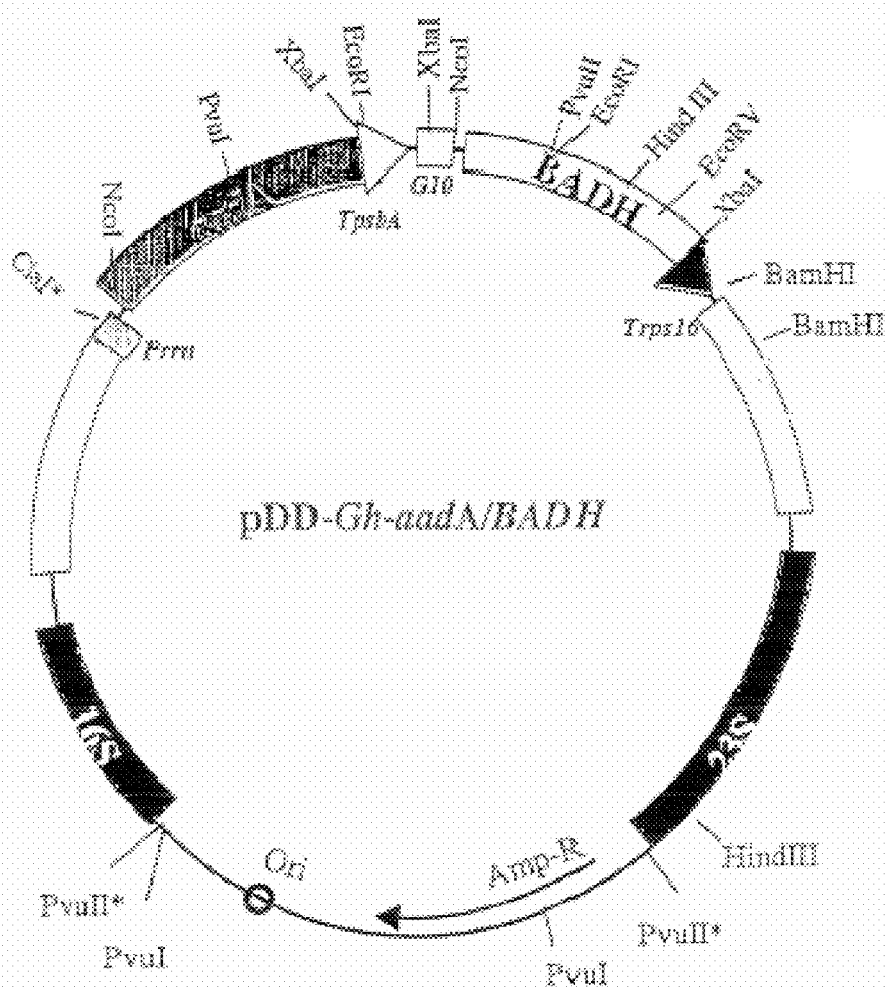
FIG. 14 shows the plasmid pDD-Gh-aadA/BADH. More particularly the plasmid illustrates pDA-29 (aadA/BADH expression cassette), having a backbone vector pBluescript II KS, a selectable marker/host cell Ampicillin/spectinomycinXL-1 Blue MRF' Tc and a flanking region from *Gossypium hirsutum* (Gh).
Figure 15:
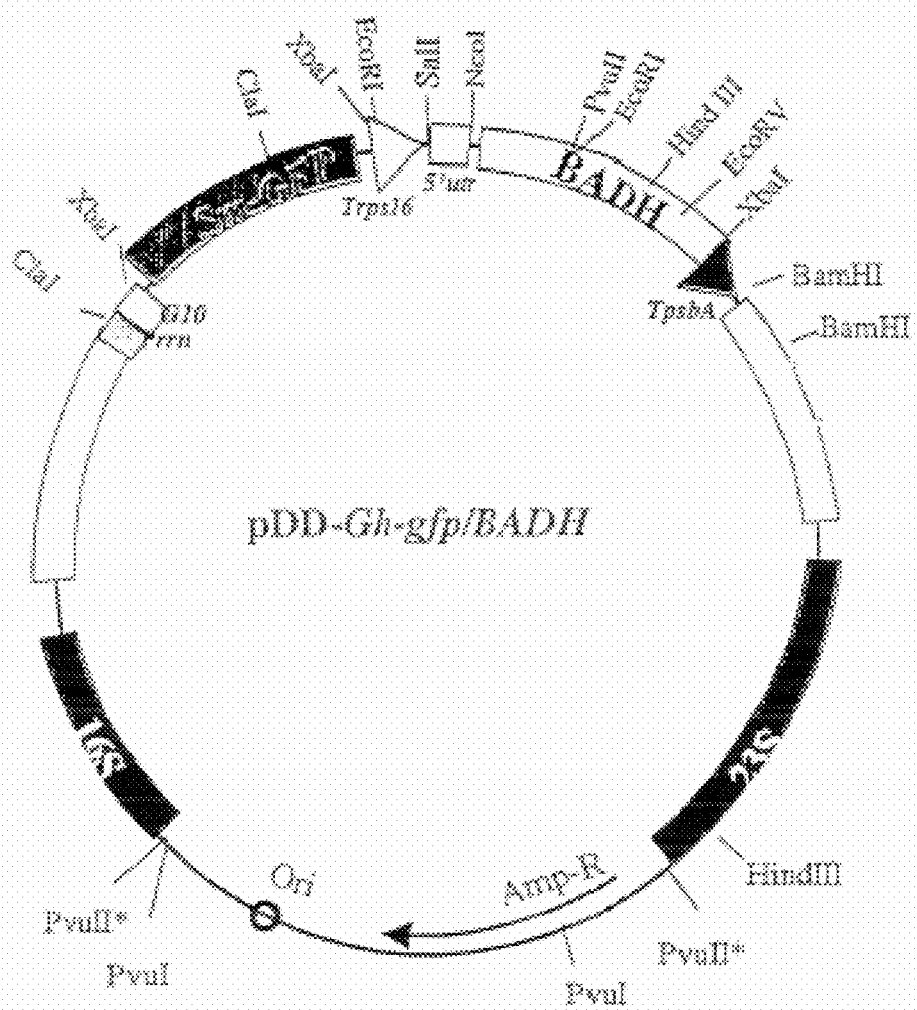
FIG. 15 shows the plasmid pDD-Gh-gfp/BADH. More particularly the plasmid illustrates pDA-30 (gfp/BADH expression cassette), having a backbone vector pBluescript II KS, a selectable marker/host cell Ampicillin/XL-1 Blue MRF' Tc, and a flanking region from *Gossypium hirsutum* (Gh).
Figure 16:
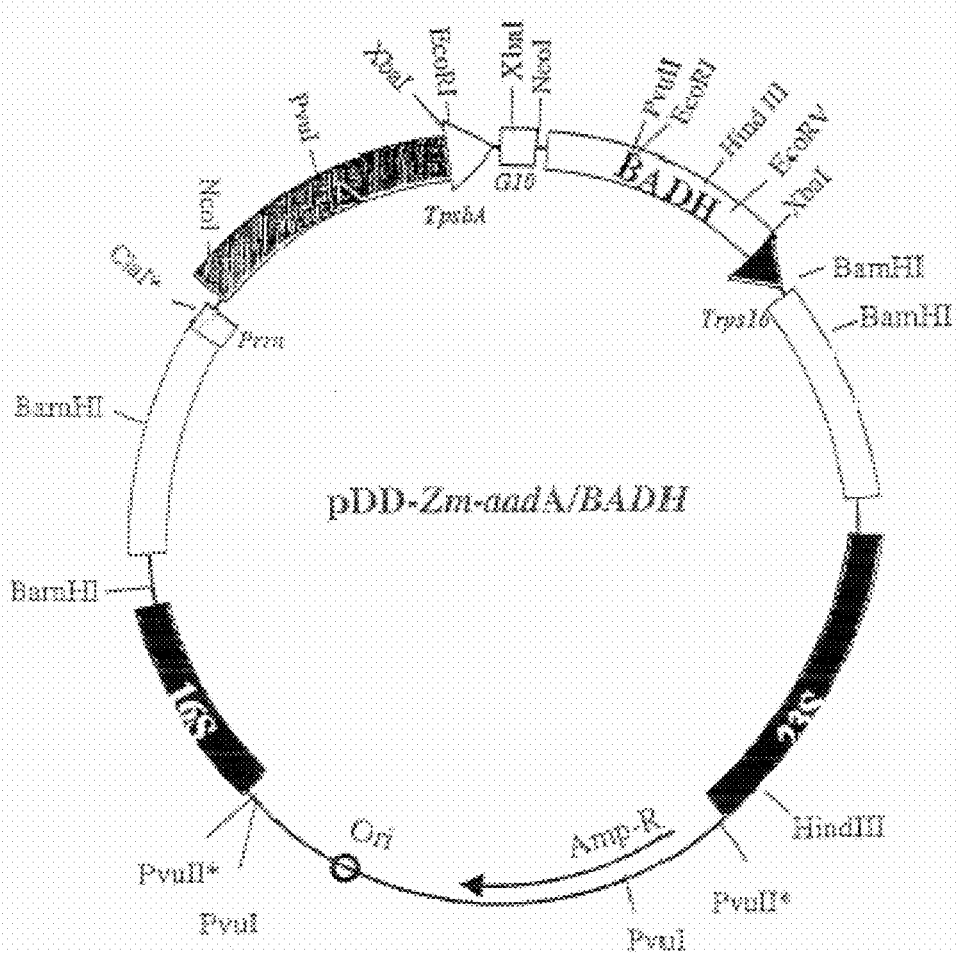
FIG. 16 shows the plasmid pDD-Zm-aadA/BADH. More particularly the plasmid illustrates pDA-29 (aadA/BADH expression cassette), having a backbone vector pBluescript II KS, a selectable marker/host cell Ampicillin/spectinomycinXL-1 Blue MRF' Tc, and a flanking region from *Zea mays* (Zm).
Figure 17:
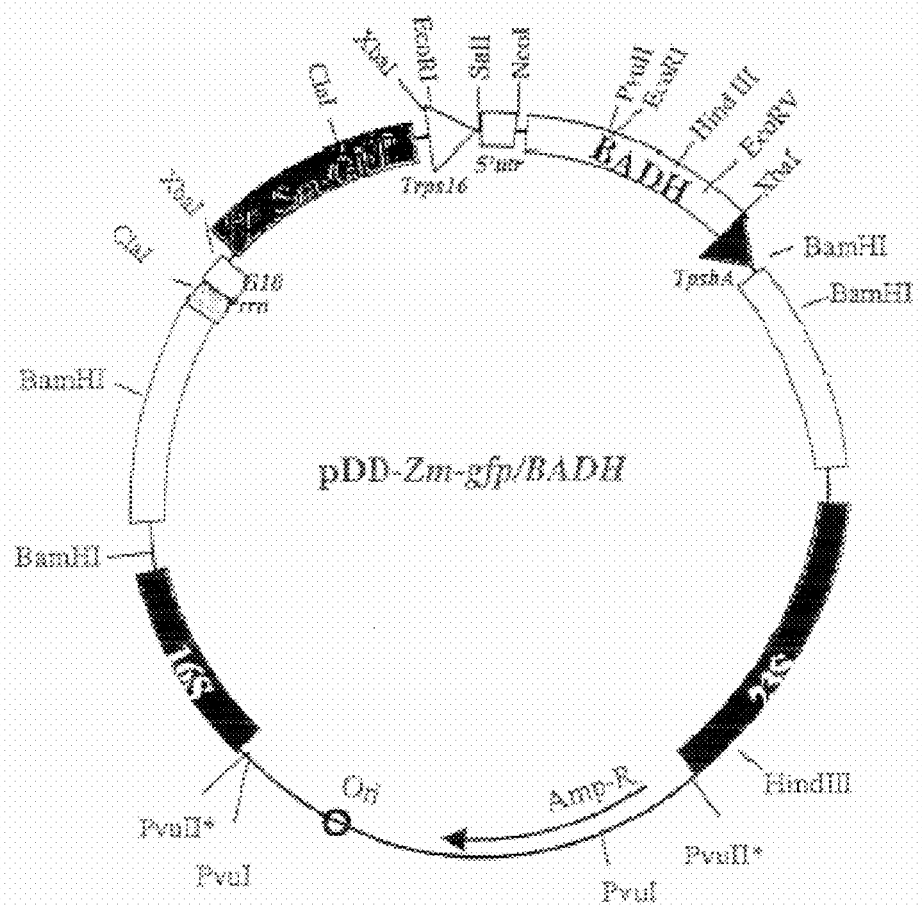
FIG. 17 shows the plasmid pDD-Zm-gfp/BADH. More particularly the plasmid illustrates pDA-30 (gfp/BADH expression cassette), having a backbone vector pBluescript II KS, a selectable marker/host cell Ampicillin/XL-1 Blue MRF' Tc, and a flanking region from *Zea mays* (Zm).
Figure 18:
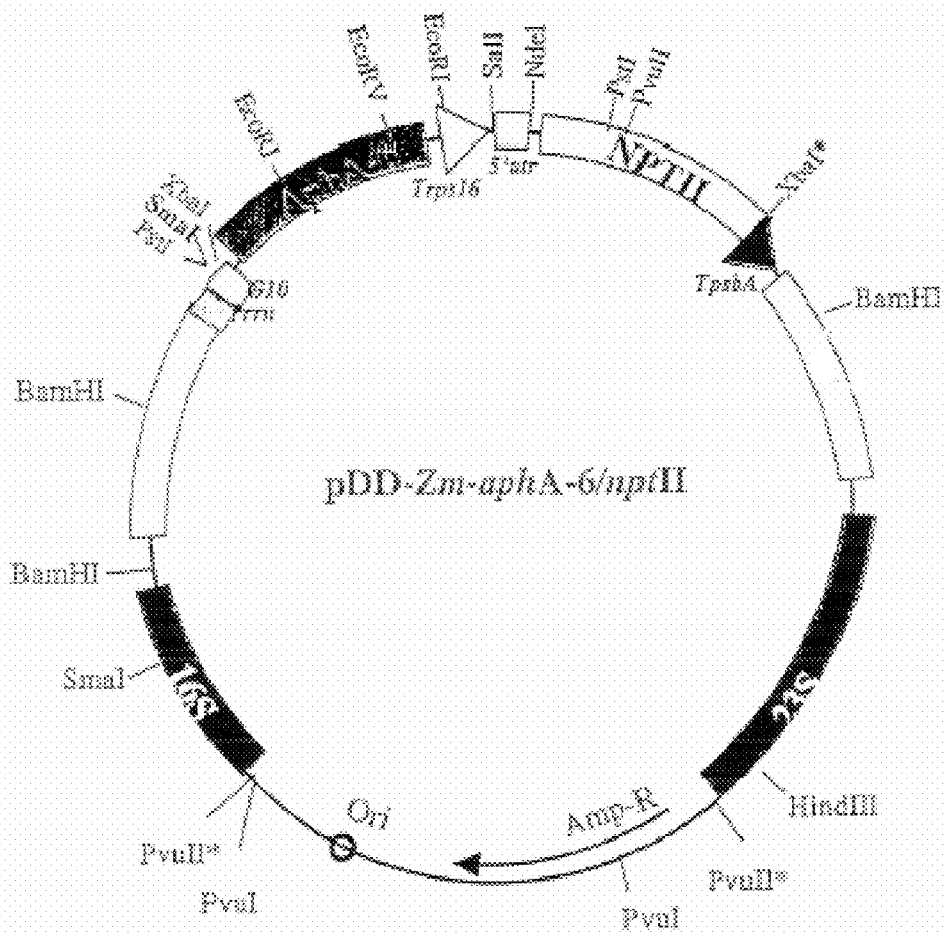
FIG. 18 shows the plasmid pDD-Zm-aphA-6/nptII. More particularly the plasmid illustrates pDA-76 (aphA-6/nptII expression cassette), having a backbone vector pBluescript II KS, a selectable marker/host cell Ampicillin/Kan/XL-1 Blue MRF' Tc, and a flanking region from *Zea mays* (Zm).
Figure 19:
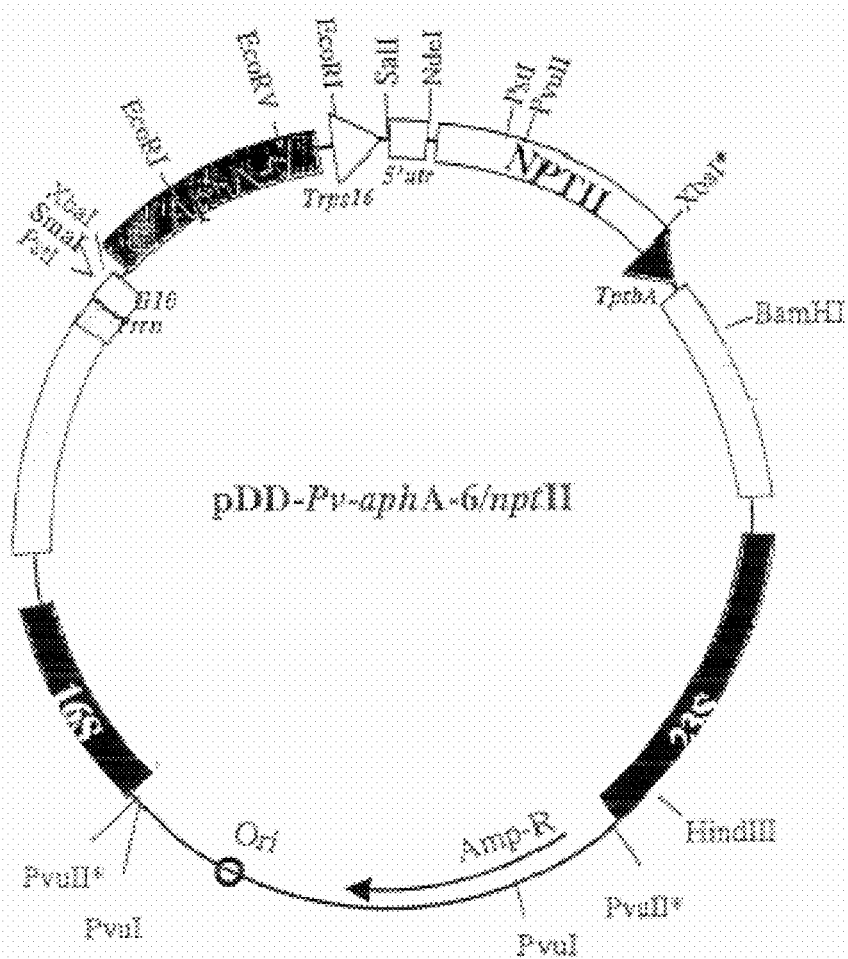
FIG. 19 shows the plasmid pDD-Pv-aphA-6/nptII (switchgrass). More particularly the plasmid illustrates pDA-76 (aphA-6/nptII expression cassette), having a backbone vector pBluescript II KS, a selectable marker/host cell Ampicillin/Kan/XL-1 Blue MRF' Tc, and a flanking region from *Panicum virgatum* (Pv).
Figure 20:
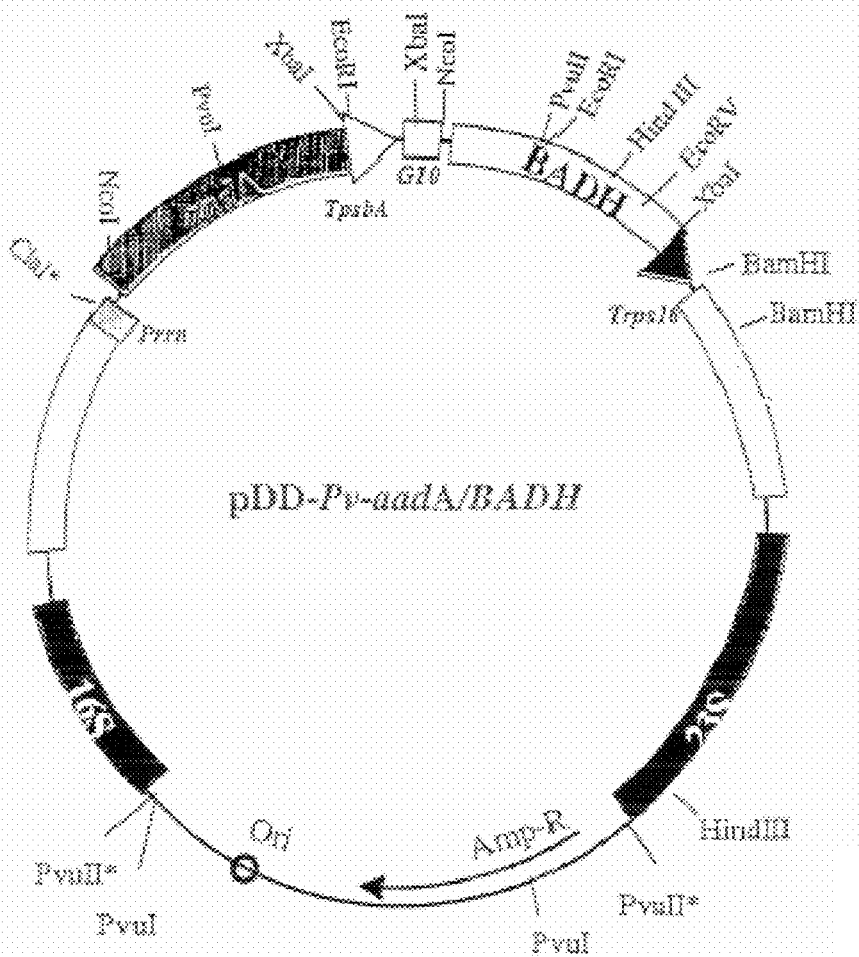
FIG. 20 shows the plasmid pDD-Pv-aadA/BADH (switchgrass). More particularly the plasmid illustrates pDA-29 (aadA/BADH expression cassette), having a backbone vector pBluescript II KS, a selectable marker/host cell: Ampicillin/spectinomycinXL-1 Blue MRF' Tc, and a flanking region from *Panicum virgatum* (Pv).
Figure 21:
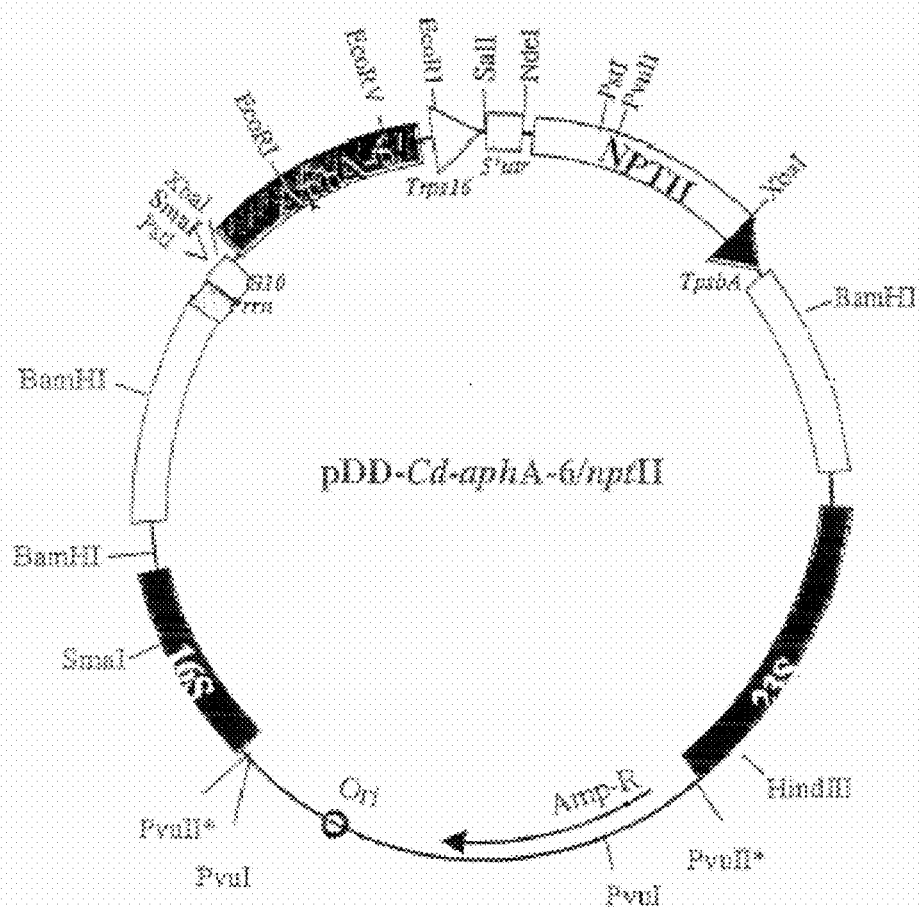
FIG. 21 shows the plasmid pDD-Cd-aphA-6/nptII (bermudagrass). More particularly the plasmid illustrates pDA-76 (aphA-6/nptII expression cassette), having a backbone vector pBluescript II KS, a selectable marker/host cell: Ampicillin/Kan/XL-1 Blue MRF' Tc, and a flanking region from *Cynodon dactylon* (Cd).
Figure 22:
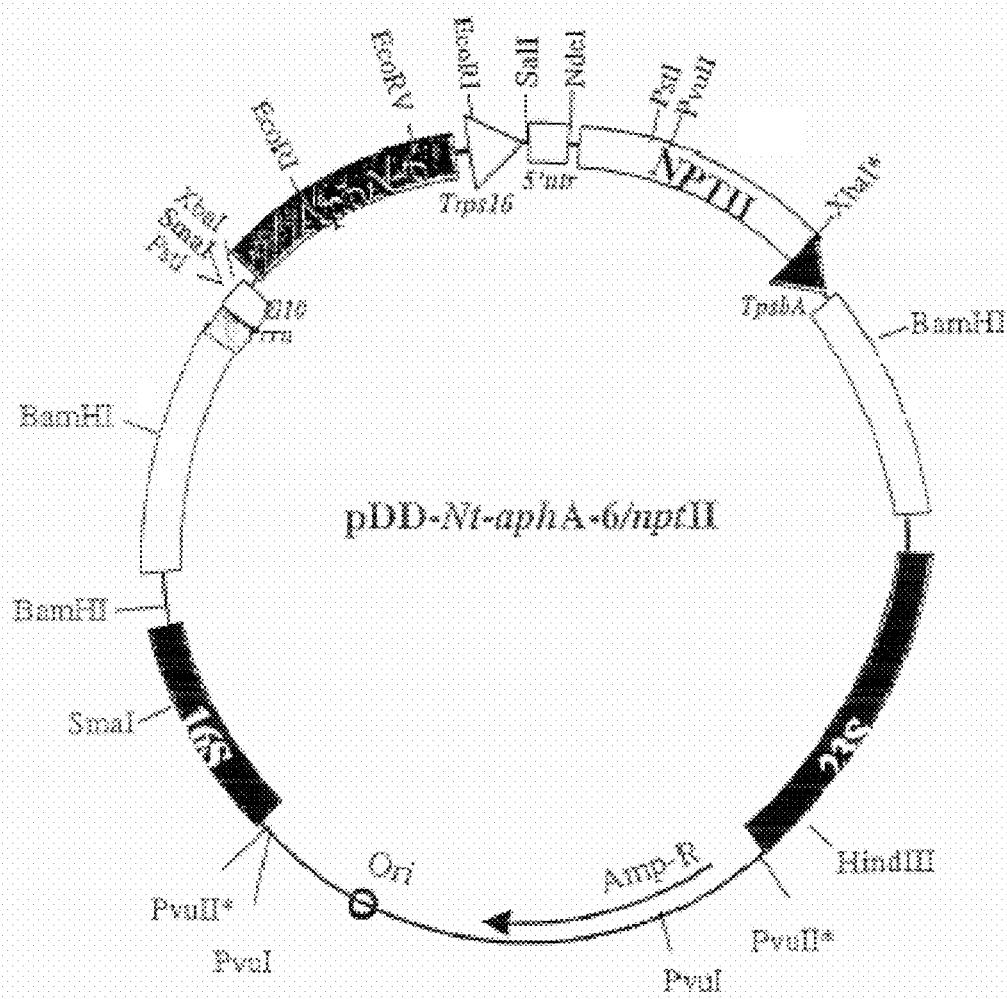
FIG. 22 shows the plasmid pDD-Nt-aphA-6/nptII. More particularly the plasmid illustrates pDA-76 (aphA-6/nptII expression cassette), having a backbone vector pBluescript II KS, a selectable marker/host cell Ampicillin/Kan/XL-1 Blue MRF' Tc, and a flanking region from *Nicotiana tabacum* (Nt).
Figure 23:
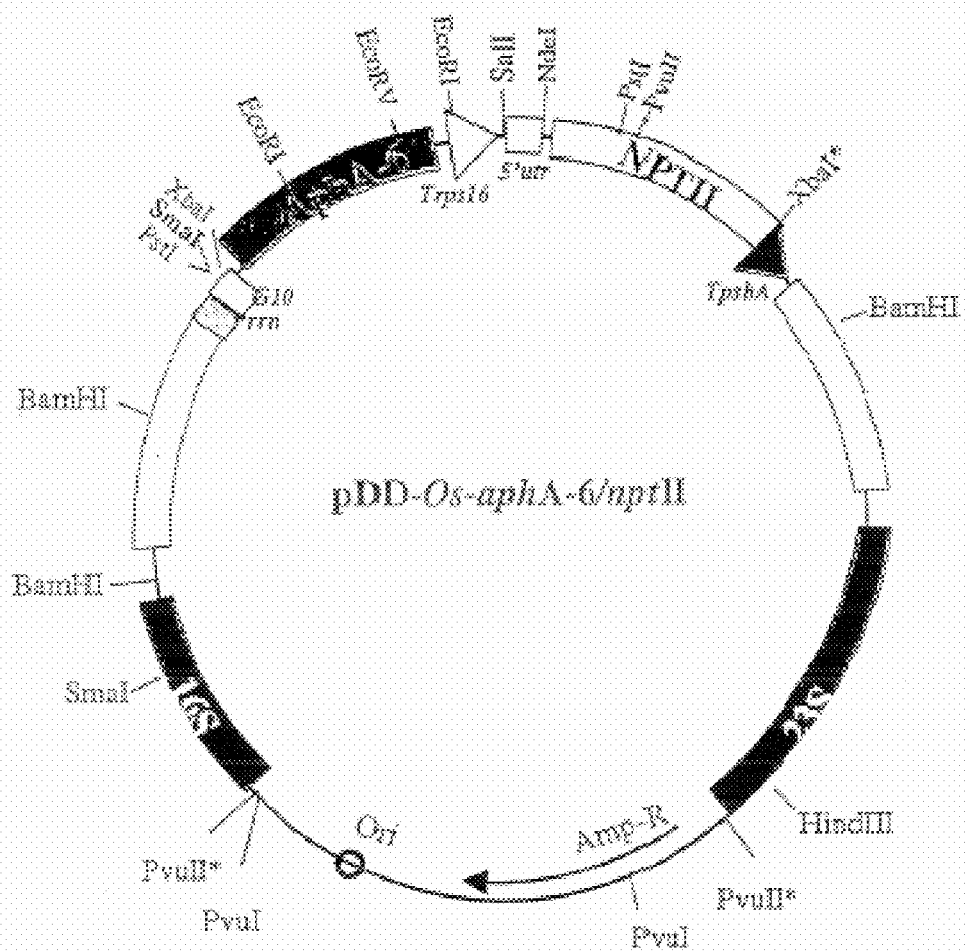
FIG. 23 shows the plasmid pDD-Os-aphA-6/nptII. More particularly the plasmid illustrates pDA-76 (aphA-6/nptII expression cassette), having a backbone vector pBluescript II KS, a selectable marker/host cell Ampicillin/Kan/XL-1 Blue MRF' Tc, and a flanking region from *Oryza sativa* (Os).
Figure 24:
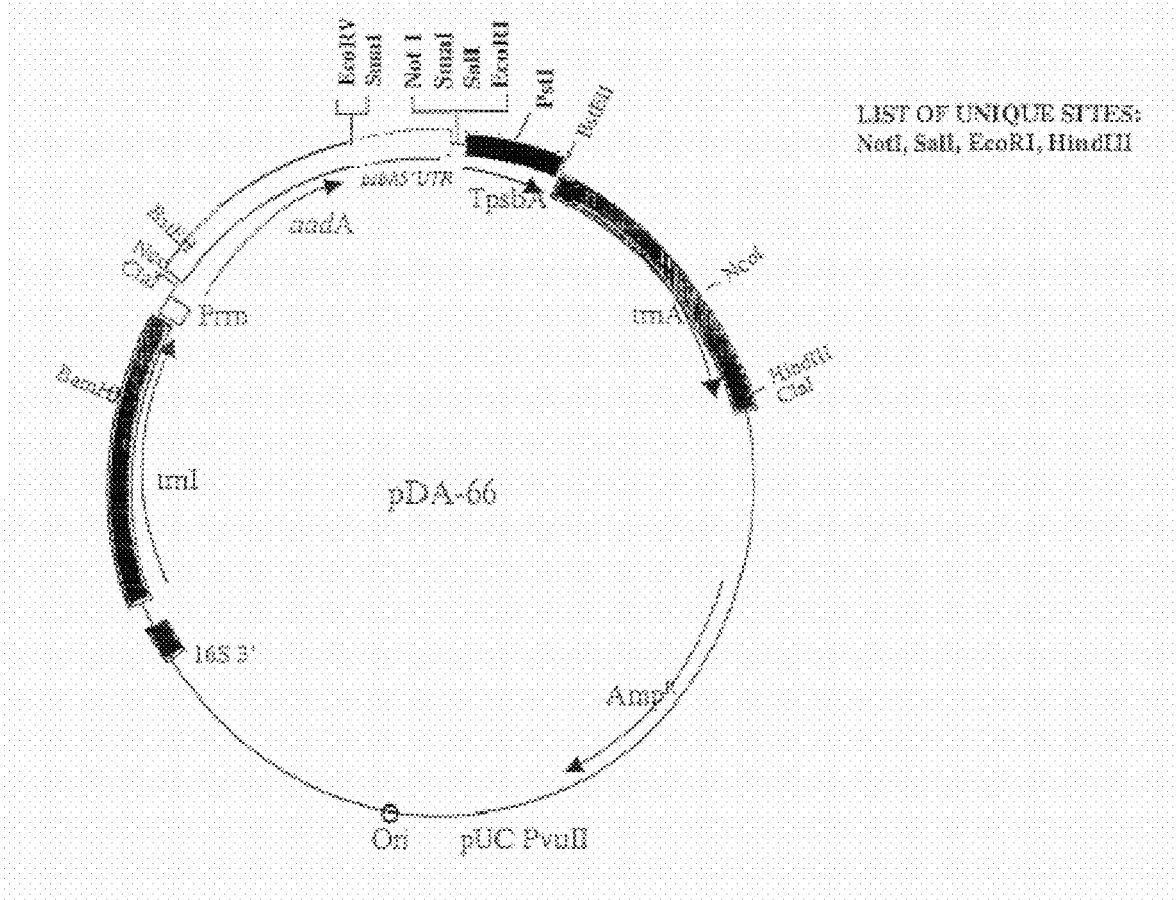
FIG. 24 shows the plasmid pDA-66. More particularly the plasmid illustrates psbA 5' UTR BACKBONE VECTOR pUC 19, which is a Derivative of pLD-CtV basic vector (modified MCS) having a selectable marker/host cell Ampicillin/Kan/XL-1 Blue MRF' Tc, and a flanking region from Tobacco.
Figure 25:
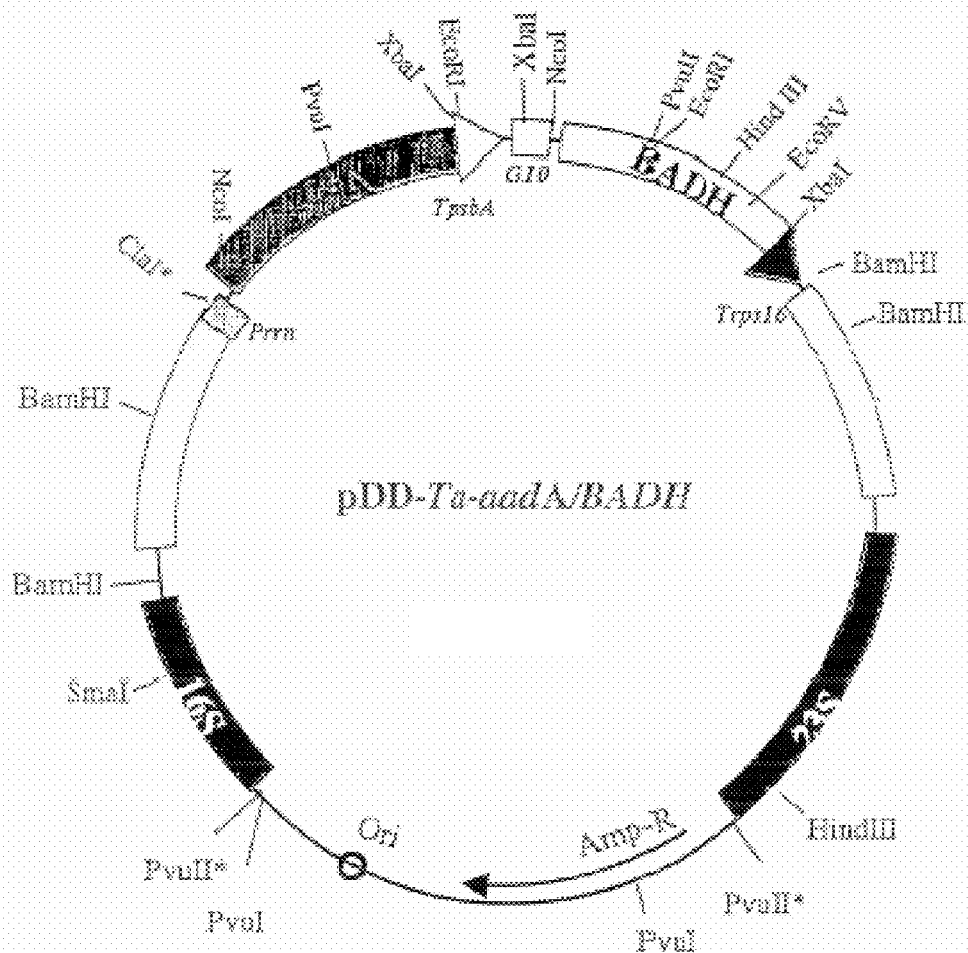
FIG. 25 shows the plasmid pDD-Ta-aadA/BADH. More particularly the plasmid illustrates pDA-29 (aadA/BADH expression cassette), having a backbone vector pBluescript II KS, a selectable marker/host cell Ampicillin/spectinomycinXL-1 Blue MRF' Tc, and a flanking region from *Triticum aestivum* (Ta).
Figure 26:
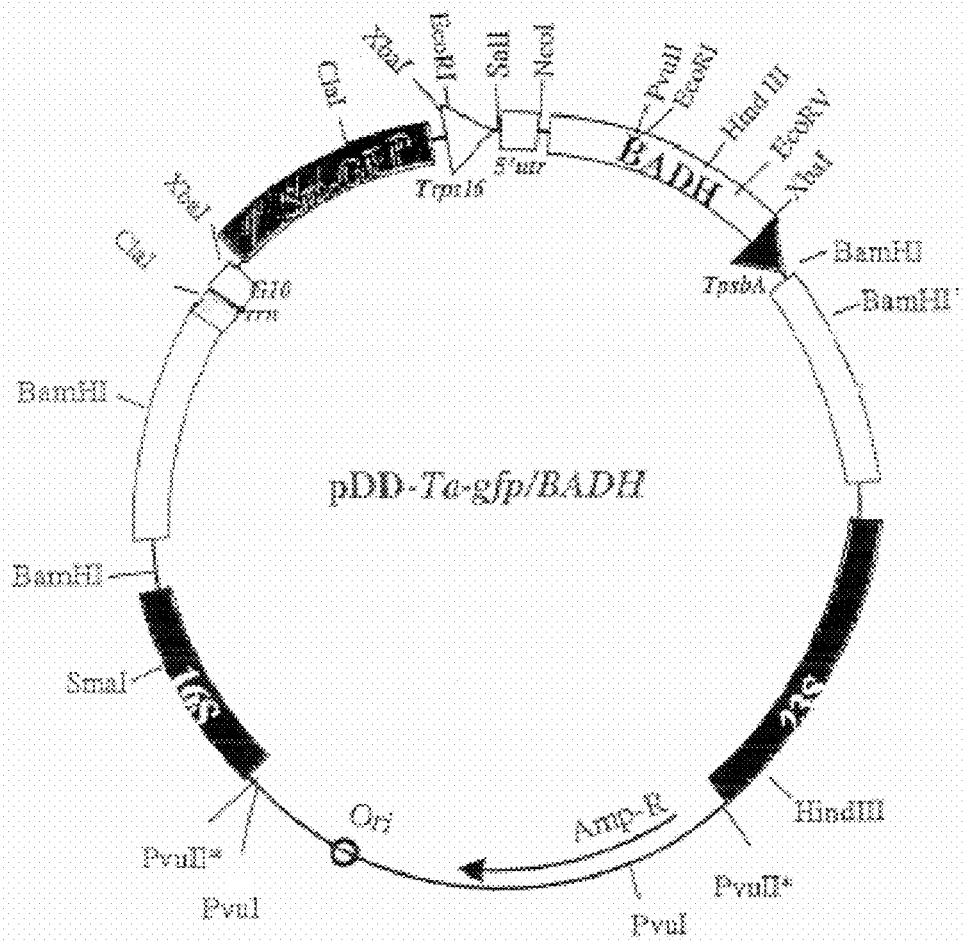
FIG. 26 shows the plasmid pDD-Ta-gfp/BADH. More particularly the plasmid illustrates pDA-30 (gfp/BADH expression cassette), having a backbone vector pBluescript II KS, a selectable marker/host cell Ampicillin/XL-1 Blue MRF' Tc, and a flanking region from *Triticum aestivum* (Ta).
Figure 27:
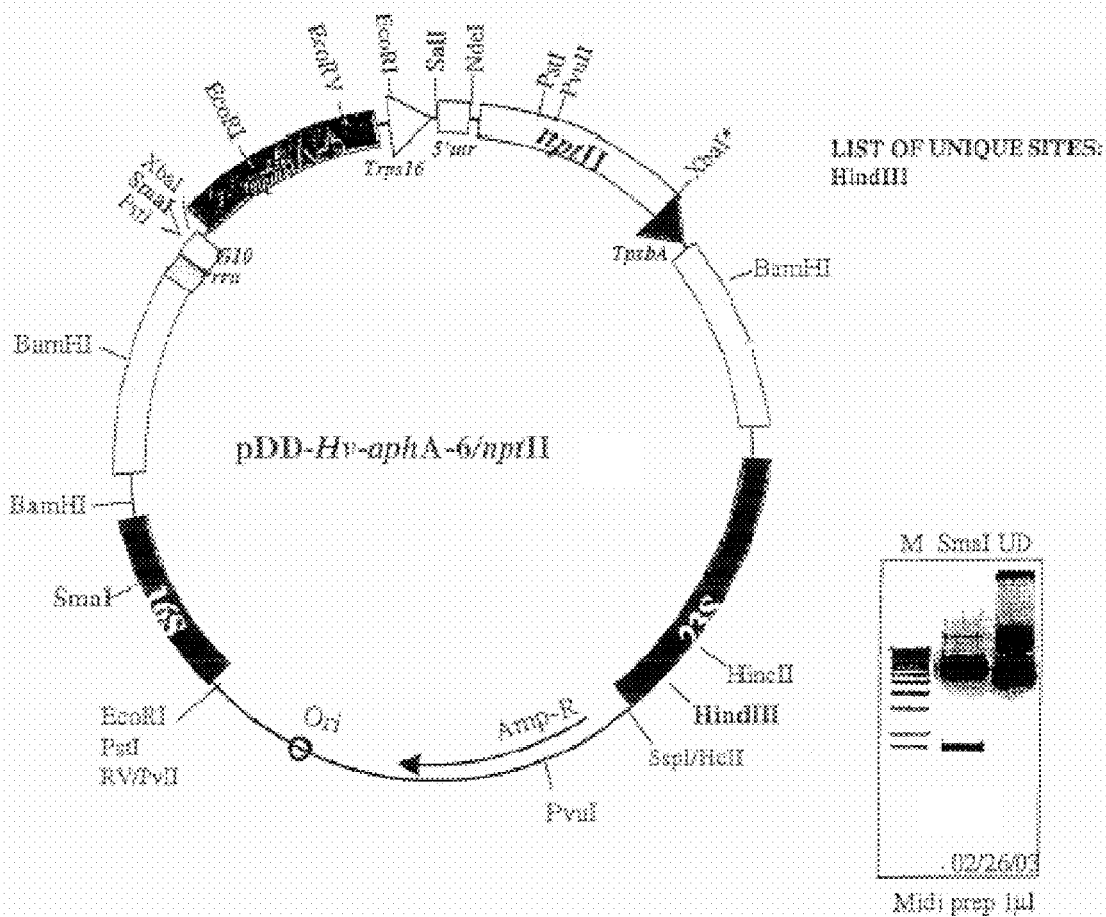
FIG. 27 shows the plasmid pDD-Hv-aphA-6/nptII. More particularly the plasmid illustrates pDA-76 (aphA-6/nptII expression cassette), having a backbone vector pBluescript II KS, a selectable marker/host cell Ampicillin/Kan/XL-1 Blue MRF' Tc, and a flanking region from *Hordeum vulgare* (Hv).
Figure 28:
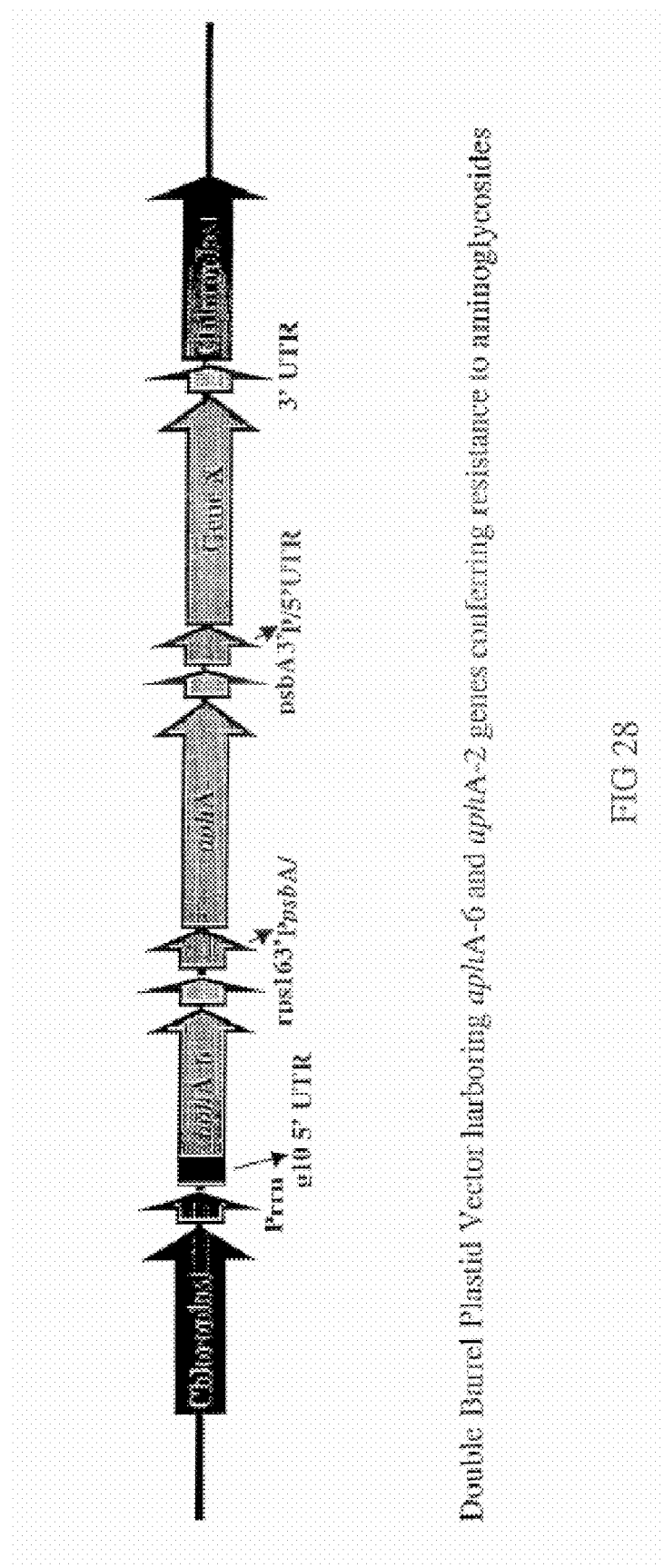
FIG. 28 is a schematic view of a Double Barreled Plastid Vector harboring aphA-6 and aphA-2 genes conferring resistance to aminoglycosides according to the description contained herein.

Different salt concentrations (100-500 mM NaCl) were tested on transformed and untransformed carrot plants transferred to soil in pots. Transgenic plants carrying the badh transgene thrive well up to 400 mM NaCl (FIG. 7), whereas untransformed plants could not survive in pots after two weeks over 200 mM NaCl.

Experimental Protocol.

Construction of Plastid Transformation Vectors.

A DNA fragment representing a carrot flanking sequence was amplified from carrot genomic DNA that was isolated from carrot leaves using DNeasy Plant mini kit (Qiagen Inc.) following manufacturer's protocol. The flanking sequence fragment was amplified with the primers generated from the tobacco chloroplast genome sequence, using Platinum Pfx DNA polymerase (Invitrogen Inc.). The amplified fragment represents the 16S/trnI-trnA/23S region of the chloroplast genome and is approximately 4.2 kb in size. The PCR amplified DNA fragment was treated with T4 polynucleotide kinase (Promega) and cloned into PvuII digested pBluescript II KS, dephosphorylated with Shrimp Alkaline phosophatase (Promega). The kinase and dephosphorylation reactions were performed as per the manufacturer's instructions. The chloroplast promoters and regulatory sequences were amplified using PCR based on the information available for the tobacco chloroplast genome (Accession number—NC_001879). The carrot specific chloroplast transformation vector pDD-Dc-gfp/BADH (FIG. 1A) was constructed by inserting a blunt ended ClaI-SacI fragment representing the gfp/BADH expression cassette into PvuII site of carrot chloroplast DNA flanking sequences. The sm-gfp gene was obtained from TAIR. Similarly, the carrot chloroplast transformation vector pDD-Dc-aadA/BADH (FIG. 1B) was constructed by inserting blunt ended ApaI fragment representing the aadA/BADH expression cassette into carrot chloroplast DNA flanking sequences at the PvuII site, after dephosphorylation. Bacterial and DNA manipulations were performed as per standard molecular biology protocols.

Plant Material Transformation and Regeneration of Transgenic Plants.

Sterile carrot plants (*Daucus carota* L. cv. Half long) were raised in plant tissue culture tubes containing MS salts (Murashige and Skoog, 1962), B5 vitamins (Gamborg et al. 1968), 2% sucrose and 0.8% agar in the medium. The hypocotyls were cut into 0.5 mm segments and placed in 50 ml MSB liquid medium containing 3% sucrose, 0.1 mg/l 2,4-dichlorophenoxyacetic acid (2,4-D) and pH 5.7. After 3 weeks of continuous shaking at 26±2° C. and 120 rpm, liberated cells were collected on a 100 μM mesh, centrifuged (150×g for 10 min) and resuspended in fresh medium. Rapidly growing homogenous yellow cells were subcultured weekly. Fine cell suspension culture of carrot, filtered through a 100 μM mesh, were evenly spread on MSB solid medium supplemented with 3 mg/L 2,4-D and 1 mg/L kinetin and bombarded with carrot specific plastid vectors (FIG. 1A-B). Bombarded calli incubated for 2 days in the dark were selected on MSB medium containing 3 mg/L 2,4-D, 1 mg/L kinetin and different concentrations of betaine aldehyde (10, 15, 20 and 25 mM BA) and spectinomycin (150, 250, 350 and 450 mg/L). Cultures were incubated in 16/8 h day/night cycle at 50-100 1× light intensity and 26±2° C. temperature. Transgenic cultures were multiplied using both solid and liquid medium supplemented with selection agent. Transgenic plants produced through somatic embryogenesis (on MSB medium containing 0.2 mg/L) were transferred to soil in pots. The pots were covered with plastic bags to maintain high humidity for the first week and irrigated with progressively reduced concentrations of MS salts for the first week, followed by tap water in the second week.

DNA Extraction, PCR and Southern Blot Analysis.

Total genomic DNA was isolated using a Plant DNeasy kit (Quiagen Inc. USA) for PCR and Southern blot analysis of transgenic carrot. PCR reactions were performed by denaturing 50 ng DNA template at 94° C. for 5 min, running 25 PCR cycles (1 min at 94° C., 1 min at 64° C., 3 min at 72° C.), final extension at 72° C. for 10 min, using Taq DNA polymerase with 10×PCR buffer and primers pairs 3P/3M (land on flanking sequence/land on aadA gene) and 16SF/1M (landing on the native chloroplast genome/the aadA gene).

For Southern blot analysis, plant DNA was digested with PvuII and AflII and transferred to nylon membranes for hybridizing with a 4.9 kb probe, generated by digesting pDD-Dc-aadA/badh vector DNA with PvuII and AflIII and labeled with $^{32}P$ using the ProbeQuant G-50 Columns (Amersham, USA). Blot was hybridized with probe using the Stratagene Quick-HYB hybridization solution and vender's instructions (Stratagene, USA).

BADH Enzyme Activity and Immunoblot Analysis

Extraction and assay for BADH (Betaine aldehyde dehydrogenase) activity was done as described herein (Daniell et al. 2001). 1 g carrot tissues were grounded in 2 mL buffer containing 50 mM Hepes-KOH (pH 8.0), 1 mM EDTA, 20 mM Sodium metabisulfite, 10 mM Sodium borate, 5 mM ascorbic acid and 5 mM DTT. Crude extract was centrifuged at 10,000×g at 4° C. for 10 min and the supernatant was desalted using Sephadex G-25 Columns (Amersham Pharmacia biotech, USA). $NAD^+$ reduction by BADH was measured spectrophotometrically at 340 nm after 1 min and 10 min in 1 mL assay buffer (50 mM Hepes-KOH, pH 8.0; 1 mM EDTA, 5 mM DTT, 1 mM $NAD^+$) added with 1 mM BA at 25° C. to start reaction.

For immunoblot analysis total soluble protein was isolated using 2× Laemmli buffer from 100 mg carrot tissues. The mixture was boiled for 5 min and centrifuged for 5 min at 10,000×g. Supernatant containing 50 μg total soluble protein (quantified with Bradford assay) was loaded on a 10% SDS-PAGE gel and transferred on blotting membrane. Membrane was hybridized with polyclonal anti-BADH serum, raised in rabbits against BADH (provided by Dr. Elisa Soto). Hybridized peptides were detected using horseradish peroxidase-linked secondary antibody, using Lumi-Phos™ WB chemiluminescent reagent (Pierce, USA).

Analysis of Transgenic Plants for Salt Tolerance.

Transgenic and non-transgenic carrot plants of the same morphogenic growth phase and height were transferred to soil in pots and analyzed for salt tolerance containing 0, 100, 200, 300, 400 and 500 mM NaCl, respectively. Plants were maintained in a growth chamber and irrigated daily with saline water containing different levels of salt for one month.

ILLUSTRATIVE EXAMPLE 2

Cotton Transformation

Material and Methods

Plant Material and Transformation

Delinted cotton (*Gossypium hirsutum* L. cv. Coker310FR) seeds were sterilized by dipping in 70% ethanol for 2 minutes followed an 8 minute treatment with sodium hypochlorite solution containing approximately 4% available chlorine and then by treatment with 0.1% mercuric chloride solution (w/v) for 5 minutes. After surface sterilization and four to five washes with sterile water, seeds were kept in sterile water for 4-5 hours to so ten the seed coat, which was completely removed before the seeds were placed on ½ MSB medium containing half strength MS salts (Murashige and Skoog, 1962) and B5 vitamins (Gamborg et al. 1968) with 1.5% sucrose. Hypocotyl explants (4-6 mm long) of 5 day old seedlings were placed vertically on MST1 medium (containing MS salts, B5 vitamins, 0.1 mg/l 2,4-D, 0.5 mg/l kinetin and 3% glucose) for the induction of callus. Uniformly distributed pro-embryogenic callus were bombarded with gold particles coated with chloroplast vector using the Helium-based biolistics particle gun (Bio-Rad). The transformation of cotton callus was optimized using the parameters: 0.6 .mu.m gold particles macro-carrier; 27 in. Hg chamber vacuum; 1550 psi Helium pressure; 6 mm rupture disc macro-carrier gap; 6 mm macro-carrier flying distance, 6 cm target distance and 10 µl chloroplast vector coated on the gold particles. Cultures after bombardment were incubated in dark for 24 h and thereafter transferred to selection medium MST1 supplemented with 50 mg/l kanamycin and incubated in 16/8 h day/night cycle at 750 lux light intensity and 28.+−2° C. temperature. Transgenic embryogenic cultures were multiplied on MST1 medium supplemented with 50 mg/l kanamycin and transgene aphA-6 gene integration in cultures was confirmed by PCR (FIG. 34). SEQ ID NO. 1 shows the sequence for the aadA/BADH expression cassette.

ILLUSTRATIVE EXAMPLE 3

Expression Cassette Construction

Materials and Methods

Amplification and Cloning of Flanking Sequences

DNA fragment representing flanking sequences were amplified from plant genomic DNA that was isolated from the leaves using Qiagen plant extraction kit following manufacturer's protocol. The flanking sequence fragment was amplified with the primers, ADLF-5' gtgtcagtgtcggcccagcagag 3' and ADLR-5' aacaggggtcaaggtcggccag 3' using Platinum Pfx DNA polymerase (Invitrogen Inc.). The amplified fragment represents the 16S/trnI-trnA/23S region of the chloroplast genome and is approximately 4.2 kb in size. The PCR amplified DNA fragment was treated with T4 polynucleotide kinase (Promega) and cloned into PvuII digested pBluescript II KS dephosphorylated with Shrimp Alakaline phosophatase (Promega). The kinase and dephosphorylation reactions were performed as per the manufacturer's instructions. The clone harboring carrot specific flanking region was designated as pDA-35.

Construction of the Expression Cassettes.

pDA-29 is a chloroplast specific expression cassette cloned in pBluescript II KS that carries the aadA gene conferring resistance to spectinomycin and streptomycin and badh gene that metabolizes the breakdown of toxic betaine aldehyde to glycine betaine. Expression of the first gene is driven by the 16S Prrn promoter, under the regulation of a Shine-Dalgarno sequence at the 5' end and psbA 3' UTR at the 3' end. Expression of badh gene is regulated by heterologous T7 gene 10 5' UTR (also referred to as the gene 10 ribosome binding site) and rps16 3' UTR. The aadA gene was derived from pLD-CtV (Daniell et al. 1998) and the badh gene was derived from pLD-BADH (Daniell et al. 2001). A second chloroplast expression cassette pDA-30 carries the sm-gfp gene encoding for soluble modified green fluorescent protein (obtained from TAIR) and the badh gene. Expression of sm-gfp is driven by the 16S Prrn promoter and is regulated by heterologous T7 gene 10 5' UTR and rps16 3' UTR. The expression of badh gene is regulated by psbA promoter/5' UTR and 3' UTR. The promoters and regulatory sequences were amplified using PCR based on the information available for tobacco chloroplast genome (Shinozaki et al. 1987).

Construction of Chloroplast Transformation Vectors.

Chloroplast transformation vector pDD-XX-aadA/badh is a derivative of pDA vectors that harbor the flanking sequences with the pDA-29 expression cassette. The expression cassette from pDA-29 was obtained as an ApaI fragment, blunt-ended using Klenow DNA polymerase (NEB) as per manufacturer's instructions and cloned into PvuII digested and dephosphorylated pDA-35. The other species specific chloroplast transformation vector pDD-XX-gfp/badh harbors the carrot flanking sequence and the pDA-30 expression cassette. The expression cassette from pDA-30 was derived as a ClaI/SacI fragment, blunt-ended and cloned into PvuII digested and dephosphorylated pDA-35. Bacterial and DNA manipulations were performed as per standard molecular biology protocols.

ILLUSTRATIVE EXAMPLE 4

Corn Transformation

For genetic engineering of the corn chloroplast genome, corn specific sequences flanking the targeted integration site in the corn chloroplast genome (trnI and trnA) were amplified with specific PCR primers and subcloned to flank the betaine aldehyde dehydrogenase (BADH) selectable marker, and green fluorescent protein (GFP) reporter gene expression cassette.

Callus cultures were initiated from aseptically excised immature zygotic embryos (1-2 mm in length), produced on self-pollinated ears of Hill (F1) maize plants. Ears were surface sterilized in a solution containing 2.6% sodium hypochlorite (prepared with commercial bleach) containing 0.1% Tween 20 (polyoxyethylene sorbitan monolaurate) for 20 minutes under continuous shaking, then rinsed 4 times in sterile distilled water. The embryos were then placed on the callus induction medium CI-1, which contained N6 salts and vitamins (463.0 mg/l $(NH_4)_2SO_4$, 2830.0 mg/l $KNO_3$, 400 mg/l $KH_2PO_4$, 166.0 mg/l $CaCl_2$, 185 mg/l $MgSO_4.7H_2O$, 37.3 mg/l $Na_2$-EDTA, 27.85 mg/l $FeSO_4.7H_2O$, 1.6 mg/l $H_3BO_3$, 4.4 mg/l $MnSO_4.H_2O$, 0.8, KI, 1.5 mg/l $ZnSO_4.7H_2O$), 2% sucrose and 1.0 mg/l 2,4-D (2,4 dichlorophenoxy acetic acid), with the rounded scutellar side exposed and the flat plumule-radicle axis side in contact with the medium. Callus cultures were maintained in darkness at 25-28° C. and subcultured every two weeks.

Particle Bombardment of Embryogenic Calli.

Micro projectiles were coated with DNA (pDA34-ZM-gfp-BADH and pDA33-ZM-aadA-BADH) and bombardment was carried out with the biolistic device PDS1000/He (Bio-Rad).

Prior to bombardment, embryogenic calli were selected, transferred over sterile filter paper (Watman No. 1), and placed on the surface of a fresh medium in standard Petri plates (100×15 mm). Gold particles (0.6 μm) were then coated with plasmid DNA as follows: 50 μl of washed gold particles were mixed with 10 μl DNA (1 μg/μl), 50 μl of 2.5M $CaCl_2$, 20 μl of 0.1M spermidine and vortexed. Particles were centrifuged with ethanol for a few seconds at 300 rpm and then the ethanol was poured off. Ethanol washing was repeated five times, then the pellet was resuspended in 30 μl of 100% ethanol and placed on ice until it was used for bombardment (the coated particles were used within 2 hours). Bombardment was carried out with the biolistic device PDS1000/He (Bio Rad) by loading the target sample at level 2 in the sample chamber under a partial vacuum (28 inches Hg).

The callus cultures were bombarded with the maize chloroplast transformation vectors using 1100 psi rupture discs. Following bombardment, the explants were transferred to a fresh medium; plates were sealed with micropore tape and incubated in darkness at 25-28° C.

Selection.

Selection was initiated two days after bombardment. The bombarded calli were transferred to callus induction medium containing 5-20 mM BA (betaine aldehyde) or 25-100 mg/l streptomycin. Selection was also carried out using 50-150 mM NaCl in combination with the BA to maintain osmotic pressure.

Regeneration.

Regeneration was initiated 6 to 8 weeks after bombardment by transferring the calli to a medium R1 containing MS salts and vitamins supplemented with 1.0 mg/l NAA α-naphthalene acetic acid), 2% sucrose, 2 g/l myoinositol and 0.3% phytagel at pH 5.8. Regenerated plants were transferred to R2 containing ½ MS salts and vitamins, 3% sucrose and 0.3% phytagel at pH 5.8. Regenerated plants were maintained in light (16/8 hr photoperiod).

Shoot Multiplication.

The Surface Sterilization and Germination of Corn Seeds.

Corn seeds were surface sterilized in a solution containing 2.6% Sodium hypochlorite (prepared from commercial bleach) containing 0.1% Tween 20 for 20 minutes under continuous shaking, then rinsed four times in sterile distilled water. Seeds were grown on MS medium at pH 5.8 in darkness. Nodal sections were excised aseptically from three day old seedlings. The nodal sections appeared as clear demarcations on the germinated seedlings and represented the seventh node. When excised, the nodal cross sections were 1.3 to 1.5 mm in length.

Particle Bombardment of Nodal Sections.

Prior to bombardment, 20-30 nodal sections were placed in the center of each petri plate with acropitila end up. Bombardment was carried out with the maize chloroplast vectors, using 1100, 1300 and 1550 psi rupture discs.

Multiple Shoot Induction and Selection

Nodal section explants were placed acropital end up on shoot multiplication medium SM1 composed of MS salts and vitamins, 1.0 mg/l 6BA (6-Benzyl amino purine), 3% sucrose and 5 g/l phytagel at pH 5.8 under continuous light at 25° C. Initiation of the shoot-tip clumps from the original shoot tips occurred 2 to 4 weeks after culture. Two days after bombardment, transformed nodal sections were transferred to shoot multiplication medium containing 5-20 mM BA or 50-100 mg/l streptomycin selective agents. Subsequent subcultures at two week intervals were carried out by selecting, dividing and subculturing green clumps on selective shoot multiplication medium containing 5-20 mM BA or 25-100 mg/l streptomycin.

Regeneration.

The Multiple shoot clumps were regenerated by transferring them to regeneration medium M1 containing MS salts and Vitamins, 5 mg/l IBA and 3% sucrose at pH 5.8. The developed shoots were regenerated by transferring the shoot tip clumps to M2 medium containing ½ MS salts and vitamins, 3% sucrose and 3 g/l phytagel at pH 5.8. It should be further noted that all the regeneration media are supplemented with 5-20 mM BA or 25-100 mg/l streptomycin as the selective agents.

To engineer the corn chloroplast genome free of antibiotic resistance genes, maize calli were bombarded with a chloroplast expression vector containing the green fluorescent protein (GFP) and the betaine aldehyde dehydrogenase (BADH) genes as selectable or screenable markers. To compare the betaine aldehyde (BA) selection with streptomycin, another chloroplast expression vector was constructed containing the aadA and the BADH genes. The number of putative transgenic events was higher on BA selection than on streptomycin. Transgenic corn tissues screened on BA were examined using a laser-scanning confocal microscope. The GFP fluorescence was observed throughout the somatic embryos of corn. Chloroplast transformation of corn provides a suitable avenue for the production of edible vaccines and oral delivery of biopharmaceuticals.

Corn Chloroplast Transformation Vector.

Corn chloroplast transformation vector facilitates the integration of transgene into the inverted repeat (IR) region of the corn chloroplast genome. The vector pLD-Corn-BADH contains the chimeric aadA gene and the BADH gene driven by the constitutive 16 S rRNA promoter and regulated by the 3' UTR region of psbA gene from the petunia plastid genome. In this construct, both aadA and BADH possess the chloroplast preferred ribosomal binding site, GGAGG. Another vector used for corn chloroplast transformation pLD-corn-UTR-BADH has the constitutive 16 S rRNA promoter driving the expression of the dicistron, but BADH is under the regulation of the promoter and the 5' UTR of the psbA gene and the 3' UTR of psbA gene, for enhanced expression. Since the expression of the foreign protein is desired in chromoplasts of corn seeds, the gene of interest needs to be under the control of a regulatory sequence that is free from cellular control. In this context, examples of suitable candidate regulatory sequences are the T7 gene 10-leader sequence and cry2Aa2 UTR. The T7 gene 10-leader sequence is used to express foreign proteins in transgenic chromoplasts. The cry2Aa2 UTR has been shown by the inventor to accumulate as much foreign protein in chromoplasts as efficient as the psbA UTR in green tissues. Therefore, the selectable marker for additional vectors uses the BADH gene under the regulation of psbA promoter and 5' UTR, as psbA is one of the most efficiently translated chloroplast genes in green tissues. When green tissue or non-green embryogenic calli are used for introducing the transgene into the corn chloroplast genome, it is preferred to use the light regulated psbA promoter/UTR or 16 S rRNA promoter/gene 10 UTR, respectively.

EXAMPLE 5

Double Barrel Plastid Vectors

This example will help in understanding the plasmids shown in FIG. 9-28. For many crops, including monocots, cultured non-green cells or other non-green plant parts are used as explants for the transformation of plastids. These non-green tissues contain proplastids instead of chloroplasts, in which gene expression and gene regulation systems are quite different. After transformation, transformed proplastids will develop into mature plastids, such as for example, chloroplasts, and transformed cells will survive the selection process during all stages of development. Therefore, the major challenge is to provide plastids the ability to survive selection in the light and the dark, at different developmental stages, such as for example, in both green and non-green tissues. This is absolutely critical because only one or two chloroplasts are transformed in a plant cell and these plastids should have the ability to survive the selection pressure, multiply and establish themselves while all other untransformed plastids are eliminated in the selection process. The Double Barrel Plastid Vectors accomplish this by using genes coding for two different enzymes capable of detoxifying the same selectable marker (or spectrum of selectable markers), driven by regulatory signals that are functional in proplastids as well as in mature chloroplasts and where at least one of the selectable marker genes is always expressing in both light and dark conditions.

The plastid vector described here is one among several such examples (non-limiting example). The chloroplast flanking sequences contains appropriate sequences homologous to the plastid genome so that the transgene cassette is inserted into a spacer region. Any spacer region or sequence within the plastid genome could be targeted for transgene integration, including transcribed and transcriptionally silent, spacer regions. Preferably transcriptionally active spacer regions are targeted. Both aphA-6 and aphA-2 (nptII) genes code for enzymes that belong to the aminoglycoside phosphotransferase family but they originate from different prokaryotic organisms. Because of the prokaryotic nature of the chloroplast genome, these genes are ideal for use in transgenic chloroplasts without any codon optimization or modification. Genes of prokaryotic origin have been expressed at very high levels in transgenic chloroplasts (up to 47% of total soluble protein, DeCosa et al., 2001).

Both enzymes have similar catalytic activity but the aphA-6 gene product has an extended ability to detoxify kanamycin and provides a wider spectrum of aminoglycoside detoxification, including amikacin. The advantage of choosing kanamycin as a selectable marker is that it has no natural resistance, unlike spectinomycin resistance observed in most monocots or spontaneous point mutation of the 16 S rRNA gene observed during the selection process. In addition, kanamycin is not in human clinical use as an antibiotic and several crops containing kanamycin resistant nuclear transgenes have been already approved by FDA for human consumption (e.g. flavor savor tomatoes) and currently in the market place.

In this non-limiting example, all transgenes are regulated by the plastid Prrn promoter; this 16S rRNA promoter drives the entire rRNA operon in the native chloroplast genome and contains binding sites for both the nuclear encoded and plastid encoded RNA polymerases. Therefore, this promoter is capable of functioning in both proplastids and chloroplasts (green and non-green, in the light and dark). The aphA-6 gene is further regulated by the gene 10 5' UTR capable of efficient translation in the dark, in proplastids present in non-green tissues (see GFP expression in proplastids of non-green cells of corn and carrot in FIGS. 31 and 2 regulated by the 16S rRNA promoter and gene 10 UTR). The rps16 3' UTR has been used to stabilize aphA-6 gene transcripts. The aphA-2 (nptII) gene, on the other hand is regulated by the psbA promoter, 5' and 3' UTRs, which are light regulated and highly efficient in the light, in chloroplasts (see A. Fernandez-San Millan, A. Mingeo-Castel, M. Miller and H. Daniell, 2003, A chloroplast transgenic approach to hyper-express and purify Human Serum Albumin, a protein highly susceptible to proteolytic degradation. Plant Biotechnology Journal, in press; also see WO 01/72959). Therefore, a combination of both aphA-6 and aphA-2 genes, driven by regulatory signals that function in the light and in the dark in both proplastids and chloroplasts, provides continuous protection for transformed plastids/chloroplasts around the clock from the selection agent. The gene (s) of interest with appropriate regulatory signals (gene X) are inserted downstream or upstream of the double barrel selectable system.

Because multiple genes are inserted within spacer regions (DeCosa et al 2001, Daniell & Dhingra, 2002), the number of transgenes inserted does not pose problems in transcription, transcript processing or translation of operons (WO 01/64024). In a variation of this example, aphA-6 and aphA-2 genes, coupled with different transgenes are inserted at different spacer regions within the same chloroplast genome using appropriate flanking sequences and introduced via co-transformation of both vectors.

EXAMPLE 6

Cotton Transformation

6a. Construction of Cotton Plastid Transformation Vectors

DNA fragment representing cotton flanking sequence was amplified from cotton genomic DNA that was isolated from the leaves using DNeasy Plant mini kit®. The flanking sequence fragment was amplified with the primers designed based on tobacco chloroplast genome sequence information using Platinum Pfx DNA polymerase®. This Pfu based enzyme has been demonstrated to be more efficient than Pfu DNA polymerase and it has the lowest error rate at roughly $1.3 \times 10^{-6}$ error per base pair. The forward primer, ADLF and the reverse primer, ADLR amplified a 4.0 kb DNA fragment representing the 16S/trnI-trnA/23S region of the cotton chloroplast genome. The PCR amplified DNA fragment was treated with T4 polynucleotide kinase and cloned into PvuII digested pBluescript II KS, dephosphorylated with Shrimp Alkaline phosphatase. The kinase and dephosphorylation reactions were performed as per the manufacturer's instructions. The chloroplast promoters and regulatory sequences were amplified using PCR based on the information available for the tobacco chloroplast genome (Accession # NC_001879). The primers used were as follows: ADLF (5'CACTCTGCTGGGCCGACACTGACAC 3'; SEQ ID NO:4); ADLR (5'CACTAGCCGACCTTGACCCCTGTT 3'; SEQ ID NO:5); Prrn (Forward: 85'ATCGATGAGC CTGAT-TATCCTAAG3'; SEQ ID NO:6; Reverse 5'CAGCAGGTA-GACAAAGCGGATTC_3'; SEQ ID NO:7), PpsbA (Forward 5'GATATCGTCGACGTAGAGAAGTCCG 3'; SEQ NO:8; Reverse 5'CATATGAAAA TCTTGGTTTATTTAA 3': SEQ ID NO:9); TpsbA (Forward 5'TCTAGAGCGATC-CTGGCCTAG_3': SEQ ID NO:10; Reverse 5'_GAGCTCG-CAGCCAA ACAAATAC 3'; SEQ ID NO:11); Trps16 (Forward 5'ACTAGTCCTAATCAACCGAAATTC_3'; SEQ ID NO:12; Reverse 5'GAGCTCGAACACGGAATTCAATG- GAAGC_3'; SEQ ID NO:13); T7 gene 10 (Forward 5'GGTAACCCCGGGAGACCACAACGGTTTC-CCTCTAGAAATAATTTT GTTTA3'; SEQ ID NO:14; Reverse 5'CATATGTATATCTCCTTCTTAAAGTTA_3'; SEQ ID NO:15); 3P (5'_AAAACCCGTCCTCAGTTCG-GATTGC_3'; SEQ ID NO:16); 16S F (5'CAGCAGCCGCG-GTAATACAGAGGA_3'; SEQ ID NO:17); aphA-6 Rev (5'_CGAGAGACAC ACTGTATGTGGTCTCTG_3'; SEQ ID NO:18).

The cotton specific chloroplast transformation vector pDD-Gh-aphA-6/nptII (FIG. 39A) was constructed by inserting a blunt ended fragment representing the aphA-6/nptII expression cassette into PvuII site of cotton chloroplast DNA flanking sequences. This site is present in the intergenic region between the trnI-trnA genes in the cloned flanking region. The chloroplast vector pKD-Gh-aphA-6 (FIG. 39B) was constructed by excising the nptII-coding region along with the psbA 3' UTR from pDD-Gh-aphA-6/nptII and cloning a PCR generated fragment representing a multiple cloning site (MCS) and psbA 3' UTR. For this PCR following primers were used: forward primer 5'TTAACATATGAGGC-CTTAGAGCGATCCTGGC 3': SEQ ID NO:19: and reverse primer 5'CAATTGCAAGAGCGGAGCTCTACCAAC 3'; SEQ ID NO:20. All general bacterial and DNA manipulations were performed as per standard molecular biology protocols.

6b. Transformation and Regeneration Protocol for Cotton.

Cotton grayish-green friable callus produced from hypocotyls explants of 5-days-old seedlings of cotton cultivar Coker310FR were uniformly placed on sterile filter paper in petri-plate containing MST1 medium (MS salts, B5 vitamins, 0.1 mg/l 2,4-D, 0.5 mg/l kinetin and 3% glucose) and bombarded with gold particle coated with chloroplast vector pDD-Gh-aphA6/nptII, using the helium-driven biolistic particle delivery system. Cultures, after bombardment, were incubated in the dark for 24 h and thereafter transferred to selection medium MST1 supplemented with 50 mg/l kanamycin and incubated in 16/8 h day/night cycle at 50 µE light intensity and about 27±1° C. temperature. Transgenic chloroplast cultures were multiplied on MST1 medium supplemented with 100 mg/l kanamycin. Cotton callus culture were maintained for from about 4 to about 5 months on MST1 containing kanamycin before they were plated on induction medium to produce somatic embryos. Transformed callus was converted into somatic embryos and plantlets on MST0 medium (MS salts, B5 vitamins) containing 1.9 g/l extra potassium nitrate. PCR confirmed transgenic plantlets were transferred to growth chamber for flowering and set seeds.

6c. Optimization of Transformation Parameters in Cotton.

For optimization of gene delivery, cotton calli were placed on Whatman # 1 filter paper, supported by MST1 medium. Gene delivery was optimized using pDD-Gh-aphA6/nptII vector for cotton cell cultures coated on 0.6 µm gold particles using different rupture discs and at different distances between rupture discs and target tissues. Bombarded calli, after two-days of dark incubation, were plated on MST1 selection medium containing 50 mg/l kanamycin. Kanamycin resistant transgenic calli obtained from cotton cell cultures were tested for site-specific integration of transgenes into plastid genomes by PCR.

6d. Analysis of Maternal Inheritance in Cotton.

Emasculated non-transgenic cotton plants were hybridized with pollen of chloroplast transgenic cotton plants. Hybrid F1 (non-transgenic versus. transgenic) as well as chloroplast transgenic cotton seeds were germinated on ½ MS basal medium supplemented with 50 mg/l kanamycin.

6e. Construction of Cotton Plastid Transformation Vectors

Cotton chloroplast vectors target the expression cassette to the 16S/trnI-trnA/23S region of the chloroplast genome for integration via homologous recombination. The site of integration is similar to the universal chloroplast transformation vector (pLD CtV) reported earlier from our laboratory. For the construction of cotton specific chloroplast transformation vector, flanking region was amplified from cotton genomic DNA. In the absence of chloroplast genome sequence information for cotton, primers were designed based on the sequence information available for tobacco. PCR amplification of flanking region from cotton resulted in a 4.0 kb DNA fragment that is approximately twice the size of flanking region used in pLD CtV vector. It has been shown that frequency of homologous recombination is dependent on the length and homology of the flanking sequences. Based on these observations, the length of the flanking sequences was increased to 2 kb each on either side of the transgene cassette so that it might enhance the frequency of homologous recombination. Cotton specific chloroplast transformation vector (pDD-Gh-aphA-6/nptII; see FIG. 39A) harbors the aphA-6 gene regulated by the 5' ribosome binding site (rbs) region of the bacteriophage T7 gene 10 leader/rps16 3' UTR in order to facilitate expression in green as well as non-green tissues. The nptII gene expressed under the PpsbA 5' UTR and 3' psbA UTR in order to facilitate light regulated expression in green tissue. The second cotton specific chloroplast transformation vector (pKD-Gh-aphA-6; see FIG. 1B) harbors only the aphA-6 gene driven by the 16S rRNA full length promoter and regulated by T7 gene 10 5' UTR/rps16 3' UTR. A PpsbA 5' UTR and psbA 3' UTR with a multiple cloning site in between UTRs was inserted in order to clone genes of interest. Transcription of the expression cassettes in the cotton chloroplast transformation vectors is driven by the full-length 16S rRNA promoter. The full-length promoter comprises of binding sites for both the plastid-encoded and nuclear-encoded RNA polymerase thereby facilitating transcription in green or non-green tissues. All the 5' and 3' regulatory elements were PCR amplified from the tobacco genomic DNA except for the T7 gene 10 5' UTR which was PCR amplified from pET 11 vector (NEB).

6f. Transformation of Cotton Plastids and Plant Regeneration

Embryogenic cell cultures serve as an ideal target material for biolistic transformation. However, cotton is particularly challenging to manipulate in-vitro due to the difficulties encountered in plant regeneration through somatic embryogenesis. Coker cultivars used for in vitro regeneration are highly variable in their embryogenic response due to genotype specificity, which has impacted the efficacy of genetic transformation through somatic embryogenesis. Nuclear transformation of elite cotton depends mainly on Coker cultivars, used as the source for in vitro transformation. Availability of pure embryogenic line (Coker 310FR; fully regenerating) was reported to improve the transformation frequency as well as regeneration of transgenic cotton plants. Friable grayish callus induced from hypocotyl segments of fully embryogenic cotton was bombarded with cotton chloroplast vector pDD-Gh-aphA6/nptII as described. Cotton plastid transformation was attempted using the aadA gene containing cotton chloroplast vectors. 105 cotyledons, 60 leaves and 72 plates of embryogenic callus (1 mm thick layer×20 mm in diameter) were bombarded with spectinomycin containing cotton specific chloroplast vector. Bombarded cotyledons, leaves were cut into small pieces and calli cultures were equally plated on selection medium containing 25, 75 and 150 mg/l spectinomycin. However, no transgenic calli or plants were recovered over a period of 6 months using spectinomycin as the selection agent due to its lethal effect on cotton cultures.

Embryogenic cotton calli bombarded with chloroplast vector pDD-Gh-aphA6/nptII produced several transgenic lines (FIG. 37), selected on MST1 medium containing 0.1 mg/l 2,4-D and 0.5 mg/l kinetin (callus induction medium) and supplemented with 50 mg/l kanamycin. See FIGS. 41A and 41B. Further, transformed cultures were multiplied on higher concentrations of kanamycin (100 mg/l) in order to increase the number of transgenic chloroplasts in cotton cultures. Transgenic somatic embryos were induced from calli on basal MST0 medium (containing 1.9 g/l extra KNO3) supplemented with 25 mg/l kanamycin in about 3 months. Transgenic embryos placed on Whatman filter paper (No. 1) in a petri-dish containing MST0 medium, were matured and elongated into plantlets in about 1 month. See FIG. 38D. Transgenic cell cultures and plantlets were tested for stability of site-specific transgene integration using PCR and southern blotting. Confirmed transgenic plants were transferred to growth chamber for flowering and setting seeds.

6g. Optimization of Plastid Transformation.

Plastid transformation efficiency is very high in tobacco (approximately 5-15 events per bombarded leaf) but has been less efficient in other crops, including other *Solanaceous* species. Plastid transformation protocol was optimized to enhance efficiency in cotton and bombardment conditions. The first nuclear transformation of cotton via somatic embryogenesis using particle gun was demonstrated with 0.7% efficiency. In order to optimize gene delivery in cotton chloroplasts, pDD-Gh-aphA6/nptII was bombarded using different rupture discs, varying distances between rupture discs and target tissues. Maximal transformation efficiency (41.7% or 1 transformation event per 2.4 bombarded plates) was observed when cell cultures (friable; gray in color) were bombarded at 9 cm distance with 650-psi rupture disc (FIG. 37). These results suggest that higher cell death or production of phenolic compounds at sites of injury may be important determinants in transformation efficiency. The use of double gene single selection (DGSS) plastid vector greatly facilitated optimization of bombardment parameters, transformation conditions and facilitated chloroplast transformation even with a single gene (aphA-6) single selection vector (SGSS). Using these optimized conditions, chloroplast vector with a single selectable marker gene (aphA-6 gene) yielded only two transformation events out of 40 bombarded plates (FIG. 37). The transformation efficiency with the double selectable marker gene is 8-fold more than single selectable marker gene. The cotton chloroplast vector pDD-Gh-aphA6/nptII integrates the aphA6 and nptII genes into the 16S-23S-spacer region of the plastid genome by homologous recombination. Integration of aphA6 and nptII into the cotton cultures was confirmed by PCR using internal primers 3P (anneals to the flanking sequence) and aphA6-rev (anneals to the aphA6 coding region). A 2.1 kb size PCR product was amplified, which confirmed integration of the transgenes in different cell cultures of cotton. In order to distinguish between nuclear and chloroplast transgenic lines, 16S-F primer was designed to anneal to the native chloroplast genome, 200 by upstream of integration site and aphA6-rev primer was designed to anneal to the aphA6 transgene; this yielded a 2.6 kb size PCR product, which confirmed the plastid specific integration of the transgenes into cotton chloroplast genome. Since this PCR product can be obtained in the event of nuclear integration mediated by promiscuous DNA, the possibility of nuclear integration was eliminated by Southern analysis. Transgenic calli selected after bombardment of pKD-Gh-aphA-6 (containing single aphA-6 marker gene) on MST1 medium supplemented with 50 mg/l kanamycin produced two transgenic lines. Transgene integration was again confirmed using different sets of primers: 3P and apbA6-rev; 16SF and aphA6-rev.

Transgene integration was again confirmed using different sets of primers: 3P and aphA6-rev; 16SF and aphA6-rev. Transgenes (aphA-6 and nptII) integration into cotton plastid genome and homoplasmy were investigated by Southern blot analysis. Genomic DNA from transformed and untransformed cultures was digested with appropriate restriction enzymes, transferred to nitrocellulose membrane and probed with p32-radiolabeled aphA-6 gene fragment (~650 bp, digested with Pstl and EcoRV from pDD-Gh-aphA6/nptII). Transformed chloroplast genomic DNA digested with PvuII and EcoRV yielded an expected 3.3 kb size hybridization fragment, confirming site-specific stable integration of the transgenes into the chloroplast genome in cell cultures and cotton plants. As expected, no fragment hybridizing with the aphA-6 probe was observed in the wild-type untransformed cotton chloroplast genome. Southern blot analysis was performed using total genomic DNA isolated from untransformed and transgenic cotton lines and calli derived from transgenic somatic embryos. In order to investigate heteroplasmy or homoplasmy, genomic DNA of cotton plants transformed with pDD-Gh-aphA6/nptII was digested with BamHI and HindIII and hybridized with the 1.4 kb radioactive flanking DNA probe (isolated from chloroplast vector containing only flanking region with BamHI and HindII). The BamHI and HindIII digested genomic DNA blot showed a 4.0 kb fragment containing flanking sequences as well as transgene sequences in the homoplasmic transgenic lines. The wild type untransformed cotton yielded a 1.4 kb fragment containing flanking sequences. Heteroplasmic transgenic cotton lines should yield both fragments of 4.0 kb and 1.4 kb. Homoplasmic transgenic cotton lines were selected by repetitive subcultures of callus induced from hypocotyls segments of elongated somatic embryos that were regenerated after four cycles of subcultures. All transgenic calli were repeatedly subcultured on MST1 medium containing 100 mg/l kanamycin. This helps to eliminate the untransformed chloroplasts from putative transgenic cotton cell cultures.

6h. Determination of Maternal Inheritance in Cotton.

In vitro produced transgenic cotton lines were grown in the growth chamber along with non-transgenic plants, under similar growth conditions. Growth of chloroplast transgenic lines (FIG. 42A), onset of flowering, floral parts, boll formation and seed setting (FIGS. 42C, D and E) were similar to the untransformed cotton plants (FIGS. 42B, F and G). Cotton lines were grown to maturation stage in the growth chamber and crosses were made between emasculated flowers of non-transgenic cotton and pollen grains from chloroplast transgenic lines. More than 150 seeds from F1 crosses (non-transgenic versus transgenic chloroplast) were germinated on 1½ MS medium supplemented with 50 mg/l kanamycin. Seedlings from F1 crosses (non-transgenic versus transgenic chloroplast) germinated on kanamycin selection medium but failed to grow further, where as transgenic chloroplast seeds germinated well, produced copious roots and leaves, confirming resistance to kanamycin. This demonstrates that there is no paternal inheritance in cotton and that the chloroplast transgenic trait is inherited maternally. All seeds derived from self-pollinated chloroplast transgenic plants germinated on kanamycin and therefore, no Mendelian segregation was observed in the tested seeds. Uniparental maternal inheritance of cotton plastid genome has been reported earlier where the mechanism of maternal inheritance was investigated in depth and established.

The present invention provides a reproducible process for generating cotton plastid transgenic lines from transformed callus via somatic embryogenesis. The vectors employed for chloroplast transformation of potato, tomato and *Lesquerella* contained the flanking sequences from tobacco or *Arabidopsis*. Efficient transformation of carrot chloroplast genome (1 event per ~7 bombarded plates) using species-specific chloroplast vector containing 100% homologous flanking have been used for demonstration of plastid transformation, especially in recalcitrant crops. The origin of replication has been mapped in tobacco chloroplast genome and it is located in the trnI gene that forms the left flank in the chloroplast transformation vector used for cotton chloroplast transformation. When chloroplast vectors with or without ori were bombarded into cultured tobacco cells only the vector with ori located within the trnI gene showed prolonged and higher levels of CAT enzyme. When chloroplast vectors with or without ori were bombarded with the same transgenes, the vector with ori present within the trnI flanking region achieved homoplasmy even in the first round of selection. Higher transformation efficiency observed in cotton might be due to the use of long homologous (100%) flanking sequences that contain the complete chloroplast origin of replication offering large number of templates within plastids and help to achieve homoplasmy even in the first round of selection. Because most of the crop species are regenerated via somatic embryogenesis, methods developed in embodiments of the present invention can be used in transforming the plastid genomes of other crop plants. Non-green tissues contain several kinds of plastids namely proplastids, leucoplasts, amyloplasts, etioplasts, chromoplasts, elaioplasts and gerontoplasts in which gene expression and gene regulation systems are quite different from green chloroplasts. During transformation, transformed proplastids should develop into mature chloroplasts and transformed cells should survive the selection process during all stages of development. The present invention provides plastids an ability to survive selection in the light and the dark, and at different developmental stages. Only one or two chloroplasts are transformed in a plant cell after bombardment and these plastids should have the ability to survive the selection pressure, multiply and establish themselves while all other untransformed plastids are eliminated in the selection process. The DGSS plastid vector accomplishes this by using genes coding for two different enzymes capable of detoxifying the same selection agent (or spectrum of selection agents), driven by regulatory signals that are functional in proplastids as well as in mature chloroplasts. Both aphA-6 and aphA-2 (nptII) genes code for enzymes that belong to the aminoglycoside phosphotransferase family but they originate from different prokaryotic organisms. Both enzymes have similar catalytic activity but the aphA-6 gene product has an extended ability to detoxify kanamycin and provides a wider spectrum of aminoglycoside detoxification, including amikacin.

In nuclear genetic engineering, a majority of the crop species have been transformed using aminoglycoside detoxification (kanamycin for dicots and geneticin for monocots). Both transgenes (aphA2 (nptII), aphA6) are transcribed by the full-length plastid Prrn promoter containing binding site for nuclear-encoded and plastid-encoded RNA polymerase and is expected to function both in proplastids and mature chloroplasts. The aphA-6 gene is further regulated by the T7 gene 10 5'UTR capable of efficient translation in the dark, in proplastids present in non-green tissues (i.e. grayish friable culture of cotton initially bombarded with cotton specific chloroplast vector). The rps16 3'UTR was used to stabilize aphA-6 gene transcripts. The T7 gene 10 5' UTR and rps16 3' UTR facilitated 74.8% transgene expression in non-green edible parts (carrots) containing chromoplasts and 48% in proplastids, compared to chloroplasts in leaves. The aphA6 gene is expressed in non-green and green plastids in the light or dark. The nptII gene in the cotton plastid transformation vector is driven by the psbA 5' and psbA 3' UTRs, which have been repeatedly shown to be responsible for light regulated expression of transgenes integrated into the plastid genome. It is logical to expect breakdown of kanamycin in both dark and light conditions. A combination of both aphA-6 and aphA-2 genes, driven by regulatory signals in the light and in the dark, in both proplastids and chloroplasts, provides continuous protection for transformed plastids/chloroplasts from the selectable agent. These approaches helped in the optimization of transformation procedure of cotton cell culture and achieve a high frequency of transformation. Such optimized conditions further helped to obtain transformation even with a single selectable marker aphA-6. The presence of two antibiotic resistance genes should not pose any problem because several methods are currently available to eliminate marker genes from transformed chloroplast genomes. The number of independent resistant calli obtained with pDD-Gh-aphA-6/nptII vector is shown in the Table 1 in FIG. 37. All of these independent resistant calli tested positive by PCR without any escape or mutation. Therefore all tested lines were plastid transformants. Out of seven lines tested by Southern blots for site-specific integration, three cell lines showed best morphogenic response. These cultures were chosen to produce elongated somatic embryos. Hypocotyl of elongated embryos were dissected into small pieces to induce callus and somatic embryos. Plants produced from first two lines were grown in the growth chamber. T1 seedlings from these lines were tested by Southern blots and showed homoplasmy. Third line maintained in vitro in the callus form, derived from hypocotyl of elongated somatic embryos was also observed to be homoplasmic. About 5-20 somatic embryos were derived from transgenic calli after each subculture, generating several transgenic plants from a single culture.

Transgenic calli selected (on MST1 medium containing 50 mg/l kanamycin) for 8 weeks after bombardment and repeatedly subcultured every month (4 times) on higher selection medium (100 mg/l kanamycin), in order to increase the number of transgenic chloroplasts in cell cultures (visually green in color). To induce the somatic embryogenesis, cell cultures were plated for 3 months on medium (MST0+25 mg/l kanamycin) and well-differentiated somatic embryos were elongated on a Whatman #1 filter paper placed on medium (MST0+25 mg/l kanamycin) for a month. Further, hypocotyls of elongated somatic embryos were dissected into small pieces and placed on selection medium (MST1+100 mg/l kanamycin) for two months to induce the callus. Induced callus was again plated for induction of embryos and subsequently for elongation of somatic into plantlets. It took about 18 months to obtain a homoplasmic transgenic plant from the bombarded pro-embryogenic cotton calli, a slow but reproducible process.

EXAMPLE 7

Carrot Transformation with aadA Gene and BADH Gene

A. Construction of Carrot Plastid Transformation Vector.

DNA fragment representing carrot flanking sequence was amplified from carrot genomi DNA that was isolated from the leaves using DNeasy Plant mini kit®. The flanking sequence fragment was amplified with the primers designed based on tobacco chloroplast genome sequence information using Platinum Pfx DNA polymerase® The forward primer, ADLF and the reverse primer, ADLR amplified a 4.0 kb DNA fragment representing the 16S/trnI-trnA/23S region of the carrot chloroplast genome. The PCR amplified DNA fragment was treated with T4 polynucleotide kinase and cloned into PvuII digested pBluescript II KS, dephosphorylated with Shrimp Alkaline phosphatase. The kinase and dephosphorylation reactions were performed as per the manufacturer's instructions. The chloroplast promoters and regulatory sequences were amplified using PCR based on the information available for the tobacco chloroplast genome (Accession # NC_0018791). The primers used were as follows:

```
ADLF
(5' CACTCTGCTGGGCCGACACTGACAC 3'
SEQ ID NO: 4);

ADLR
(5' CACTAGCCGACCTTGACCCCTGTT 3'
SEQ ID NO: 5);

Prrn
(Forward: 5' ATCGATGAGCCTGATTATCCTAAG 3'
SEQ ID NO: 6;
Reverse 5' CAGCAGGTAGACAAAGCGGATTC 3'
SEQ ID NO: 7), PpsbA
(Forward 5' GATATCGTCGACGTAGAGAAGTCCG 3'
SEQ ID NO: 8;
Reverse 5' CATATGAAAATCTTGGTTTATTTAA 3'
SEQ ID NO: 9);

TpsbA
(Forward 5' TCTAGAGCGATCCTGGCCTAG 3'
SEQ ID NO: 10;
Reverse 5' GAGCTCGCAGCCCAAACAAATAC 3'
SEQ ID NO: 11);

Trps16
(Forward 5' ACTAGTCCTAATCAACCGAAATTC 3'
SEQ ID NO: 12;
Reverse 5' GAGCTCGAACACGGAATTCAATGGAAGC 3'
SEQ ID NO: 13);

T7 gene 10
(Forward 5' GGTAACCCCGGGAGACCACAACGGTTTCCCTCTAGAAAT
AATTTTGTTTA 3'
SEQ ID NO: 14;
Reverse 5' CATATGTATATCTCCTTCTTAAAGTTA 3'
SEQ ID NO: 15);

3P
(5' AAAACCCGTCCTCAGTTCGGATTGC 3'
SEQ ID NO: 16).;

1M
(5' CGCGCTTAGCTGGATAACGCCACGGAA 3'
SEQ ID NO: 21);

16S F
(5' CAGCAGCCGCGGTAATACAGAGGA 3'
SEQ ID NO: 17).
```

The carrot specific chloroplast transformation vector pDD-Dc-aadA-BADH was constructed by inserting a blunt ended fragment representing the aadA-BADH expression cassette into PvuII site of carrot chloroplast DNA flanking sequences. All general bacterial and DNA manipulations were performed as per standard molecular biology protocols.

B. Transformation and Regeneration Protocol for Carrot.

Sterile carrot plants (*Daucus carota* L. cv. Half long) were raised in plant tissue culture tubes containing (MSB) MS salts, B5 vitamins, 2% sucrose and 0.8% agar in the medium. The stems were cut into 0.5 mm segments and placed on MSB solid medium supplemented with 3 mg/L 2,4-D and 1 mg/L kinetin for induction of callus. After bombardment with pDD-Dc-aadA-badh, embryogenic callus was incubated for 2 days in the dark and selected on MSB (3 mg/L 2,4-D+1 mg/L kinetin) containing different concentrations of spectinomycin (150, 250, 350 and 450 mg/L). Cultures were incubated in 16/8 h day/night cycle at 50-100 lux light intensity and 26±2° C. temperature. Transgenic cultures were multiplied using both solid and liquid medium supplemented with selection agent. Transgenic plants produced on MSB medium containing 0.2 mg/L kinetin were transferred to soil in pots.

C. Optimization of Transformation Parameters in Carrot.

For optimization of gene delivery, embryogenic cell culture of carrot was placed on Whatman # 1 filter paper, supported by MSB medium (3 mg/l 2,4-D+1 mg/l kinetin). Gene delivery was optimized using pDD-Dc-aadA/BADH vector coated on 0.6 µm gold particles using different rupture discs and at different distances between rupture discs and target tissues. Bombarded cell cultures were incubated in the dark for two days and transferred to selection medium containing 150 mg/l spectinomycin. Transgenic calli obtained at different bombardment parameters were tested for site-specific transgene integration into the plastid genome by PCR.

D. BADH Enzyme Activity and Immunoblot Analysis in Carrot.

Protein extraction and BADH (Betaine aldehyde dehydrogenase) activity assay were done as described above. One gram carrot tissues were homogenized in 2 mL homogenization buffer containing 50 mM Hepes-KOH (pH 8.0), 1 mM EDTA, by BADH was measured spectrophotometrically at 340 nm after 1 min and 10 min interval in 1 mL assay buffer (50 mM Hepes-KOH, pH 8.0; 1 mM EDTA, 5 mM DTT, 1 mM NAD20 mM Sodium metabisulfite, 10 mM Sodium borate, 5 mM ascorbic acid and 5 mM DTT. Crude extract was centrifuged at 10,000×g at 4° C. for 10 min and the supernatant was desalted using Sephadex G-25 Columns® Reduction of NAD+by BADH was measured spectrophotometrically at 340 nm after 1 min and 10 min intervals in 1 ml assay buffer (50 mM Hepes-KOH, pH 8.0; 1 mM EDTA, 5 mM DTT, 1 mM NAD+) at about 25° C. supplemented with 1 mM BA (Betaine aldehyde) to start the reaction.

For immunoblot analysis total soluble protein was isolated using 2× Laemmli buffer from 100 mg carrot tissues. The mixture was boiled for about 5 min and centrifuged for about 5 min at 10,000×g. Supernatant containing about 50 µg total soluble protein (quantified with Bradford assay) was loaded on a 10% SDS-PAGE gel and transferred to nitrocellulose membrane. Membrane was hybridized with polyclonal anti-BADH serum, raised in rabbits against BADH. Hybridizing peptides were detected using horseradish peroxidase-linked secondary antibody, using Lumi-Phos™ WB chemiluminescent reagent®.

E. Salt Tolerance in Cell Suspension Cultures of Carrot.

To assess the effect of salt stress on chloroplast transgenic cell suspension cultures of carrot, cells were grown in liquid MSB media (0.1 mg/L 2,4-D) supplemented with 0-300 mM NaCl. Cultures were maintained at 130 rpm under diffuse light at 28±20 C for two weeks. Cells were harvested on a filter disk in a filtration apparatus and their relative weight was recorded.

F. Determination of Betaine Concentration by 1H-NMR.

Transgenic and non-transgenic carrot cell cultures were grown in the presence of NaCl (0, 100 mM) and choline (0, 4 mM) in liquid medium to measure betaine accumulation. Plant samples were prepared as described previously. The 1H-NMR spectra (500 MHz,) were recorded at about 25° C., at 32 pulses, with a pulse repletion time of about 5 second and r.f. pulse angle of about 30°. For betaine determinations with $^1$H-NMR, purified samples were dried via rotary evaporator and dissolved in 0.6 ml of D2O. t-Butanol was added as an internal standard. A dominant singlet (peak) assignable to the authentic betaine methyl groups [R—N+(CH3)3] was detected at 3.20 ppm. Integration of the singlet versus t-butanol was used for quantification.

G. Analysis of Transgenic Plants for Salt Tolerance in Carrot.

Transgenic and non-transgenic carrot plants of similar age and height were assayed for salt tolerance after transfer to soil in pots containing 0, 100, 200, 300, 400 and 500 mM NaCl. Plants were maintained in growth chamber and irrigated daily with saline water containing above-mentioned levels of salt for one month.

H. Results

Construction of carrot plastid transformation vector: Carrot chloroplast transformation vector targets the expression cassette to the 16S/trnI-trnA/23S region of the chloroplast genome for integration via homologous recombination. The site of integration is similar to the universal chloroplast transformation vector (pLD CtV) reported earlier from our laboratory. For the construction of carrot specific chloroplast transformation vector, flanking region was amplified from carrot genomic DNA. In the absence of chloroplast genome sequence information for carrot, primers were designed based on the sequence information available for tobacco. PCR amplification of the flanking region from carrot resulted in an approx. 4.0 kb DNA fragment that is approximately twice the size of flanking region used in pLD CtV vector. The size of the flanking sequence was increased in order to enhance the efficiency of homologous recombination. Carrot specific chloroplast transformation vector (pDD-Dc-aadA/BADH) harbors the aadA gene regulated by the 5' ribosome binding site (rbs) region or the Shine-Dalgarno sequence (GGAGG)/psbA 3' UTR and the BADH gene regulated by the 5' ribosome binding site (rbs) region of the bacteriophage T7 gene 10 leader; in order to facilitate expression in green as well as non-green tissues/rps16 3' UTR. Transcription of the expression cassette in carrot chloroplast transformation vector is driven by the full-length 16S rRNA promoter (Shinozaki et al., 1986). The full-length promoter comprised of binding sites for both the plastid-encoded and nuclear-encoded RNA polymerase thereby facilitating transcription in green or non-green tissues. All the 5' and 3' regulatory elements were PCR amplified from the tobacco genomic DNA except for the T7 gene 10 5' UTR which was PCR amplified from pET 11 vector (NEB).

I. Transformation of Carrot Plastid Genome and Plant Regeneration.

Yellow fine cell suspension culture induced from stem segments of carrot (Daucus carota L. cv. Half long) was bombarded with carrot chloroplast transformation vector pDD-Dc-aadA/badh. Using the carrot chloroplast transformation vector, several independent transgenic cell lines were recovered. The transgenic calli were transferred to 350-mg/L spectinomycin for a month and subsequently multiplied using 500-mg/L spectinomycin. In order to further multiply the transgenic cell cultures, they were either subcultured on solid medium every 2-3 weeks or rapidly multiplied in a liquid medium (MSB+0.1 mg/L 2,4-D) maintained at 130 rpm under diffuse light (50 lux) each week. Transgenic carrot plants produced from somatic embryos on basal MSB medium (containing 500 mg/L spectinomycin) were transferred to soil in pots for the development of mature taproot and further molecular characterization.

J. Optimization of Plastid Transformation.

Plastid transformation efficiency is very high in tobacco (approximately 15 events per bombarded leaf; but less inefficient in other crops, including other *Solanaceous* species. A plastid transformation protocol was optimized using different bombardment conditions to achieve reproducibility using carrot cell cultures. In order to optimize gene delivery, carrot specific chloroplast transformation vector pDD-Dc-aadA/badh was bombarded using rupture discs of different pressure at various distances between the rupture discs and the target tissues. Maximum transformation efficiency (23.3%) was observed with carrot cell cultures bombarded at 1100 psi pressure and at a distance of 12 cm. Considerably low efficiencies were obtained at other pressures and distances used for particle bombardment.

K. Visible Selection of Transgenic Carrot Cells.

During in vitro cell culture studies of transgenic and non-transgenic carrot, it was interesting to note that chloroplast transgenic carrot cells could be distinguished on the basis of color. Transgenic calli derived from cultured cells expressing BADH transgene were always green in color whereas non-transgenic cells were yellow in color. To examine whether the transgenic bright green cells were truly transgenic, heteroplasmic (partially transformed plastids) carrot cell cultures were placed on a growth medium without selection and were allowed to segregate; green and yellow cells visually segregated within 3-4 weeks. Further, transgene integration in green carrot cells was confirmed by PCR using 16SF and aphA6-rev primer pair.

It has been shown that in the presence of glycine betaine, light-dependent repair of photosystem II complex is accelerated and favored over its photo-induced damage. Rubisco has been shown to be protected in the presence of glycine betaine. Thus the observed greening of BADH expressing carrot cells may, for example, be a consequence of increased glycine betaine accumulation in the transformed cells that prevents the photosynthesis apparatus from degradation. Visible distinction based on green color phenotype may be employed in future strategies for maintaining the transgenic status of transformed cell lines after the removal of stably integrated or transiently cointegrated antibiotic selectable markers.

L. Confirmation of Transgene Integration into Carrot Plastid Genome

The carrot chloroplast vector pDD-Dc-aadA/badh integrates the aadA and BADH genes into the 16S-23S-spacer region of the plastid genome by homologous recombination. Transgene integration into carrot plastid genome was confirmed by PCR using internal primers 3P (that lands on trnI region of plastids) and 3M (that lands on the aadA gene) producing 1.6 kb PCR product. This eliminates mutants that may arise due to a mutation in the chloroplast 16S rRNA gene. In order to distinguish between nuclear and chloroplast transgenic cell lines, 16S-F primer was landed on the native chloroplast genome, 200 bp upstream of integration site and 1M primer was landed on the aadA gene; this generated 2.5 kb size PCR product confirming site specific integration of the transgene cassette.

Southern blot analysis was performed using total genomic DNA isolated from untransformed and transformed carrot plants, generated from different transgenic cell lines. Total genomic DNA was digested with AflIII and PvuII restriction enzymes. In order to investigate homoplasmy or heteroplasmy, total genomic DNA from carrot plants, digested with AflIII and PvuII, was hybridized with a 3.2 kb radiolabeled DNA fragment isolated from the chloroplast transformation vector pDD-Dc-aadA/badh, by digesting it with AflIII and PvuII; this fragment includes the 1.4 kb trnI flanking sequence and 1.8 kb transgene sequences of the chloroplast transformation vector. Transgenic plants regenerated after two subcultures in selective liquid medium (350 mg/L spectinomycin) showed heteroplasmy as is evident by the presence of both 1.4 kb wild type and 3.2 kb transformed chloroplast genomes. Plants that were regenerated from cell lines after 8-10 subcultures in liquid medium supplemented with a high concentration of antibiotic (500 mg/L spectinomycin) exhibited almost complete homoplasmy as only the 3.2 kb DNA fragment, representing transformed chloroplast genomes, was observed. A very faint signal corresponding to the wild-type fragment was observed in cell lines that have not gone through repetitive stringent selection; subsequent rounds of selection eliminated this wild-type fragment. Observation of slight heteroplasmy into transgenic lines and conversion to complete homoplasmy in T1 transgenic lines, upon germination of seeds under stringent selection, is of common occurrence in chloroplast transgenic lines.

M. BADH Enzyme Activity in Carrot Cells, Root and Shoot.

BADH enzyme activity was assayed in crude extracts from untransformed and transformed carrot cell-cultures, tap-roots (carrot) and leaves as described. By assessing BADH enzyme activity in cells and different parts of carrot plants expression of the BADH transgene was characterized. In the presence of betaine aldehyde, BADH enzyme reduces NAD+ to NADH and the rate of this reaction was measured by an increase in absorbance at 340 nm due to the reduction of NAD+. Crude extracts from chloroplast transgenic tissues (cells, tap roots and leaves) showed elevated levels of BADH activity compared to untransformed tissues of carrot. High BADH activity was observed in leaves, tap roots of carrot plant and transgenic cells in suspension culture, confirming that full-length 16S promoter Prrn and gene10 5' UTR are highly suitable for expressing transgenes in different tissues.

N. BADH Protein Expression in Carrot Cells, Root and Shoot.

To further confirm the results of BADH activity in cells, tap roots and leaves, western blot analysis was performed using crude extracts of transformed and untransformed carrot tissues. Protein transferred to nitrocellulose membrane was hybridized with polyclonal anti-BADH serum, raised in rabbits against native BADH and antigenic peptides were detected using horseradish peroxidase-linked secondary antibody. No BADH expression was detected in untransformed carrot tissues (cells, tap roots and leaves). However, in chloroplast transgenic samples, higher expression was observed in leaves and taproots compared to carrot cell suspension cultures. BADH protein accumulation in carrot root and leaf tissues was in agreement with the BADH enzyme activity observed in transgenic roots and shoots.

O. Salt Tolerance and BADH Activity in Cell Suspension Cultures of Carrot.

In order to test whether salt stress affected BADH enzyme activity in chloroplast transgenic cell lines, experiments were performed under different salt concentrations (0-300 mM NaCl). It was observed that transformed cells were able to survive and proliferate at high concentrations of NaCl in the liquid medium when compared to untransformed cells. In two replicates, both transgenic and wild type carrot cultures produced about an average of 11.82±0.18 g cells (1475%) in the absence of NaCl while, in the presence of 100 mM NaCl, 8.75±0.13 g (1096%) and 1.29±0.14 g (161%) of chloroplast transgenic and wild type cells were produced respectively from 0.8 g (control as 100%) of initially inoculated cell culture. Further, BADH enzyme activity was enhanced 8.05 fold in transgenic carrot cell cultures in the presence of 100 mM NaCl when compared to untransformed cells. This shows that full length Prrn promoter and gene 10 5' UTR facilitate efficient transcription and translation in all tissues, irrespective of the developmental stage, despite low copy number of plastid genomes in non-green cells or roots.

P. Betaine Accumulation in Carrot Cells.

Because transformed carrot cells expressed BADH (confirmed by western blot) and also showed BADH enzyme activity, it is logical to evaluate accumulation of betaine in these cells. Therefore, betaine concentration was measured by 1H-NMR The level of betaine observed was 26.5 µmol g-1 DW in the transgenic carrot cell DW) when transgenic cell suspension cultures were supplemented with 100 mM NaCl. However, in the presence or absence of choline as well as salt, no significant level of betaine was recorded in the untransformed control carrot cell cultures. Transformed carrot cells grown in 100 mM NaCl accumulated 50-54 fold more betaine than untransformed cells (in the presence or absence of choline), when determined on the basis of dry weight. Members of the family Chenopodiaceae can accumulate high levels (>100 µmol g-1 DW) of betaine in leaves when salinized (Weretilnyk et al., 1989). While genetic engineering has allowed engineered plants to produce betaine, there are considerable differences in levels of betaine, on a fresh weight basis, among nuclear transgenic plants (0.05-5 µmol g-1 FW) and natural accumulators under stress conditions (4-40 µmol g-1 FW). Recently, 167 µmol g-1 DW betaine in Sea blite was reported that was collected from a saline area of China that belongs to Chenopodiaceae and known as a strong halophytic plant. Using 1H-NMR spectroscopy, we have observed about 93 µmol g-1 DW betaine in transgenic tissues when cell cultures were grown in liquid medium containing 100 mM NaCl for two weeks. While this level of accumulation is adequate to confer salt tolerance (up to 300 mM NaCl, higher betaine accumulation may occur in the transgenic leaf or root tissues, as BADH activity was much higher in transgenic plants when compared to carrot cell cultures and transgenic plants were able to grow in the presence of 400 mM NaCl.

Previous studies demonstrated that choline fed transgenic plants synthesized more betaine because endogenous choline supply limits betaine synthesis in transgenic tobacco, *Arabidopsis* and *Brassica* plants. In order to test the role of endogenous choline monoxygenase, carrot cell cultures were grown in the presence or absence of choline. We observed slight enhancement of betaine accumulation in the transgenic carrot cell suspension cultures that were supplemented with 4 mM choline along with 100 mM salt. In embodiments, the lack of an increase in betaine in the presence of choline may be due to limitation of choline monoxygenase or uptake of choline by carrot cells.

BADH is not substrate-specific, as had been reported previously. It plays several roles in plants during salt stress and helps in the accumulation of osmolytes like glycine betaine and β-Alanine betaine. Glycine betaine is produced in plants by a two-step oxidation of choline while β-alanine betaine is produced after methylation of β-Alanine, converted from 3-aminopropionaldehyde by BADH enzyme. In the salinized plants, quaternary ammonium compounds β-Alanine betaine [(CH3)3—N+—CH2—CH2—COO—] has shown better osmoprotective properties than glycine betaine [(CH3)3—N+—CH2—COO—]. Since 1H-NMR spectra detects both quaternary ammonium compounds as betaine, levels of betaine reported here do not distinguish between β-Alanine betaine and glycine betaine.

While BADH activity increased ~8 fold in transformed carrot cells compared to untransformed cells when grown in the presence of 100 mM NaCl, betaine accumulation increased 55 fold. Under similar physiological conditions, transformed cells grew ~7 fold more than transformed cells when grown in the presence of 100 mM NaCl. Even though, accumulation of betaine is quite high, osmoprotection mechanism in combination with other mechanism (such as anti-port) may yield plants with even higher level of salt tolerance.

Q. Effect of Salt Stress on Carrot Plants.

Chloroplast transgenic carrot plants and wild type plants were subjected to increasing degree of salt stress ranging from 100-500 mM NaCl. Chloroplast transgenic plants expressing the BADH transgene thrive well up to 400 mM NaCl where as untransformed plants exhibited severe growth retardation at 200 mM NaCl. The understanding of metabolic fluxes in plant cells and the ability to synthesize compatible solutes have opened up the possibility of genetically modifying plants to confer stress tolerance. Improved salinity tolerance has been achieved by over expressing a vacuolar Na+/H=antiport up to 200 mM NaCl, or by the accumulation of glycine betaine via expression of BADH alone up to about 120 mM NaCl, or co-expression of BADH and CDH up to about 200 mM NaCl. Expression of BADH alone in transgenic plants via the chloroplast genome was adequate to confer higher levels of salinity tolerance (up to 400 mM NaCl).

Carrot chloroplast transgenic lines are able to grow well at 400 mM NaCl, a concentration at which only halophytes are able to thrive. In contrast, untransformed wild type line exhibits severe growth retardation even at 200 mM NaCl. So far, only the tobacco chloroplast genome has been engineered to confer herbicide resistance, insect resistance, disease resistance, drought tolerance, or phytoremediation of toxic metals. Efficient transformation of carrot chloroplast genome was achieved (1 event per ~4 bombarded plates) using species-specific chloroplast vector containing 100% homologous flanking sequences.

The use of non-green explants has often been cited as one of the major obstacles that has limited the chloroplast transformation to *Solanaceous* crops. In carrot plastid transformation, the expression cassette for the detoxification of antibiotic is functional in non-green cells due to the full length Prrn promoter used in the cassette that has binding sites for both the nuclear encoded and plastid encoded RNA polymerase. Because most of the crop species are regenerated via somatic embryogenesis, methods developed here scan be used in transforming the plastid genomes of other crop plants. Both the selectable marker and the gene of interest (aadA and BADH are transcribed by the plastid Prrn promoter; this 16S rRNA promoter drives the entire rRNA operon in the native chloroplast and contains binding sites for both the nuclear encoded and plastid encoded RNA polymerases. This promoter is capable of functioning in both proplastids and chloroplasts (green and non-green, in the light and dark). The BADH gene is further regulated by the T7 gene 10 5' UTR capable of efficient translation in the dark and in proplastids present in non-green tissues. It should be noted that the heterologous T7 gene 10 5' UTR that regulates translation of the BADH gene was indeed promoterless and the transgene expression could be further enhanced by adding a suitable promoter, which could further enhance salt tolerance.

All references contained herein and throughout the application, as well as all references listed in the reference section are fully incorporated by reference into the application.

I claim:

1. A plant produced by somatic embryogenesis, wherein the plastids of the plant are transformed with an expression cassette for facilitating somatic embryogenesis, said expression cassette comprising, in 5' to 3'order,
 a first 5' control sequence functional in a plastid controlling the expression of a first selectable marker sequence encoding a first selectable marker protein;
 a second 5' control sequence functional in a plastid controlling the expression of a second selectable marker sequence encoding a second selectable marker protein
 a first 3' transcriptional termination sequence; and
 a first DNA flanking sequence on the 5' end and second DNA flanking sequence on the 3' end of said expression cassette, wherein said flanking sequences facilitate stable integration of the expression cassette with genomic plastic DNA by homologous recombination;
 wherein said first 5' control sequence is constitutive; and said second 5' control sequence is light-regulated or constitutive, resulting in said second selectable marker protein being produced in both green and non-green tissue, and under light and dark conditions;
 wherein said plant is homoplasmic with respect to said expression cassette; and
 wherein said first selectable marker protein is different from said second selectable marker protein but wherein said first selectable marker protein and said second selectable marker protein provide resistance to a plant cell to a common selection agent.

2. The plant of claim 1, wherein said selection agent is an aminoglycoside antibiotic.

3. The plant of claim 2, wherein the aminoglycoside antibiotic is kanamycin.

4. The plant of claim 1, wherein said first selectable marker sequence is aphA6 and said second selectable marker sequence is nptII.

* * * * *

UNITED STATES PATENT AND TRADEMARK OFFICE
CERTIFICATE OF CORRECTION

PATENT NO. : 7,767,885 B2  
APPLICATION NO. : 11/190122  
DATED : August 3, 2010  
INVENTOR(S) : Henry Daniell It is certified that error appears in the above-identified patent and that said Letters Patent is hereby corrected as shown below:

In the Specification

Col. 1, line 23 under the STATEMENT REGARDING FEDERALLY SPONSORED RESEARCH section (LINES 26-29), please delete "The subject invention was made with government support under a research project supported by National Institutes of Health Grant No R 01 GM63879. The government has certain rights in this invention" and insert --Development of the invention was supported by government support under grant numbers USDA/ARS 58-3611-7-610 awarded by the United States Department of Agriculture and NIH R01 GM 063879 awarded by the National Institutes of Health. The U.S. government has certain rights in the invention.--

Signed and Sealed this  
Seventeenth Day of September, 2013

Teresa Stanek Rea  
*Deputy Director of the UnitedStates Patent and Trademark Office*

UNITED STATES PATENT AND TRADEMARK OFFICE
CERTIFICATE OF CORRECTION

PATENT NO. : 7,767,885 B2  
APPLICATION NO. : 11/190122  
DATED : August 3, 2010  
INVENTOR(S) : Henry Daniell Page 1 of 1

It is certified that error appears in the above-identified patent and that said Letters Patent is hereby corrected as shown below:

In the Specification

Col. 1, line 23 under the STATEMENT REGARDING FEDERALLY SPONSORED RESEARCH section (LINES 26-29), please delete "The subject invention was made with government support under a research project supported by National Institutes of Health Grant No R 01 GM63879. The government has certain rights in this invention" and insert --This invention was made with government support under grant numbers USDA/ARS 58-3611-2-106 awarded by the United States Department of Agriculture and NIH R01 GM 063879 awarded by the National Institute of Health. The U.S. government has certain rights in the invention.--

Signed and Sealed this  
Twenty-fifth Day of March, 2014

Michelle K. Lee  
*Deputy Director of the United States Patent and Trademark Office*

SEQUENCE LISTING

<160> NUMBER OF SEQ ID NOS: 21

<210> SEQ ID NO 1
<211> LENGTH: 2800
<212> TYPE: DNA
<213> ORGANISM: ARTIFICIAL
<220> FEATURE:
<223> OTHER INFORMATION: aadA/BADH expression cassette

<400> SEQUENCE: 1

```
agcttgcggg ccccccctcg aggtcgacgg tatcgatgag cctgattatc cctaagccca      60
atgtgagttt ttctagttgg atttgctccc ccgccgtcgt tcaatgagaa tggataagag     120
gctcgtggga ttgacgtgag ggggcaggga tggctatatt tctgggagcg aactccgggc     180
gaatatgaag cgcatggata caagttatgc cttggaatga aagacaattc cgaatccgct     240
ttgtctaccc gatacaagtg agttgtaggg aggcaaccat ggcagaagcg gtgatcgccg     300
aagtatcgac tcaactatca gaggtagttg gcgtcatcga gcgccatctc gaaccgacgt     360
```

-continued

```
tgctggccgt acatttgtac ggctccgcag tggatggcgg cctgaagcca cacagtgata   420
ttgatttgct ggttacggtg acggtgaccg taaggcttga tgaaacaacg cggcgagctt   480
tgatcaacga ccttttggaa acttcggctt ccccctggaga gagcgagatt ctccgcgctg   540
tagaagtcac cattgttgtg cacgacgaca tcattccgtg gcgttatcca gctaagcgcg   600
aactgcaatt tggagaatgg cagcgcaatg acattcttgc aggtatcttc gagccagcca   660
cgatcgacat tgatctggct atcttgctgg caaaagcaag agaacatagc gttgccttgg   720
taggtccagc ggcggaggaa ctctttgatc cggttcctga acaggatcta tttgaggcgc   780
taaatgaaac cttaacgcta tggaactcgc cgcccgactg ggctggcgat gagcgaaatg   840
tagtgcttac gttgttccgc atttggtaca gcgcagtaac cggcagaatc gcgccgaagg   900
atgtcgctgc cgactgggca atggagcgcc tgccggccca gtatcagccc gtcatacttg   960
aagctagaca ggcttatctt ggacaagaag aagatcgctt ggcctcgcgc gcagatcagt   1020
tggaagaatt tgttcactac gtgaaaggcg agatcaccaa ggtagtcggc aaataaaaag   1080
ccgaatctag agcgatcctg cctagtctaa taggaggttt tgaaaagaaa ggagcaataa   1140
tcattttctt gttctatcaa gagggtgcta ttgctccttt cttttttttct ttttatttat   1200 ttactagtat tttacttaca tagactttttt tgtttacatt atagaaaaag aaggagaggt   1260
tattttcttg catttattca tgattgagta ttctattttg attttgtatt tgtttgggct   1320
gcgcggggag accacaacgg tttccctcta gaaataattt tgtttaactt taagaaggag   1380
atataccatg gcgttcccaa ttcctgctcg tcagctattc atcgacggag agtggagaga   1440
acccattaaa aaaaatcgca tacccgtcat caatccgtcc actgaagaaa tcatcggtga   1500
tattccggca gccacggctg aagatgtgga ggttgcggtg gtggcagctc gaagagcctt   1560
taggaggaac aattggtcag caacatctgg ggctcatcgt gccacatact tgcgtgctat   1620
tgctgctaag ataacagaaa aaaagatcag tttcgttaaa ctggaaacca ttgattctgg   1680
gaaacctttt gatgaagcag tgctggacat tgatgacgtt gcttcatgtt ttgaatattt   1740
tgccggacaa gcagaagctc ttgatggtaa acaaaaggct ccagtcaccc tgcctatgga   1800
aaggttcaaa agtcatgttc tcaggcagcc ccttggtgtt gttggattaa tatccccatg   1860
gaattaccca cttctaatgg ctacatgaaa aattgctcca gcacttgctg ctgggtgtac   1920
agctgtactt aagccatccg agttggcatc tgtgacttgt ctagaattcg gtgaagtttg   1980
caacgaagtg ggacttcctc caggcgtgtt gaatatcttg acaggattag gtccagatgc   2040
tggtgcacca ttagtatcac accccgatgt tgacaagatt gcctttactg ggagtagtgc   2100
cactggaagc aaggttatgg cttctgctgc ccaattggtt aagcctgtta cattagaact   2160
tgggggtaaa agtcctattg tagtgtttga agatgttgat attgataaag ttgtggaatg   2220
gactattttt ggctgtttct ggacaaatgg tcaaatatgt agtgcaacgt ctagactgct   2280
tgtgcatgaa agtattgcag ctgagtttgt tgataagctt gtaaatggca cgaaaaacat   2340
taaaatttct gacccatttg aagaaggatg ccggcttggc cctgttatta gtaaaggaca   2400
gtacgacaaa attatgaagt tcatatcaac agcaaagagt gagggggcaa ctattttgta   2460
tggaggttcc cgtcctgagc atttgaagaa aggttattac attgaaccca ccattgtaac   2520
tgatatctcc acatccatgc aaatatggaa agaggaagtt tttggccctg tcttgtgtgt   2580
taaaacattt agttccgaag atgaagccat tgcattggca aatgatacag agtacggttt   2640
agctgctgct gtgttttcta atgatcttga aagatgtgag aggataacga aggctctaga   2700
```

```
agttggagct gtttgggtta attgctcaca accatgcttt gttcaagctc cttggggagg    2760
catcaagcgt agtggttttg dacgtgaact tggagaatgg                          2800

<210> SEQ ID NO 2
<211> LENGTH: 3119
<212> TYPE: DNA
<213> ORGANISM: ARTIFICIAL
<220> FEATURE:
<223> OTHER INFORMATION: gfp/BADH expression cassette

<400> SEQUENCE: 2
cgggcccccc ctcgaggtcg acggtatcga tgagcctgat tatccctaag cccaatgtga      60 gttttctag ttggatttgc tccccgccg tcgttcaatg agaatggata agaggctcgt      120
gggattgacg tgagggggca gggatggcta tatttctggg agcgaactcc gggcgaatat     180
gaagcgcatg gatacaagtt atgccttgga atgaaagaca attccgaatc cgctttgtct     240
accgggagac cacaacggtt tccctctaga ataattttg tttaactta agaaggagat       300 atacccatgt ccatgagtaa aggagaagaa cttttcactg gagttgtccc aattcttgtt     360
gaattagatg gtgatgttaa tgggcacaaa ttttctgtca gtggagaggg tgaaggtgat     420
gcaacatacg gaaaacttac ccttaaattt atttgcacta ctggaaaact acctgttcca     480
tggccaacac ttgtcactac tttctcttat ggtgttcaat gcttttcaag atacccagat     540
catatgaagc ggcacgactt cttcaagagc gccatgcctg agggatacgt gcaggagagg     600
accatctctt tcaaggacga cgggaactac aagacacgtg ctgaagtcaa gtttgaggga     660
gacaccctcg tcaacaggat cgagcttaag ggaatcgatt tcaaggagga cggaaacatc     720
ctcggccaca gttggaata caactacaac tcccacaacg tatacatcac ggcagacaaa     780
caaaagaatg gaatcaaagc taacttcaaa attagacaca cattgaaga tggaagcgtt      840 caactagcag accattatca acaaatact ccaattggcg atggccctgt ccttttacca      900
gacaaccatt acctgtccac acaatctgcc ctttcgaaag atcccaacga aaagagagac     960
cacatggtcc ttcttgagtt tgtaacagct gctgggatta cacatggcat ggatgaacta    1020
tacaaataat ctagaaagcc gaattctgca gatcgaacac ggaattcaat ggaagcaatg    1080
ataaaaaaat acaaatagaa aaggaaaggg aggaaataca aaaaaataga agagaaaagt    1140
catacaaagt tatatacaaa tgactacccc ccttttttgta tttccttaat ttatttcctt    1200
aattgaattt cgatggatac aagttatgcc ttggaatgaa tttcggttga ttaggactag    1260
cgataagctt gatatcgaat tcggcttgat atcgtcgacg tagagaagtc cgtatttttc    1320
caatcaactt cattaaaaat ttgaatagat ctacatacac cttggttgac acgagtatat    1380
aagtcatgtt atactgttga ataaaaagcc ttcatttttc tattttgatt tgtagaaaac    1440
tagtgtgctt gggagtccct gatgattaaa taaaccaaga ttttccatgg cgttcccaat    1500
tcctgctcgt cagctattca tcgacggaga gtggagagaa cccattaaaa aaatcgata      1560 cccgtcatca atccgtccac tgaagaaatc atcggtgata ttccggcagc acggctgaa      1620 gatgtggagg ttgcggtggt ggcagctcga agagccttta ggaggaacaa ttggtcagca    1680
acatctgggg ctcatcgtgc cacatacttg cgtgctattg ctgctaagat aacagaaaaa    1740
aaagatcatt tcgttaaaact ggaaaccatt gattctggga aacctttga tgaagcagtg    1800 ctggacattg atgacgttgc ttcatgtttt gaatattttg ccggacaagc agaagctctt    1860
gatggtaaac aaaaggctcc agtcaccctg cctatgaaa ggttcaaaag tcatgttctc     1920
aggcagcccc ttggtgttgt tggattaata tccccatgga attccccact tctaatggct    1980
```

```
acatggaaaa ttgctccagc acttgctgct gggtgtacag ctgtacttaa gccatccgag    2040
ttggcatctg tgacttgtct agaattcggt gaagtttgca acgaagtggg acttcctcca    2100
ggcgtgttga atatcttgac aggattaggt ccagatgctg gtgcaccatt agtatcacac    2160
cccgatgttg acaagattgc ctttactggg agtagtgcca ctggaagcaa ggttatggct    2220
tctgctgccc aattggttaa gcctgttaca ttagaacttg ggggtaaaag tcctattgta    2280
gtgtttgaag atgttgatat tgataaagtt gtggaatgga ctattttttgg ctgtttctgg   2340 acaaatggtc aaatatgtag tgcaacgtct agactgcttg tgcatgaaag tattgcagct    2400
gagtttgttg ataagcttgt aaaatggacg aaaaacatta aaatttctga cccatttgaa    2460
gaaggatgcc ggcttggccc tgttattagt aaaggacagt acgacaaaat tatgaagttc    2520
atatcaacag caaagagtga gggggcaact attttgtatg gaggttcccg tcctgagcat    2580
ttgaagaaag ttattacat tgaacccacc attgtaactg atatctccac atccatgcaa    2640
atatggaaag aggaagttttt tggccctgtc ttgtgtgtta aacatttag ttccgaagat    2700 gaagccattg cattggcaaa tgatacagag tacggtttag ctgctgctgt gttttctaat    2760
gatcttgaaa gatgtgagag gataacgaag gctctagaag ttggagctgt ttgggttaat    2820
tgctcacaac catgctttgt tcaagctcct tggggaggca tcaagcgtag tggttttgga    2880
cgtgaacttg gagaatgggg tatccagaat tacttgaata tcaagcaggt gactcaagat    2940
atttctgatg aaccatgggg atggtacaag tctccttgaa agccgaattc cagcacactg    3000
gcggccgtta ctagtggatc cactagtaac ggccgccagt gtgctggaat tcggctttct    3060
agagcgatcc tggcctagtc tataggaggt tttgaaaaga aaggagcaat aatcattttt    3119

<210> SEQ ID NO 3
<211> LENGTH: 2569
<212> TYPE: DNA
<213> ORGANISM: ARTIFICIAL
<220> FEATURE:
<223> OTHER INFORMATION: aphA-6/nptII expression cassette

<400> SEQUENCE: 3 cgggccccccc ctcgaggtcg acggtatcga tgagcctgat tatccctaag cccaatgtga    60 gttttttctag ttggatttgc tccccgccg tcgttcaatg agaatggata agaggctcgt    120
gggattgacg tgaggggggca gggatggcta tatttctggg agcgaactcc gggcgaatat    180
gaagcgcatg gatacaagtt atgccttgga atgaaagaca attccgaatc cgctttgtct    240
acctgcagcc cgggagacca caacggtttc cctctagaaa taattttgtt taactttaag    300
aaggagatat accatggaat taccaaatat tattcaacaa tttatcggaa acagcgtttt    360
agagccaaat aaaattggtc agtcgccatc ggatgtttat tcttttaatc gaaataatga    420
aacttttttt cttaagcgat ctagcacttt atatacagag accacataca gtgtctctcg    480
tgaagcgaaa atgttgagtt ggctctctga aaattaaag gtgcctgaac tcatcatgac    540
ttttcaggat gagcagtttg aattcatgat cactaaagcg atcaatgcaa accaatttc    600 agcgcttttt ttaacagacc aagaattgct tgctatctat aaggaggcac tcaatctgtt    660
aaattcaatt gctattattg attgtccatt tatttcaaac attgatcatc ggttaaaaga    720
gtcaaaattt tttattgata accaactcct tgacgatata gatcaagatg attttgacac    780
tgaattatgg ggagaccata aaacttacct aagtctatgg aatgagttaa ccgagactcg    840
tgttgaagaa agattggttt tttctcatgg cgatatcacg gatagtaata ttttttataga    900
```

```
taaattcaat gaaatttatt ttttagatct tggtcgtgct gggttagcag atgaatttgt    960
agatatatcc tttgttgaac gttgcctaag agaggatgca tcggaggaaa ctgcgaaaat   1020
atttttaaag catttaaaaa atgatagacc tgacaaaagg aattattttt taaaacttga   1080
tgaattgaat tgattccaag cattatctaa aatactccta gagcggcccg aacacggaat   1140
tcaatggaag caatgataaa aaatacaaa tagaaaagga aagggaggaa atacaaaaaa    1200
atagaagaga aaagtcatac aaagttatat acaaatgact accccccttt ttgtatttcc   1260
ttaatttatt tccttaattg aatttcgatg gatacaagtt atgccttgga atgaatttcg   1320
gttgattagg actagatcgt cgacgtagag aagtccgtat ttttccaatc aacttcatta   1380
aaaatttgaa tagatctaca tacaccttgg ttgacacgag tatataagtc atgttatact   1440
gttgaataaa aagccttcca tttctattt tgatttgtag aaaactagtg tgcttgggag    1500
tccctgatga ttaaataaac caagattttc atatgattga acaagatgga ttgcacgcag   1560
gttctccggc cgcttgggtg gagaggctat tcggctatga ctgggcacaa cagacaatcg   1620
gctgctctga tgccgccgtg ttccggctgt cagcgcaggg gcgcccggtt cttttgtca    1680
agaccgacct gtccggtgcc ctgaatgaac tgcaggacga ggcagcgcgg ctatcgtggc   1740
tggccacgac gggcgttcct tgcgcagctg tgctcgacgt tgtcactgaa gcgggaaggg   1800
actggctgct attgggcgaa gtgccggggc aggatctcct gtcatctcac cttgctcctg   1860
ccgagaaagt atccatcatg gctgatgcaa tgcggcggct gcatacgctt gatccggcta   1920
cctgcccatt cgaccaccaa gcgaaacatc gcatcgagcg agcacgtact cggatggaag   1980
ccggtcttgt cgatcaggat gatctggacg aagagcatca ggggctcgcg ccagccgaac   2040
tgttcgccag gctcaaggcg cgcatgcccg acggcgatga tctcgtcgtg acccatggcg   2100
atgcctgctt gccgaatatc atggtggaaa atggccgctt ttctggattc atcgactgtg   2160
gccggctggg tgtggcggac cgctatcagg acatagcgtt ggctacccgt gatattgctg   2220
aagagcttgg cggcgaatgg gctgaccgct tcctcgtgct ttacggtatc gccgctcccg   2280
attcgcagcg catcgccttc tatcgccttc ttgacgagtt cttctgatct agagcgatcc   2340
tggcctagtc tataggaggt tttgaaaaga aaggagcaat aatcattttc ttgttctatc   2400
aagagggtgc tattgctcct ttctttttt cttttattt atttactagt attttactta    2460
catagacttt tttgtttaca ttatagaaaa agaaggagag gttattttct tgcatttatt   2520
catgattgag tattctattt tgattttgta tttgtttggg ctgcgagct              2569
```

<210> SEQ ID NO 4
<211> LENGTH: 25
<212> TYPE: DNA
<213> ORGANISM: Nicotiana tabacum

<400> SEQUENCE: 4
cactctgctg ggccgacact gacac                                          25

<210> SEQ ID NO 5
<211> LENGTH: 24
<212> TYPE: DNA
<213> ORGANISM: Nicotiana tabacum

<400> SEQUENCE: 5
cactagccga ccttgacccc tgtt                                           24

<210> SEQ ID NO 6
<211> LENGTH: 24

<212> TYPE: DNA
<213> ORGANISM: Nicotiana tabacum

<400> SEQUENCE: 6
atcgatgagc ctgattatcc taag                                          24

<210> SEQ ID NO 7
<211> LENGTH: 23
<212> TYPE: DNA
<213> ORGANISM: Nicotiana tabacum

<400> SEQUENCE: 7
cagcaggtag acaaagcgga ttc                                           23

<210> SEQ ID NO 8
<211> LENGTH: 25
<212> TYPE: DNA
<213> ORGANISM: Nicotiana tabacum

<400> SEQUENCE: 8
gatatcgtcg acgtagagaa gtccg                                         25

<210> SEQ ID NO 9
<211> LENGTH: 25
<212> TYPE: DNA
<213> ORGANISM: Nicotiana tabacum

<400> SEQUENCE: 9
catatgaaaa tcttggttta tttaa                                         25

<210> SEQ ID NO 10
<211> LENGTH: 21
<212> TYPE: DNA
<213> ORGANISM: Nicotiana tabacum

<400> SEQUENCE: 10
tctagagcga tcctggccta g                                             21

<210> SEQ ID NO 11
<211> LENGTH: 23
<212> TYPE: DNA
<213> ORGANISM: Nicotiana tabacum

<400> SEQUENCE: 11
gagctcgcag cccaaacaaa tac                                           23

<210> SEQ ID NO 12
<211> LENGTH: 24
<212> TYPE: DNA
<213> ORGANISM: Nicotiana tabacum

<400> SEQUENCE: 12
actagtccta atcaaccgaa attc                                          24

<210> SEQ ID NO 13
<211> LENGTH: 28
<212> TYPE: DNA
<213> ORGANISM: Nicotiana tabacum

<400> SEQUENCE: 13
gagctcgaac acggaattca atggaagc                                      28

<210> SEQ ID NO 14

```
<211> LENGTH: 50
<212> TYPE: DNA
<213> ORGANISM: Nicotiana tabacum

<400> SEQUENCE: 14
ggtaaccccg ggagaccaca acggtttccc tctagaaata attttgttta            50

<210> SEQ ID NO 15
<211> LENGTH: 27
<212> TYPE: DNA
<213> ORGANISM: Nicotiana tabacum

<400> SEQUENCE: 15
catatgtata tctccttctt aaagtta                                     27

<210> SEQ ID NO 16
<211> LENGTH: 25
<212> TYPE: DNA
<213> ORGANISM: Nicotiana tabacum

<400> SEQUENCE: 16
aaaacccgtc ctcagttcgg attgc                                       25

<210> SEQ ID NO 17
<211> LENGTH: 24
<212> TYPE: DNA
<213> ORGANISM: Nicotiana tabacum

<400> SEQUENCE: 17
cagcagccgc ggtaatacag agga                                        24

<210> SEQ ID NO 18
<211> LENGTH: 27
<212> TYPE: DNA
<213> ORGANISM: Nicotiana tabacum

<400> SEQUENCE: 18
cgagagacac actgtatgtg gtctctg                                     27

<210> SEQ ID NO 19
<211> LENGTH: 31
<212> TYPE: DNA
<213> ORGANISM: Nicotiana tabacum

<400> SEQUENCE: 19
ttaacatatg aggccttaga gcgatcctgg c                                31

<210> SEQ ID NO 20
<211> LENGTH: 27
<212> TYPE: DNA
<213> ORGANISM: ARTIFICIAL
<220> FEATURE:
<223> OTHER INFORMATION: UNKNOWN

<400> SEQUENCE: 20
caattgcaag agcggagctc taccaac                                     27

<210> SEQ ID NO 21
<211> LENGTH: 27
<212> TYPE: DNA
<213> ORGANISM: Nicotiana tabacum
```

```
<400> SEQUENCE: 21
cgcgcttagc tggataacgc cacggaa                                                27
```